US011008629B1

(12) United States Patent
Tanner et al.

(10) Patent No.: US 11,008,629 B1
(45) Date of Patent: May 18, 2021

(54) RAPID DIAGNOSTIC TEST USING COLORIMETRIC LAMP

(71) Applicant: New England Biolabs, Inc., Ipswich, MA (US)

(72) Inventors: Nathan Tanner, West Newbury, MA (US); Yinhua Zhang, North Reading, MA (US); Gregory Patton, Peabody, MA (US); Guoping Ren, Danvers, MA (US); Zhiru Li, Lexington, MA (US); Nicole Nichols, Reading, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 17/122,979

(22) Filed: Dec. 15, 2020

Related U.S. Application Data

(63) Continuation of application No. 16/938,575, filed on Jul. 24, 2020.

(60) Provisional application No. 63/048,556, filed on Jul. 6, 2020, provisional application No. 63/027,216, filed on May 19, 2020, provisional application No. 63/022,303, filed on May 8, 2020, provisional application No. 63/013,442, filed on Apr. 21, 2020, provisional application No. 63/001,909, filed on Mar. 30, 2020, provisional application No. 62/988,696, filed on Mar. 12, 2020.

(51) Int. Cl.
*G01N 21/78* (2006.01)
*C12Q 1/70* (2006.01)

(52) U.S. Cl.
CPC .............. *C12Q 1/701* (2013.01); *G01N 21/78* (2013.01)

(58) Field of Classification Search
CPC ................................ C12Q 1/701; G01N 21/78
See application file for complete search history.

(56) References Cited

U.S. PATENT DOCUMENTS

| | | | |
|---|---|---|---|
| 6,410,278 B1 | 6/2002 | Notomi et al. |
| 8,993,298 B1 | 3/2015 | Ong et al. |
| 9,034,606 B2 | 5/2015 | Tanner et al. |
| 9,074,243 B2 | 7/2015 | Tanner et al. |
| 9,074,249 B2 | 7/2015 | Tanner et al. |
| 9,121,046 B2 | 9/2015 | Tanner et al. |
| 9,127,258 B2 | 9/2015 | Ong et al. |
| 9,157,073 B1 | 10/2015 | Ong et al. |
| 9,546,358 B2 | 1/2017 | Tanner et al. |
| 9,580,698 B1 | 2/2017 | Xu et al. |
| 9,580,748 B2 | 2/2017 | Tanner et al. |
| 9,920,305 B2 | 3/2018 | Zhang et al. |

(Continued)

OTHER PUBLICATIONS

Huang et al. (2020) Lancet, 395, 497-506.

(Continued)

*Primary Examiner* — Jennifer Wecker
*Assistant Examiner* — Michael Paul Shimek
(74) *Attorney, Agent, or Firm* — New England Biolabs, Inc; Harriet M. Strimpel

(57) ABSTRACT

Kits and methods are provided for performing multiplex LAMP reactions. These kits and methods are directed to specific and sensitive methods of target nucleic acid detection and more specifically pathogen diagnostics such as detection of Coronavirus. The kits and methods utilize a plurality of sets of oligonucleotide primers for targeting the viral nucleic acid target.

29 Claims, 31 Drawing Sheets
(30 of 31 Drawing Sheet(s) Filed in Color)
Specification includes a Sequence Listing.

(56) References Cited

U.S. PATENT DOCUMENTS

| | | |
|---|---|---|
| 9,920,358 B2 | 3/2018 | Tanner et al. |
| 9,932,567 B1 | 4/2018 | Xu et al. |
| 10,253,357 B2 | 4/2019 | Mitra et al. |
| 10,597,647 B2 | 3/2020 | Zhu et al. |
| 2015/0247190 A1* | 9/2015 | Ismagilov ............ C12Q 1/6851 506/9 |
| 2019/0169683 A1 | 6/2019 | Zhang et al. |

OTHER PUBLICATIONS

To, et al., Clinical Infectious Diseases, ciaa149.
Wyllie, et al. MedRxiv Apr. 22, 2020: https://doi.org/10.1101/2020.04.16.20067835.
Notomi, et al. Nucleic Acid Research (2000) 28, E63.
Mori, et al., J. Infect. Chemother. 2009 15: 62-9.
Wastling, et al. (2010) PLoS Negl Trop Dis 4(11): e865. doi: 10.1371/journal.pntd.0000865.
Meredith, et al. Anal. Methods (2017) 9, 534-540.
Tanner, et al. (2015) Biotechniques, 58, 59-68.

\* cited by examiner

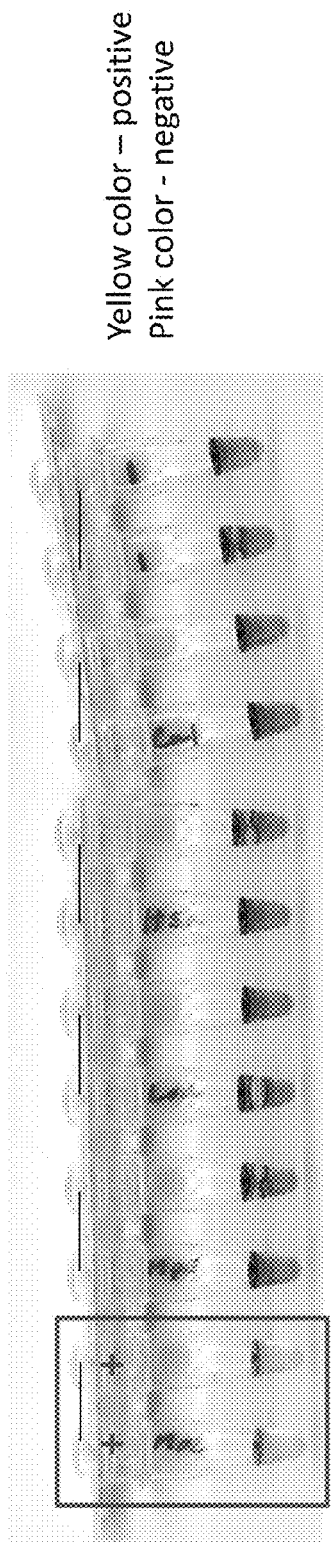
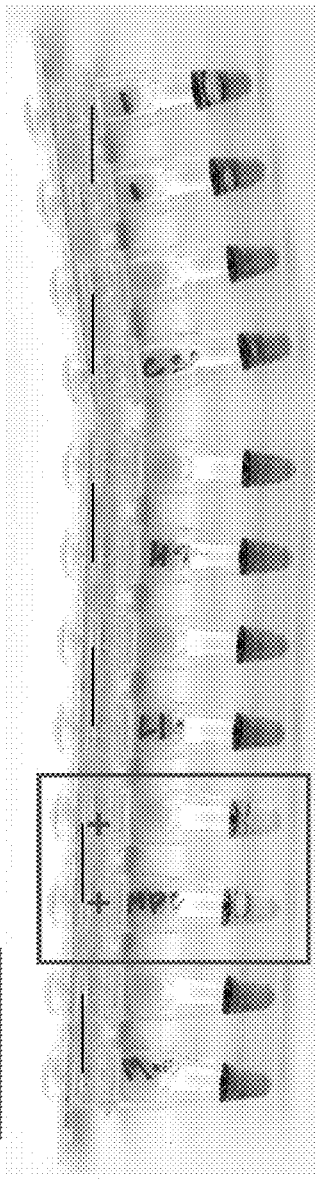
FIG. 4A Nematode 1 LAMP Test
FIG. 4B Nematode 2 LAMP test
Highly specific and sensitive - limit of detection 0.01-0.1 pg

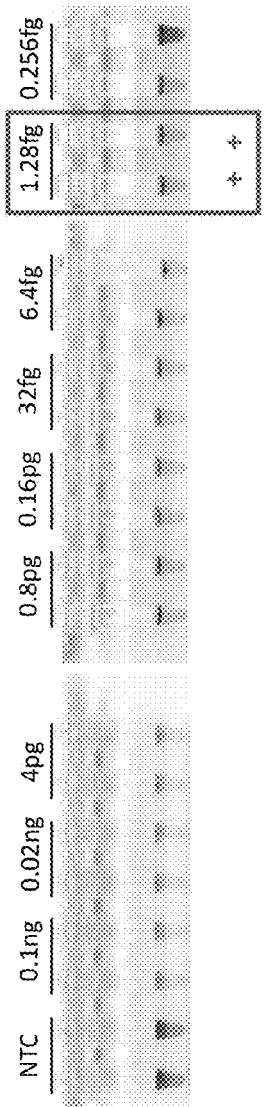
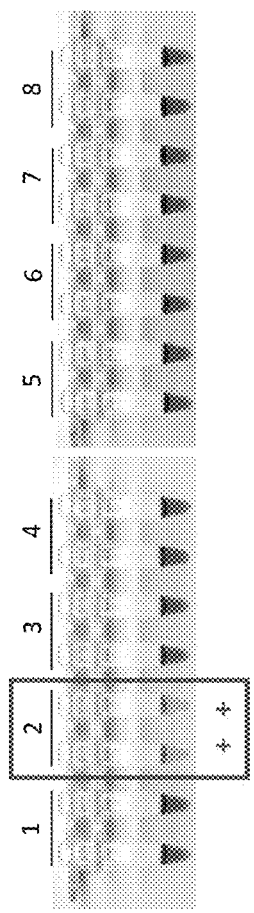

FIG. 5A Sensitivity

>10X more sensitive than best published qPCR method for pathogen target

FIG. 5B Specificity

Specific detection of pathogen target DNA

1: no template DNA control
2: pathogen target DNA
3: DNA from other tick-borne pathogen 1 – negative control
4: DNA from other tick-borne pathogen 2 – negative control
5: DNA from other tick-borne pathogen 3 – negative control
6: Tick DNA
7: Mosquito DNA
8: DNA from other tick-borne pathogen 4

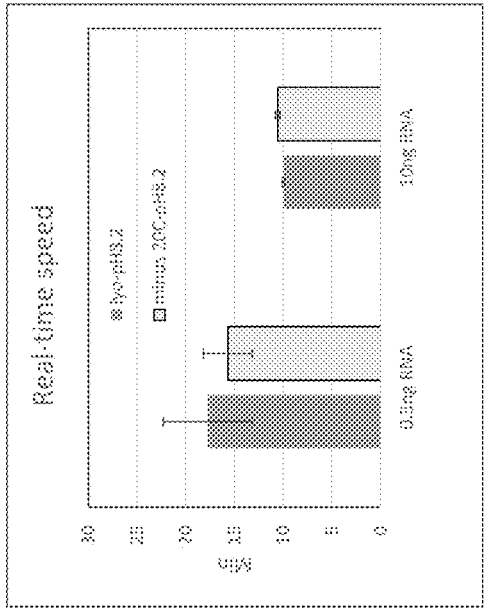
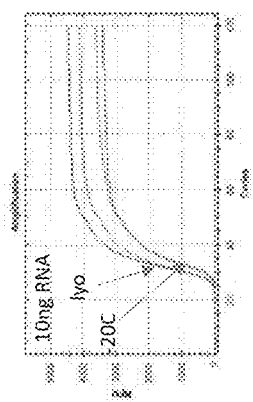
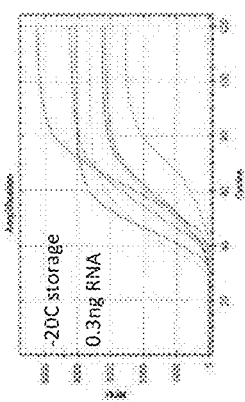
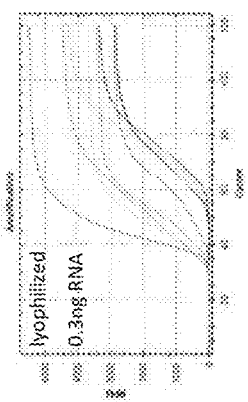
FIG. 8A
FIG. 8B
FIG. 8C

WarmStart Colorimetric LAMP 2X Master Mix (DNA & RNA)

(a) Complexation of 4-(2-pyridylazo)resorcinol (PAR) and metal ($M^{n+}$). (b) Paper-based spot test showing metal-PAR reactivity (orange and red color formation) for a number of transition, alkali, and alkaline earth metals.

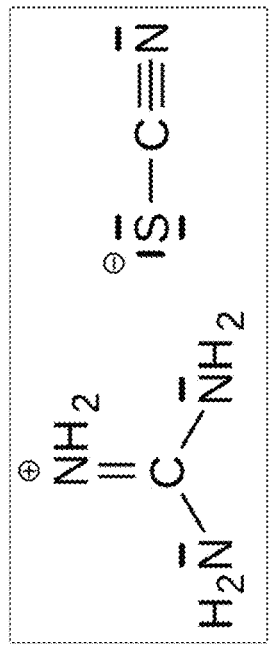
Guanidine hydrochloride (CAS#: 50-01-1)
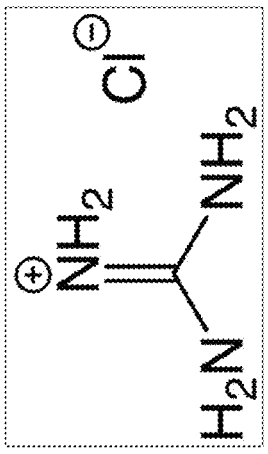
Arginine (CAS#: 7200-25-1)
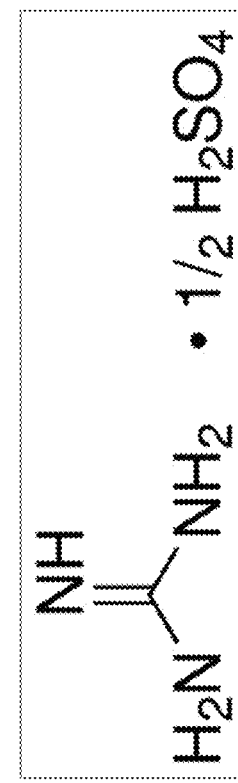
Guanidine thiocyanate (CAS#: 593-84-0)
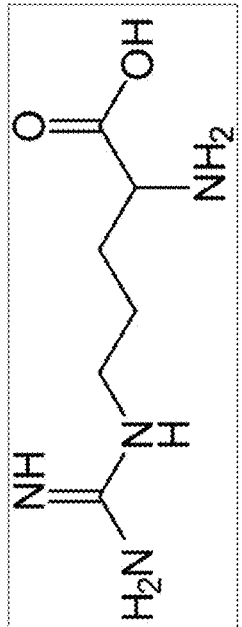
Guanidine sulfate (CAS#: 594-14-9)
FIG. 15

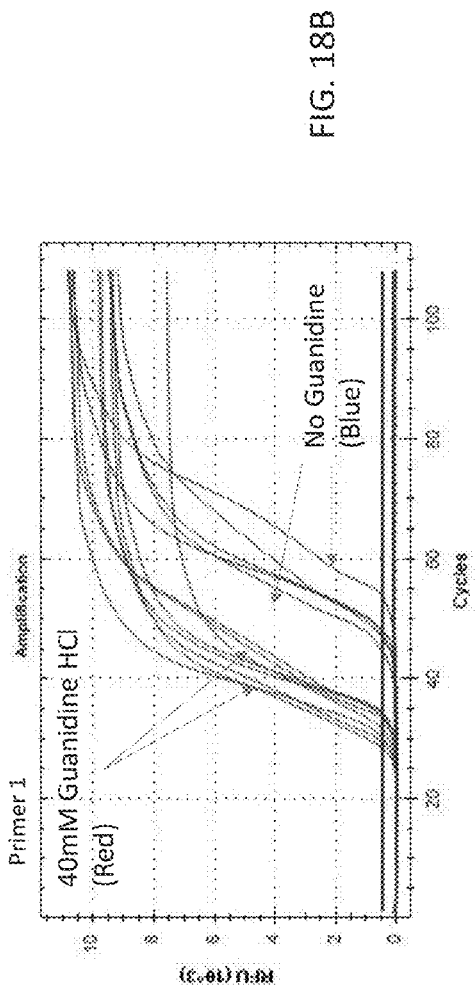
FIG. 18B
FIG. 18C
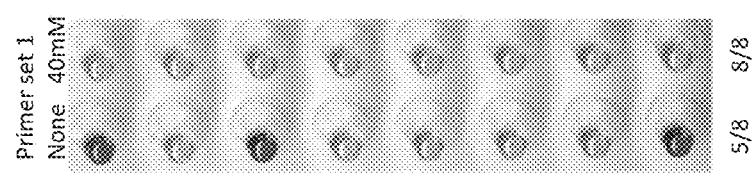
FIG. 18A

SARS-CoV-2 Genome and SARS-CoV-2 Rapid Colorimetric LAMP Assay Kit Gene Targets 1

FIG. 21A

| | GnHCl | TCEP [con] | TCEP pH | LiCl | SeraCare |
|---|---|---|---|---|---|
| 1 | 400mM | 1mM | 7.0 | 0 | 20,000 copies/mL |
| 2 | 400mM | 1mM | 7.0 | 75mM | 20,000 copies/mL |
| 3 | 400mM | 1mM | 8.0 | 0 | 20,000 copies/mL |
| 4 | 400mM | 1mM | 8.0 | 75mM | 20,000 copies/mL |
| 5 | 400mM | 4mM | 8.0 | 0 | 20,000 copies/mL |
| 6 | 400mM | 4mM | 8.0 | 75mM | 20,000 copies/mL |

FIG. 21B

| Row | | | | | | | | | | | | | | | | | Score |
|---|---|---|---|---|---|---|---|---|---|---|---|---|---|---|---|---|---|
| 1 | N/A | 41.02 | 34.89 | 36.86 | 35.86 | 33.4 | N/A | 79.62 | 43.19 | 34.44 | 36.88 | 42.42 | 35 | 39.25 | 33.67 | 80.38 | 76.32 | N/A | 35.81 | 71.95 | 8/16 50% |
| 2 | 41.66 | 38.02 | 33.6 | 38.49 | N/A | 34.03 | 35.8 | 46.58 | 39.75 | N/A | N/A | 40.31 | 44.23 | 32.53 | 33.97 | 13/16 81.3% |
| 3 | 34.11 | 45.22 | 32.81 | 61.97 | 35.92 | 80.23 | 34.22 | 33.9 | 46.31 | 32.06 | 33.29 | 39.88 | 43.99 | 32.92 | 36.63 | 14/16 87.5% |
| 4 | 36.32 | 43.02 | 32.49 | 34.5 | 39.41 | 34.94 | 34.45 | 34.3 | 71.84 | 64.73 | 48 | 44.56 | 49.43 | 34.72 | 39.43 | 14/16 87.5% |
| 5 | 37.15 | 38.56 | 43.31 | 35.84 | 33.56 | 89.48 | 49.21 | 36.11 | 43.19 | 50.41 | 39.18 | 39.14 | 37.67 | 37.11 | N/A | 14/15 93.3% |
| 6 | 35.58 | 38.27 | 35.3 | 32.7 | 34.81 | 37.9 | 35.73 | 38.68 | 40.16 | 44.5 | 40.51 | 46.89 | 44.35 | 32.23 | N/A | 15/15 100% |

432nm yellow

560nm red

Ratio 432/560 = low — no/low amplification

High amplification = high

RAPID DIAGNOSTIC TEST USING COLORIMETRIC LAMP

CROSS-REFERENCE

This application claims right of priority to U.S. Provisional Application No. 62/988,696, filed Mar. 12, 2020; U.S. Provisional Application No. 63/001,909, filed Mar. 30, 2020; U.S. Provisional Application No. 63/013,442, filed Apr. 21, 2020; U.S. Provisional Application No. 63/022,303, filed May 8, 2020; U.S. Provisional Application No. 63/027,216, filed May 19, 2020; U.S. Provisional Application No. 63/048,556, filed Jul. 6, 2020 and is a continuation of U.S. application Ser. No. 16/938,575, filed Jul. 24, 2020. The contents of these applications are incorporated herein by reference in their entirety.

BACKGROUND

The ability to detect an infectious agent in a widespread epidemic is a critical aspect of successful quarantine efforts and enables screening of potential cases of infection from patients in a clinical setting. Enabling testing outside of sophisticated laboratories broadens the scope of control and surveillance efforts, but also requires robust and simple methods that can be used without expensive instrumentation. The emergence of a new Coronavirus (2019-nCoV, also called SARS-CoV-2 and SARS-CoV-2 and COVID-19) has caused a world-wide pandemic for which diagnostic tests play a critical role. The current diagnostic standard combines clinical symptoms and molecular method, where symptoms for some patients range from life threatening to resembling those of common cold and influenza, to no symptoms or widely variable symptoms. Monitoring the spread of infection requires accurate, easy to use, widely available and cost sensitive molecular diagnostic tests. These molecular methods include metagenomics sequencing mNGS and RT-qPCR (Huang, et al. (2020) Lancet, 395, 497-506). mNGS is restricted by throughput, turnover time, high costs and requirement for high technical expertise. Reverse transcriptase-quantitative PCR (RT-qPCR) requires multiple steps and expensive laboratory instruments and is difficult to utilize outside of well-equipped facilities. A rapid, specific, and sensitive diagnostic single test for one or several pathogens would be desirable to identify and track infected humans, animals or plants in a widespread epidemic that might threaten health and well-being.

SUMMARY

In one aspect, there is provided a master mix comprising: a DNA polymerase suitable for isothermal amplification of DNA; dNTPs (dATP, dGTP, dCTP, and dTTP); and at least one dye that changes color or fluorescence in response to DNA amplification. The master mix may be dried or may be in a weakly buffered solution. In many embodiments, the master mix is a Loop-Mediated Isothermal Amplification (LAMP) master mix. However, the parameters tested herein may be applicable to master mixes for non-LAMP isothermal amplification reactions.

The DNA polymerase in the master mix may be any polymerase suitable for use in an isothermal amplification reaction (e.g. in a LAMP reaction). Suitable DNA polymerases are known in the art and include strand displacing DNA polymerases preferably mesophilic DNA polymerases such as Bst polymerase or variants thereof or Bsu DNA polymerase or variants thereof.

The at least one dye may be a colored dye detectable in visible light, or may be a fluorescent dye, so long as the dye provides a change in signal (e.g. a change in color, or a change in color intensity or fluorescence intensity) in response to an amplification reaction.

In one embodiment, the at least one colorimetric or fluorescent dye is or includes a dye that is pH sensitive. When the master mix containing the dye is used in an amplification reaction that alters the pH of the reaction mix, the spectral or fluorescent properties of the dye change (e.g. the dye changes color), which provides confirmation that amplification has occurred. Examples of pH sensitive dyes include colorimetric dyes such as phenol red, cresol red, m-cresol purple, bromocresol purple, neutral red, phenolphthalein, naphtholphthaein, and thymol blue; and fluorescent dyes such as 2',7'-Bis-(2-Carboxyethyl)-5-(and-6)-Carboxyfluorescein or a carboxyl seminaphthorhodafluor (e.g. SNARF-1). In one embodiment, the at least one pH sensitive dye is phenol red.

In one embodiment, the at least one dye is or includes a dye that is not pH sensitive, such as a metallochromic indicator. When the master mx containing the metallochromic indicator dye is used in an amplification reaction that alters the availability of one or more metal ions in the reaction mix, the spectral or fluorescent properties of the dye change (e.g. the dye changes color), which provides confirmation that amplification has occurred. In one embodiment, the metallochromic indicator dye is 4-(2-pyridylazo) resorcinol (PAR). If PAR is used, the master mix may additionally comprise manganese ions such that the PAR in the master mix is complexed with Mn ions to form a PAR-Mn complex. Another example of a metallochromic dye is hydroxynaphthol blue (Wastling et al. (2010) PLoS Negl Trop Dis 4(11): e865. doi: 10.1371/journal.pntd.0000865).

In a preferred embodiment, the visually detectable dye in the reaction mix (1× master mix combined with sample) is in the range of 50 μM-200 μM.

The master mix for LAMP may optionally further comprise at least one set of primers (e.g. two, three, four, or five sets of primers) having specificity for a template region in a target nucleic acid. If multiple primer sets are used, each primer set may target a different nucleic acid sequence within the target nucleic acid (e.g. two or more different viral gene sequences). For example, the master mix may comprise at least two sets of primers, each specific for a different SARS-Cov-2 target sequence (e.g. in the ORF 1a gene and/or Gene N of SARS-Cov-2). Frequently it is preferred that the primers are provided separately from the master mix.

The master mix may comprise a reverse transcriptase, such as an HIV derived reverse transcriptase, an intron encoded reverse transcriptase, or a reverse transcriptase variant of Moloney murine leukemia virus. The master mix may comprise one or more aptamers for regulating the activity of the polymerase and/or the reverse transcriptase as well as one or more aptamers for inhibiting RNase activity, such as an aptamer for inhibiting RNase A and an aptamer for inhibiting RNase I. The master mix may include an RNAse inhibitor that is not an aptamer. The master mix may comprise dUTP and/or a uridine deglycosylase (UDG), such as a thermolabile UDG.

In one embodiment, the master mix optionally comprises a molecule comprising C—(NH$_2$)$_2$NH; such as guanidine hydrochloride, guanidine thiocyanate, guanidine chloride, guanidine sulfate, or arginine. In one embodiment, the master mix comprises guanidine hydrochloride. The C—(NH$_2$)$_2$NH containing molecule can be present in the master mix at a concentration in the range of up to 60 mM, such as in the range of 20 mM-40 mM (e.g. about 20 mM, 30 mM or 40 mM).

However, in certain embodiments, the master mix does not contain a molecule comprising C—(NH$_2$)$_2$NH. In these circumstances, a composition comprising C—(NH$_2$)$_2$NH; such as guanidine hydrochloride, guanidine thiocyanate, guanidine chloride, guanidine sulfate, or arginine is not included in the master mix may be provided separately such as contained in a lysis buffer or in a mixture containing primer sets for adding to a LAMP reaction mixture. In one embodiment, a concentration of guanidine salt in the LAMP reaction mixture is preferably 40 mM guanidine salt. The C—(NH$_2$)$_2$NH containing molecule can be present in the composition at a concentration in the range of up to 60 mM, such as in the range of 20 mM-40 mM (e.g. about 20 mM, 30 mM or 40 mM). In certain embodiments, the master mix contains sets of primers that are specific for target regions in a polynucleotide. In other embodiments, the master mix does not contain primers where these are added separately.

In embodiments where the master mix is dried, the master mix may be freeze dried, air dried, or lyophilized. The master mix may be immobilized, for example on paper, or on a natural or synthetic polymer. The dried master mix is reconstituted prior to use in an amplification reaction.

In embodiments where the master mix is in solution (e.g. following reconstitution), the master mix is in a weakly buffered solution, such as in a Tris buffer. The weakly buffered solution preferably has a concentration less than 5 mM, such as less than 5 mM Tris or equivalent buffer. In one embodiment, the weakly buffered solution is in the range of 0.5 mM to 5 mM, such as 0.5 mM to 5 mM Tris or equivalent buffer. The pH of the master mix may be buffered in the range of pH 7.5-pH 9.0; such as in the range of pH 7.8-pH 8.5, or pH 8.1-pH 8.5. The liquid form of the master mix may be in any suitable reaction container.

In one aspect there is provided a kit comprising a master mix as described herein. The kit may optionally further comprise a heating block or water bath suitable for heating a reaction tube, plate, or paper, or a plurality of the same to a temperature suitable for isothermal amplification.

In one aspect there is provided a method for determining whether a target nucleic acid is present in a sample, comprising: bringing an aliquot of the sample into contact with a master mix as described herein to form a reaction mixture wherein the reaction mix additionally includes sets of primers that are specific for the target nucleic acid. In one example, the sample may be in an aqueous solution or absorbed to a test matrix such as paper. The master mix may include additional reagents to enhance sensitivity of the assay such as a guanidine salt, or this could be added separately to the reaction. Additionally, for LAMP, one primer set or a plurality of primer sets may be included in the master mix or added separately to the reaction mix. Not all target specific primer sets work equally well. For improved sensitivity, it is desirable to test a number of primer sets to select one or a combination of primer sets to maximize sensitivity of the LAMP assay. Determination as to whether the target nucleic acid is present in the sample may then proceed by detecting a change in the spectral properties, color, or fluorescence of the reaction mixture.

In one embodiment, the method involves isothermal amplification of the target nucleic acid in a LAMP reaction or a helicase-dependent amplification reaction (HDA). In one embodiment, the method involves colorimetric LAMP, which may be pH sensitive or may be pH insensitive (e.g. using PAR). In one embodiment, the method uses two, three, four, or five sets of target-specific primers in a multiplexed reaction (e.g. multiplexed LAMP); wherein the primers are added to the reaction mixture in the master mix or are added separately.

The sample may be a clinical sample, such as a sample of a body fluid (e.g. blood, sputum, saliva, mucous, lymph, sweat, urine, feces, etc.) or a sample taken from a swab such as a nasal, oral, or buccal swab, which may be from a human or other mammalian subject. The sample may alternatively be an environmental sample. In some embodiments, the method is performed directly on the sample (e.g. crude tissue or cell lysate, or whole blood) without a step of purifying target nucleic acid from the sample. To facilitate this, the sample may be added to a lysis buffer such as exemplified herein for saliva that may nonetheless be suitable for any body fluid. The sample may alternatively be a sample of purified nucleic acid.

Where an aqueous solution is referred to without reference to a body fluid or environmental sample, it may include sterile water or a weak buffer (e.g. 0.5 mM to 5 mM, such as 0.5 mM to 5 mM Tris or equivalent buffer) where the aqueous solution optionally containing an RNase inhibitor or inhibitors.

The target nucleic acid may be any DNA or RNA of interest. For example, the nucleic acid may be associated with a pathogen or a diagnostic target for pathogenesis. In one embodiment, the target nucleic acid is RNA or DNA of a target pathogen. In one embodiment, the target nucleic acid is from a bacterium. In one embodiment, the target nucleic acid is from a multi-cellular parasite, such as a parasitic nematode. In one embodiment, the pathogen is a virus; for example, an RNA virus, such as a coronavirus. For example, the pathogen may be SARs-CoV-2. In one embodiment, the target SARs-CoV-2 RNA sequence is the ORF1a gene and/or Gene N or portion thereof. Thus, there is provided a method for determining whether a SARs-CoV-2 nucleic acid is present in a sample, comprising: bringing an aliquot of the sample in an aqueous solution into contact with a master mix as described herein to form a reaction mixture, wherein the master mix or reaction mixture comprises at least one set of primers specific for a target SARs-CoV-2 nucleic acid; and determining whether the target SARs-CoV-2 nucleic acid is present in the sample by detecting a change in the color or fluorescence of the mixture.

In one embodiment, the nucleic acid is associated with gene expression, or may be an indicator of a metabolic response to a pharmaceutical preparation or allergen. For example, the method may be for determining a gene expression profile in response to an environmental or metabolic event, or in response to a therapeutic treatment. In one embodiment, the target nucleic acid is DNA, and the method is for determining one or more genetic loci correlated to a phenotype. For example, the genetic loci may be selected from the group consisting of a single nucleotide polymorphism (SNP) in a genome, an exon, or a gene in a genome. These methods may be useful in diagnosis of a genetic disease or in personalized medicine.

In one embodiment, the method uses a pH-sensitive dye. During nucleic acid amplification, hydrogen ions accumulate in the reaction mixture so that the mixture becomes increasingly acidic with increasing amplification. pH sensitive dyes change their color, color intensity, or fluorescent intensity, in response to the change in pH in the reaction mixture.

In one embodiment, the method uses PAR as the dye, and the master mix or the reaction mixture further comprises manganese ions (e.g. about 0.4 mM Mn ions per 100 µM PAR). The complex of PAR with manganese ions is in a red-colored state. Pyrophosphate produced during the nucleic acid amplification process, as a byproduct of primer nucleic acid polymerization, sequesters manganese with a higher affinity than does PAR, thereby removing the manganese from solution and returning PAR to a non-complexed, yellow-colored state. In one embodiment, the reaction mixture further comprises a non-ionic detergent such as Triton X-100 (e.g. at about 1%-4%, such as about 1% or 2%), which is shown herein to further enhance the color-change observed when using PAR.

The concentration of the visually detectable dye in the reaction mix may be in the range of 50 µM-250 µM; such as at 50 µM-150 µM, for example at about 50 µM, 75 µM, 100 µM, or 150 µM.

In one embodiment, the reaction mixture further comprises a molecule comprising C—$(NH_2)_2$NH; such as guanidine hydrochloride, guanidine thiocyanate, guanidine chloride, guanidine sulfate, or arginine. In one embodiment, the molecule is guanidine hydrochloride. The C—$(NH_2)_2$NH containing molecule can be added to the reaction at a concentration of up to 60 mM, such as in the range of 20 mM-40 mM (e.g. about 20 mM, 30 mM, or 40 mM). If the method uses a C—$(NH_2)_2$NH containing molecule (e.g. guanidine hydrochloride), the sodium chloride concentration in the reaction mixture is preferably less than 40 mM; for example, the reaction mixture may contain NaCl at a concentration of about 20 mM or about 10 mM. The reaction mixture may alternatively, or additionally, comprise KCl at a concentration of less than 100 mM (e.g. less than 40 mM).

The method may comprise the step of combining one or more RNase inhibitors and/or thermolabile Proteinase K with the sample, prior to combining the sample with the master mix to form the reaction mixture. Alternatively, one or more RNase inhibitors and/or thermolabile Proteinase K can be added to the reaction mixture together with the sample, in which case the thermolabile Proteinase K should be inactivated prior to adding the master mix. The method may comprise adding a reverse transcriptase to the reaction mixture (either via the master mix, or separately) if the target nucleic acid is RNA, such as viral RNA. The reaction mixture may further comprise dUTP and UDG (e.g. thermolabile UDG), which may be added to the reaction mixture from the master mix. Alternatively, the dUTP may be added to the reaction mixture from the master mix, and the UDG may be added separately to the reaction mixture.

In one embodiment, the method comprises analyzing multiple samples. For example, the method may use a reaction container that has multiple compartments each for analyzing a separate sample.

In one embodiment of the method, the master mix is dried and immobilized onto e.g. paper, and an aliquot (e.g. droplet) of the sample is added to the paper, followed by a heating step, resulting in amplification of target nucleic acid in the sample.

The change in the spectral or fluorescent properties of the dye can be detected by eye or using a spectrophotometer or fluorimeter or recorded by means of a camera or other color sensitive recording device. In one embodiment, the method involves comparing the spectral or fluorescent properties of the dye before and after amplification has occurred. In one embodiment, the change in spectral properties or fluorescence of the mixture can be recorded by a spectrophotometer having dual wavelength capabilities, digitized, and stored by a computer.

In one aspect, there is provided a composition, comprising: one or more primer sets suitable for amplification, such as for an isothermal amplification reaction such LAMP, the primer sets having specificity for a single target nucleic acid of interest; and a buffer containing a molecule comprising C—$(NH_2)_2$NH.

In one embodiment, the composition comprises two, three, four, or five primer sets, each having specificity for a single target nucleic acid of interest; such as a viral RNA sequence (e.g. SARs-CoV-2 RNA).

In one embodiment, the composition comprises C—$(NH_2)_2$NH such as selected from guanidine hydrochloride, guanidine thiocyanate, guanidine chloride, guanidine sulfate, or arginine. In one embodiment, the molecule is present in the composition at a concentration in the range of up to 60 mM, such as in the range of 20 mM-40 mM (e.g. about 20 mM, 30 mM, or 40 mM).

The composition may further comprise one or more reagents selected from a DNA polymerase, such as Bst polymerase; a reverse transcriptase; and an RNAse inhibitor. The composition may comprise dNTPs, which may optionally include dUTP; and/or may comprise a thermolabile UDG. The composition may further comprise a reporter molecule for detecting amplification in the presence of a target nucleic acid; for example, a colorimetric or fluorescent dye as described herein (e.g. PAR).

In one aspect there is provided a method of isothermal amplification (e.g. LAMP or HDA), comprising: (a) adding any embodiment of the master mix described herein that contains a suitable polymerase, and dNTPs to a sample comprising a target nucleic acid to form a reaction mixture, and in the presence of suitable primers allowing amplification to occur; and (b) detecting whether the target nucleic acid is present in the sample.

The target nucleic acid may be as described above. In one embodiment, the target nucleic acid is a viral nucleic acid such as viral RNA. For example, the target nucleic acid may be a SARs-CoV-2 RNA. In one embodiment, the target SARs-CoV-2 RNA sequence is located within the ORF1a gene and/or Gene N.

In one embodiment, the molecule comprising C—$(NH_2)_2$NH (e.g. guanidine hydrochloride also referred to as guanidinium chloride, guanidine thiocyanate, guanidine chloride, guanidine sulfate, or arginine) is present in the reaction mixture at a concentration of 10 mM-250 mM, 20 mM-10 mM, 30 mM-80 mM, up to 75 mM or 60 mM, such as in the range of 20 mM-75 mM, for example, 20 mM-60 mM (e.g. about 20 mM, 30 mM, 40 mM or 50 mM). In one embodiment, the reaction mixture may further comprise NaCl at a concentration of less than 40 mM; such as at a concentration of about 20 mM. The reaction mixture may alternatively, or additionally, comprise KCl at a concentration of less than 100 mM (e.g. less than 40 mM).

In one aspect there is provided a method for detecting amplification of a target nucleic acid, comprising: providing an amplification reaction mixture containing a target nucleic acid and a master mix or composition as defined herein; and detecting a change in the spectral or fluorescent properties of the dye resulting from amplification of the target nucleic acid. The target nucleic acid may be as described above. In one embodiment, the target nucleic acid is a viral nucleic acid such as viral RNA. For example, the target nucleic acid may be a SARs-CoV-2 RNA.

In one embodiment, a kit is provided for performing multiplex LAMP reaction. The kit includes a plurality of sets of oligonucleotide primers wherein each set of primers hybridize to a different template sequence in a nucleic acid target, where the plurality of sets of polynucleotide primers are suitable for amplifying the different template sequences of the nucleic acid target by LAMP. The kit further includes a strand displacing polymerase and a guanidinium salt. The guanidinium salt is provided in a separate container from the oligonucleotide primers and the strand displacing polymerase. Optionally, the oligonucleotide primers and strand displacing polymerase are also in separate containers where the contents of these three containers are suitable for combining together in a reaction mixture containing a sample nucleic acid for performing the amplification reaction. Optionally, each set of the plurality of sets of oligonucleotide primers are in a separate container for combining in a reaction mix. The kit may further include instructions describing how to combine the reagents in the kit with the sample to form a reaction mix for detecting a nucleic acid target in the sample by amplification of the different template regions by LAMP.

The kit may include a plurality of oligonucleotide primers for targeting template sequences in a Coronavirus. If the Coronavirus is the nucleic acid target then the kit preferably includes a reverse transcriptase to produce cDNA for LAMP. The kit may also include one or more sets of oligonucleotide primers that target nucleic acids from a plurality of pathogens such as a plurality of viruses, where the plurality of viruses include influenza virus and coronavirus. In this example, the kit may provide in a pool or separately, a plurality of sets of oligonucleotide primers for detecting in a sample, both coronavirus RNA and influenza RNA. The kit may contain a plurality of sets of oligonucleotide primers to target template sequences in a eukaryotic genome or prokaryotic genome for detecting a mutation in the genome.

A benefit of the use of a plurality of sets of oligonucleotide primers to detect a nucleic acid target using LAMP is increased sensitivity. "Increased sensitivity" refers to determining the presence of fewer target nucleic acids than would be possible without the specified feature, where all other conditions being substantially the same. Increased sensitivity is important, for example, when detecting a viral genome in a host or environmental sample where the number of virus genomes may be low. Using the Coronavirus genome as an example, a plurality of sets of oligonucleotide primers have been shown here to increase sensitivity of a LAMP reaction compared with using a single set of oligonucleotide primers. Guanidinium salts, for example, guanadinium chloride enhance the sensitivity of the amplification reaction.

A set of oligonucleotide primers for use in performing a multiplex LAMP reaction may be 4, 5 or 6 primers, for example, 5 or 6 primers. The kit may include a mixture in a single container of a plurality of sets of primers for targeting multiple template sequences in a single target nucleic acid. The plurality of sets of primers may include single or multiple sets of oligonucleotide primers that target template sequences in a plurality of target nucleic acids and/or a plurality of different samples.

Alternatively, the plurality of sets of oligonucleotide primers for each nucleic acid target may be in separate containers although these different plurality of sets of oligonucleotide primers may be combined in a reaction mixture containing a nucleic acid containing sample.

In one embodiment of the kit, the strand displacing polymerase is contained in a master mix. The master mix may be in a buffer or may be lyophilized. The master mix may be concentrated so that when added to the template, the components in the master mix are in the appropriate amounts in the reaction mix. For example, the master mix may be a 2× concentration so that equal volumes of master mix are added to the sample after calculating for the volume of oligonucleotide primers and guanidinium salt. In certain embodiments, the master mix includes 4 or 5 deoxynucleoside triphosphates selected from dUTP, dGTP, dCTP, dGTP and dATP. The master mix may include at least one indicator for detecting an amplification product by a change in color or fluorescence. The master mix may further include one or more of the following: a reverse transcriptase, a uracil deglycosylase such as a thermolabile uracil deglycosylase, a Proteinase K such as a thermolabile Proteinase K, a reducing agent such as Tris(2-carboxyethyl)phosphine hydrochloride (TCEP), a non-ionic detergent, lithium chloride (LiCl), one or more reversible inhibitors of reverse transcriptase and/or polymerase, as well as non-reversible inhibitors of RNAse. A reversible inhibitor of an enzyme is capable of blocking enzyme activity below a desired temperature such as 45° C. or 40° C. to avoid undesirable background amplification resulting from copying primers rather than template. Other molecules for reducing background include helicases and single strand binding proteins. Examples of reversible enzyme inhibitors include aptamers or proteins such as antibodies or portions of antibodies.

In one embodiment of the kit, an indicator is included that signals a color change or a fluorescence or chemiluminescence signal when LAMP has occurred. Preferably this signal is detectable by eye or by use of an instrument. Examples of suitable indicators include an optically detectable dye such as a pH sensitive color dye, a metallochromic dye, an intercalating molecule fused or linked via a linker group to an optically detectable dye moiety, a fluorescent reporter dye.

In one embodiment of the kit, the guanidinium salt is guanidinium chloride. The instructions with the kit, inform the user that guanidine salt should be present in the reaction mix either because it was introduced from the preparation provided in the present kit or was carried over from a previous step such that the final concentration of the guanidinium salt in the reaction mix that includes kit components is for example in the range of 20 mM-40 mM for guanidinium chloride or corresponding amount for a different guanidiunium salt for increasing the speed and sensitivity of the LAMP reaction.

In one embodiment of the kit, if the guanidiunium salt is guandinium chloride and the guanidinium chloride is at 10× then the guanidinium chloride concentration in the range of 200 mM-600 mM.

In one embodiment, a method is provided that includes the steps of (a) combining the kit described above that contains a plurality of sets of oligonucleotide primers, a strand displacing polymerase and a guanidinium salt, with at least one nucleic acid target to produce a reaction mix; and (b) incubating the reaction mix to produce an amplification product.

The at least one target nucleic acid may be a purified nucleic acid, a nucleic acid within a biological fluid or a nucleic acid preparation released from a sample swab or from a lysed cell sample into an aqueous fluid. The target nucleic acid may be obtained from a human subject or from an environmental sample. In one example, the at least one target nucleic acid is a coronavirus or a coronavirus and an influenza virus.

An embodiment of the method described herein may include an additional step (c) of detecting the amplification product. Any of (a)-(c) may be partially or completely automated.

In one embodiment of the method, detecting the amplification product may involve a change in color or fluorescence, so that detecting amplification may be achieved by visualizing a color change by eye, measuring a change of color by means of a spectrophotometer or measuring fluorescence with a fluorescence spectrometer.

The kit used in the method may include at least one additional reagent selected from the group consisting of: a reverse transcriptase, UDG, dUTP, dATP, dTTP, dGTP, dCTP, an indicator that changes color or fluorescence when amplification has occurred, lithium chloride, a detergent and a reducing agent. The kit preferably contains a reverse transcriptase if at least one of the target nucleic acid is RNA, and the method comprises reverse transcribing the RNA into DNA.

The kit used in the method may include a plurality of sets of oligonucleotide primers in the kit for hybridizing to different template sequences in the same nucleic acid target. Examples of the nucleic acid targets are pathogens or a gene locus or chromosome. Where the nucleic acid target is a pathogen, it may be an RNA virus or cDNA copy thereof. Examples of RNA viruses include coronavirus and influenza virus.

The method may include pooling a first plurality of sets of oligonucleotide primers for a first nucleic acid target and a second plurality of sets of oligonucleotides for a second nucleic acid target and combining the pooled oligonucleotide primers with the strand displacing polymerase and guanidine salt and one or more nucleic acid samples for detecting the amplification products of the first and second nucleic acid targets in the one or more nucleic acid samples.

The method may include detecting a plurality of the same or different nucleic acid targets from the same or different individual sources in a multiplex reaction wherein two or more sets of oligonucleotide primers hybridize to template sequences in each of the plurality of nucleic acid targets. In one embodiment at least one primer in each oligonucleotide primer set contains a sample barcode to identify the sample source of the nucleic acid target.

BRIEF DESCRIPTION OF THE FIGURES

The patent or application file contains at least one drawing executed in color. Copies of this patent or patent application publication with color drawings will be provided by the office upon request and payment of the necessary fee.

FIG. 3A shows direct RNA LAMP detection using total cell lysate. The approximate maximum number of copies of synthetic RNA added to each LAMP reaction is shown. The viral RNA was spiked into a Hela cell lysate. For 4800 copies of viral RNA, there were about 200 Hela cells present. NC, no cell, and no template control.

FIG. 3B shows colorimetric LAMP detection of various amounts of target RNA spiked in whole blood. The number of copies of the target RNA that could be detected are shown. In a control, 5 ng of Jurkat total RNA was added, which is similar to the total RNA present in the reaction with blood samples.

FIG. 4A-FIG. 4B shows the detection of various closely related nematode parasites was achieved for as little as 0.01 pg of nematode DNA in an environmental sample using the colorimetric LAMP described in Example 1. The control was a reagent mix absent nematode sample. Although Example 1 describes the test for an RNA virus, the same methodology applies to detecting the DNA from the various nematodes using an appropriate set of primers. As indicated in the figure, the assay could detect 0.01 pg-0.1 pg of nematode parasite DNA.

FIG. 5A-FIG. 5B shows that pH colorimetric LAMP is a useful diagnostic tool for detecting tick borne pathogens as it is both sensitive and specific for the target.

FIG. 5A shows detection of 1.28 fg target DNA from a specific target tick borne pathogen, with negative results (pink) from samples of non-target tick borne pathogens and hosts.

FIG. 5B shows specificity for the target DNA with negative (pink) results for non-target DNA. 1) no template DNA control; 2) pathogen target DNA; 3) DNA from other tick-borne pathogen 1 (negative control); 4) DNA from other tick-borne pathogen 2 (negative control); 5) DNA from other tick-borne pathogen 3 (negative control); 6) tick DNA; 7) mosquito DNA; 8) DNA from other tick-borne pathogen 4 (negative control).

FIG. 8A-FIG. 8C shows real time detection of target RNA (Jurkat total RNA) using a lyophilized LAMP MM and an HMBS2 primer set and a −20° C. storage preparation of LAMP MM. The LAMP MM contained the fluorescent dye (SYTO® 9, Molecular Probes, Eugene, Oreg.) for following amplification. FIG. 8D provides a comparison of the rate of LAMP using a previously lyophilized LAMP MM or a MM stored at −20° C.

FIG. 9A and FIG. 9B showed a color change with phenol red while FIG. 9C used a fluorescent dye to detect amplification. WarmStart LAMP Kit (DNA & RNA) is provided New England Biolabs, Ipswich, Mass.

Figures 11A, 11B:
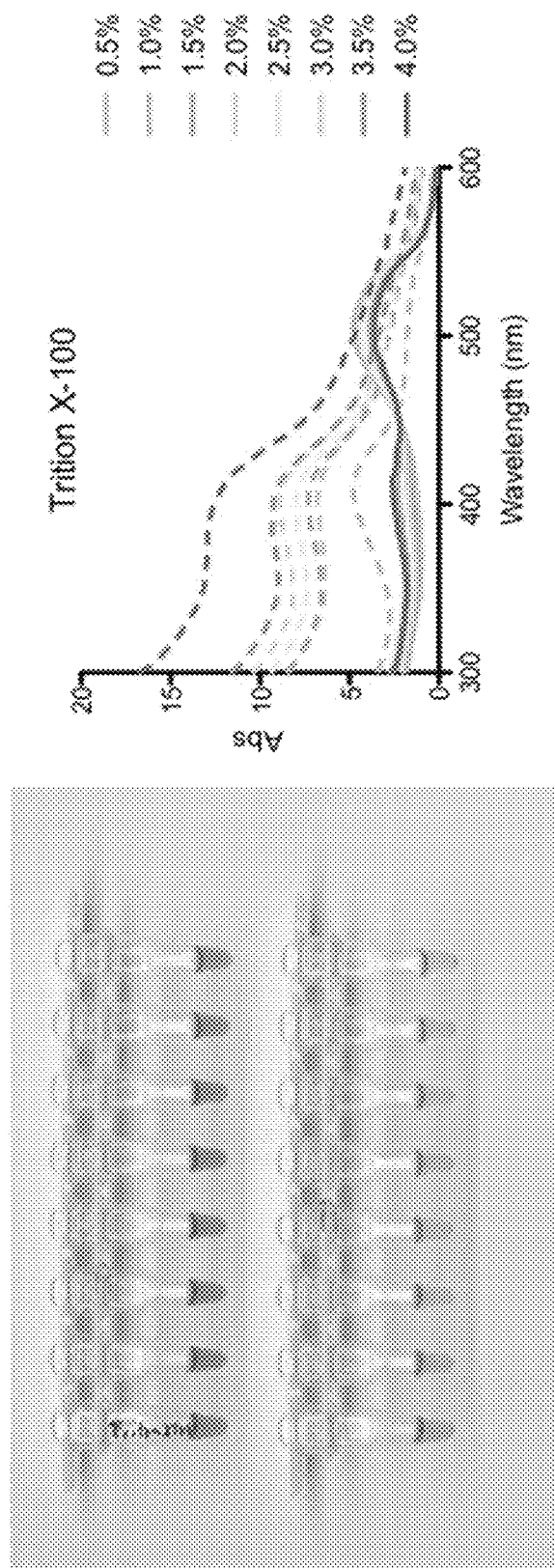
FIG. 11A and FIG. 11B shows that because pyrophosphate exhibits a higher affinity for manganese ions than PAR, this property can be used to detect amplification of nucleic acids using LAMP. Pyrophosphate generated during nucleic acid polymerization precipitates manganese from solution, thus disrupting the PAR:Mn complex and restoring the yellow color. This is demonstrated spectroscopically by spiking in pyrophosphate to restore the yellow color (bottom row) (FIG. 11A).

The color change can be further enhanced by the addition of Triton X-100 (FIG. 11B).

Figure 12:
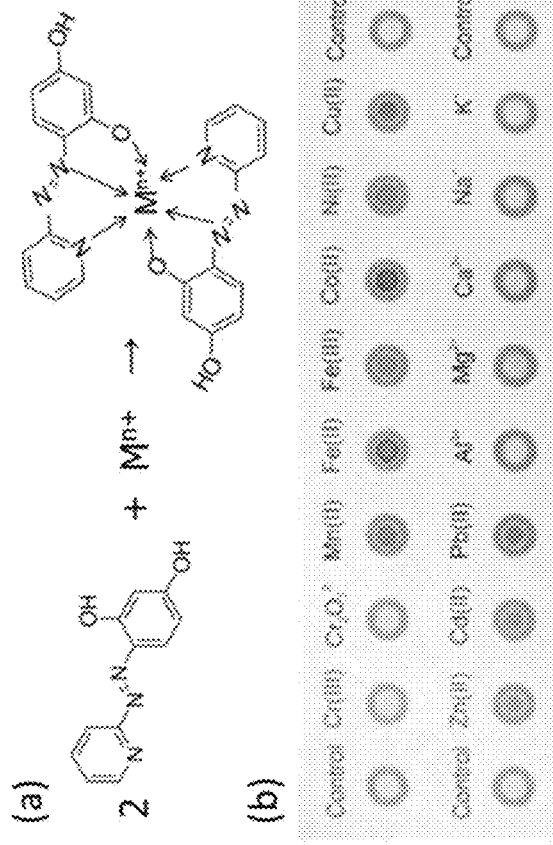

FIG. 12 shows that PAR has been demonstrated to be compatible with use in microfluidic paper-based analytical devices (μPADs) (Meredith, et al. Anal. Methods (2017) 9, 534-540). (b) shows the results of a paper-based spot test showing metal-PAR reactivity (orange and red color formation) for a number of transition, alkali, and alkaline earth metals.

Figure 13:
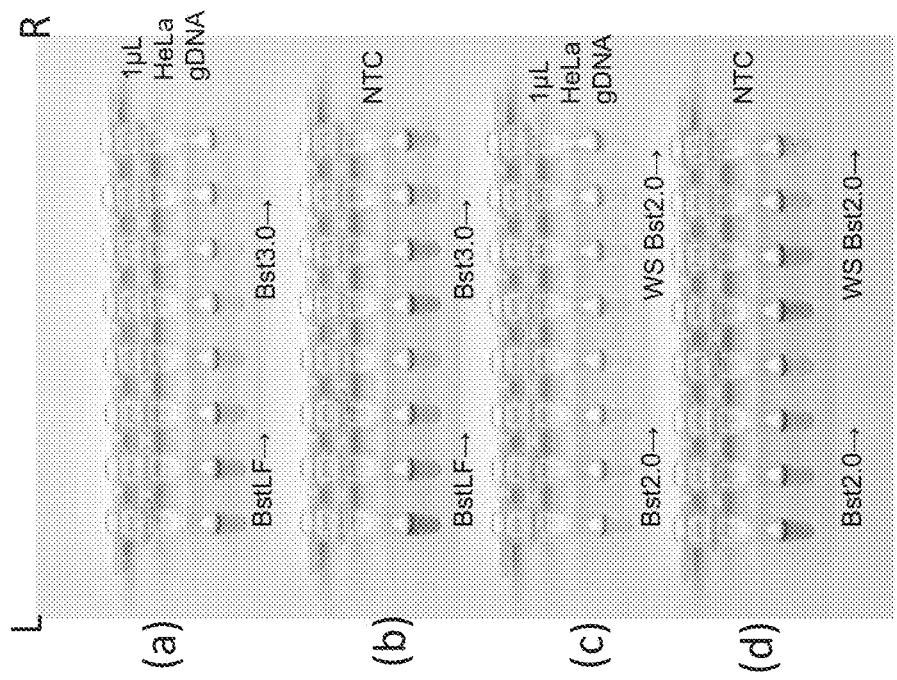

FIG. 13 shows that PAR provides the means of a colorimetric endpoint for LAMP in a LAMP MM. A color change is observed when precipitation of manganese occurs that is caused by the release of pyrophosphates in a LAMP reaction. The enzymes added to perform LAMP in the presence of resorcinol and conditions of the reaction are as follows:

(a) DNA polymerase Bst LF: (M0275) in 1× ThermoPol® added to 1 μl of Hela Cell gDNA; (b) Bst 3.0: (M0374) in 1× Isothermal Amplification Buffer II absent gDNA; (c) Bst 2.0: (M0537) in 1× Isothermal Amplification Buffer plus 1 μg gDNA; and (d) WarmStart Bst 2.0: (M0538) in 1× Isothermal Amplification Buffer (New England Biolabs, Ipswich, Mass.);

PAR concentrations left to right: 150 μM, 100 μM, 75 μM, 50 μM;

$Mn^{2+}$ concentration: 0.5 mM $MnCl_2$;

LAMP Reaction Incubation: 65° C. for 1 hour;

LAMP Primer Set: BRCA2b FIP/BIP/F3/B3/LF/LB;

Target polynucleotide is the BRCA gene in Hela cell genomic DNA.

The non-template control retains the red color of PAR bound to manganese ions while the positive sample turned yellow corresponding to the reaction of manganese with pyrophosphate.

Figure 14:
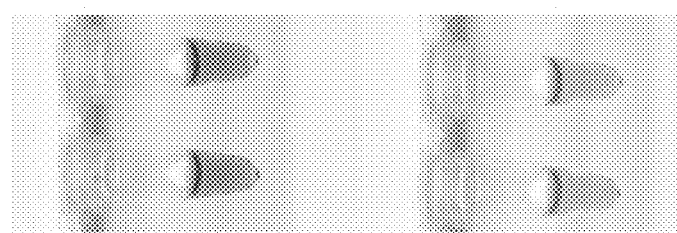

FIG. 14 shows the strong color reaction of a PAR-based LAMP in the presence of 2% Triton X-100 and 0.5 mM $MnCl_2$, Bst 2.0 polymerase, 1× Isothermal Amplification Buffer, 200 μM PAR and the BRCA2b primer set using 1 μl Hela cells. The non-template control retains the red color of PAR bound to manganese ions while the positive sample turned yellow corresponding to the reaction of manganese with pyrophosphate.

FIG. 15 shows examples of 4 different guanidine salts (also called guanidinium salts) for enhancing the LAMP reaction.

Figure 16:
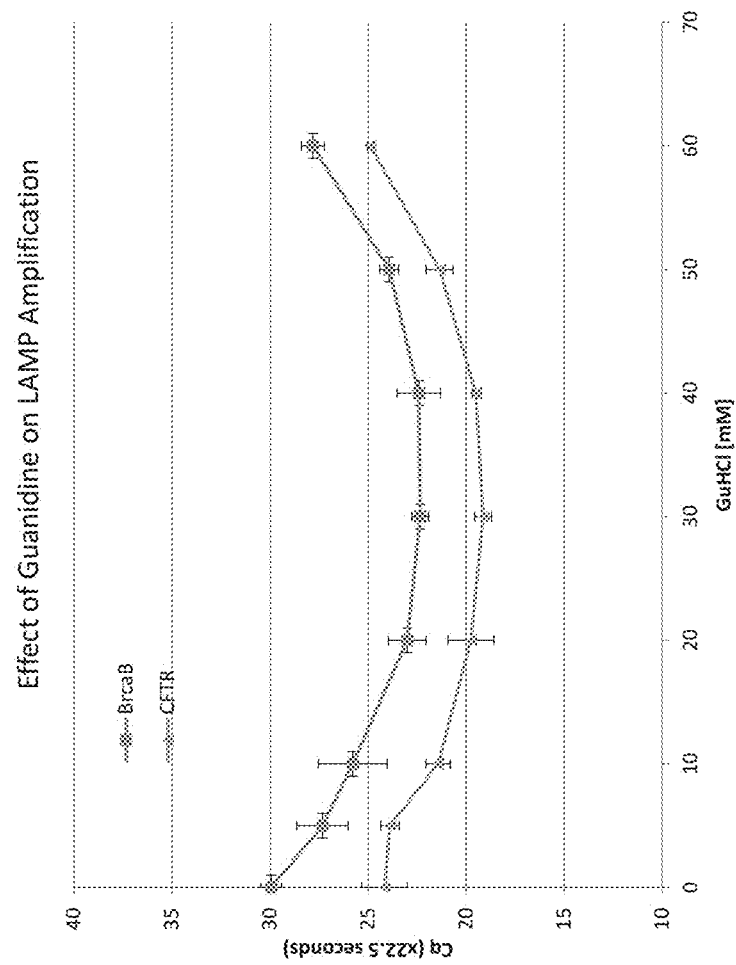

FIG. 16 shows that guanidine hydrochloride (GuCl) increases the reaction speed of a LAMP amplification reaction. Detection of two different genes-BRACA and CFTR were achieved using LAMP MM and increasing concentrations of GuCl.

Figure 17A:
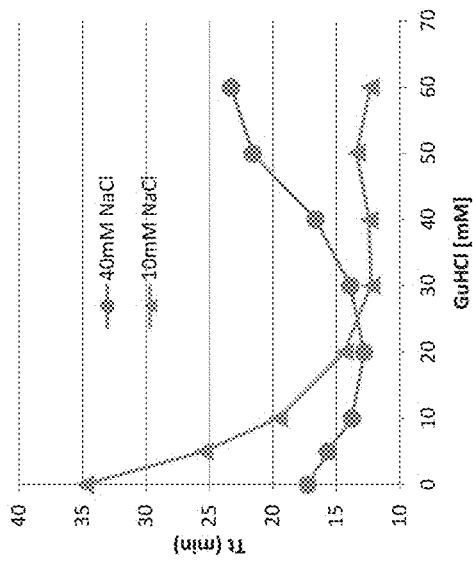
Figure 17B:
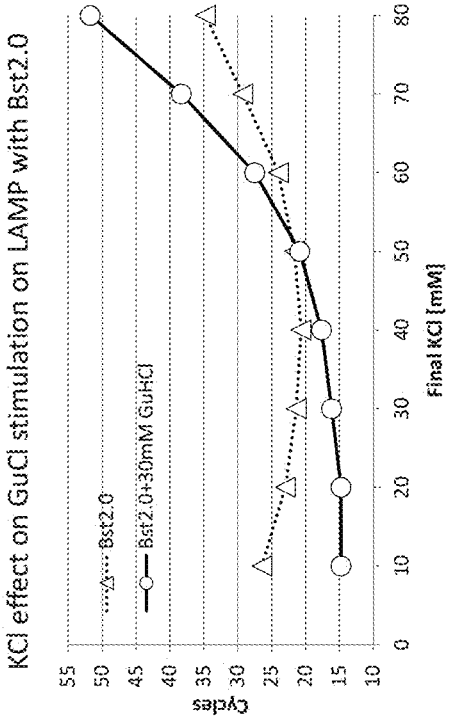
Figure 17C:
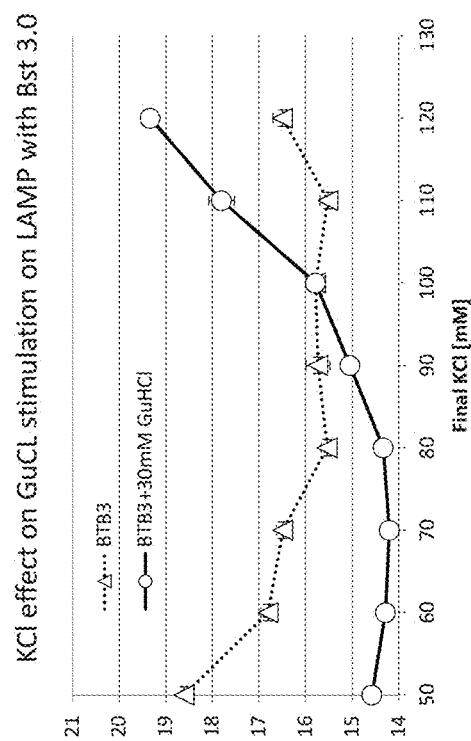

FIG. 17A-FIG. 17C shows that GuHcl was effective in increasing the rate of isothermal amplification reactions and this effect was enhanced by selecting a range of concentrations for NaCl or KCl in the reaction buffer.

FIG. 17A shows the results of standard HDA reactions in IsoAmp® II Kit (H0110) and 0.1 ng plasmid, with 10 mM NaCl versus 40 mM NaCl, in which guanidinium hydrochloride was added at a final concentration of 0 mM-60 mM. The reactions were performed at 65° C. and EvaGreen® dye (Biotium, Inc., Hayward, Calif.) was included to monitor the progression of amplification. The effect of reducing NaCl concentrations was most noticeable at higher concentrations of GuCl (30 mM-60 mM guanidine hydrochloride) resulting in a reduction of Time to threshold (Tt) of 35 minutes (40 mM NaCl) to 12.3 minutes (10 mM NaCl).

FIG. 17B shows an increase in the rate of amplification using the LAMP assay described in Example 1 and Bst 2.0 DNA polymerase with a lambdaI primer set and 0.5 ng lambda DNA in ThermoPol buffer containing 10 mM KCl plus or minus 30 mM guanidine hydrochloride. The addition of guanidine stimulated the LAMP amplification rate significantly at the lower end of the KCl concentration (less than 40 mM KCl).

FIG. 17C shows an increase in the rate of amplification using the LAMP assay described in Example 1 and Bst 3.0 DNA polymerase (also referred to as BTB3) with a lambdaI primer set and 0.5 ng lambda DNA in an isothermal amplification buffer containing 50 mM KCL plus or minus 30 mM guanidine hydrochloride. The addition of guanidine stimulated the LAMP amplification rate significantly at the lower end of the KCl concentration (less than 100 mM KCl).

FIG. 18A-FIG. 18D shows that guanidine hydrochloride not only increases LAMP reaction speed but also improves the limit of detection sensitivity.

FIG. 18A shows that colorimetric LAMP (M1800) could detect 100 copies of synthetic Sars-CoV-2 RNA with 40 mM guanidine hydrochloride using primer set 1. The color change from pink to yellow indicates a positive detection. "None" denotes no guanidine hydrochloride. In the presence of 40 mM guanidine hydrochloride, 8/8 positive reactions were detected, whereas 5/8 positive reactions were detected without it.

FIG. 18B shows the results of real time colorimetric LAMP using primer set 1 in the presence and absence of 40 mM Guanidine HCl. The reaction also contains 1 µM dsDNA binding dye SYTO 9 for monitoring the real time progression of the amplification.

FIG. 18C shows the results with 4 different primer sets. In all cases, sensitivity was increased in the presence of guanidine hydrochloride. The percentage of positive reactions for detecting 100 copies of SARS-CoV-2 RNA is shown in the table. The table shows that guanidine improves the detection sensitivity of all primer sets.

Figure 18D:
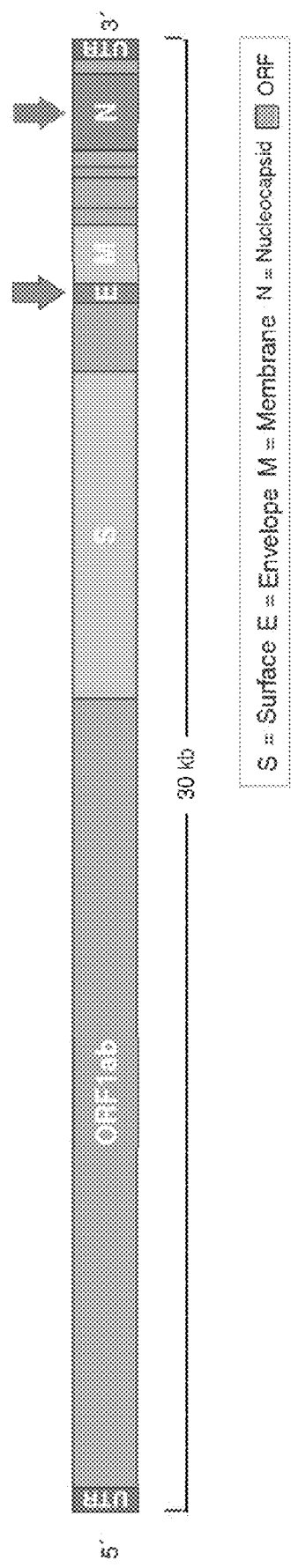

FIG. 18D shows a diagram of Sars-CoV-2 with the location of 2 template sequences (E and N) in the target nucleic acid.

Figures 19A, 19B, 19C:
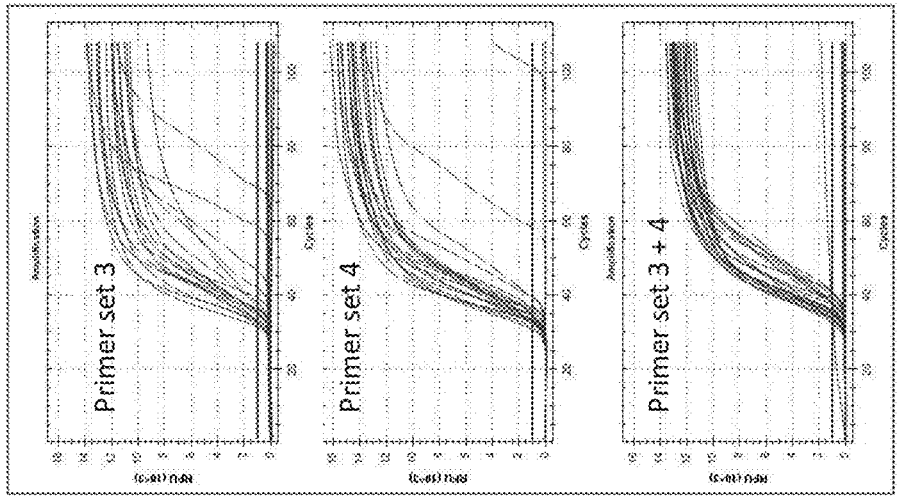

FIG. 19A-19C shows that guanidine allows efficient multiplexing of LAMP amplifications with multiple LAMP primer sets in the same reaction without adverse effects on the rate of amplification while significant improvements in sensitivity were observed.

FIG. 19A shows sensitivity of pH colorimetric LAMP by the percentage of positive samples detected using single sets of primers (identified as sets 3 and 4) and when sets 3 and 4 are combined in the presence or absence of 40 mM guanidine hydrochloride in a 40 minute incubation. The tables shows that 92.2% positives were detected for known test samples containing 50 copies synthetic SARS-CoV-2 RNA using a combined set of primers 3 and 4 with guanidine, compared with 28% for single sets of primers in the absence of guanidine.

FIG. 19B shows the sensitivity of pH colorimetric LAMP for detecting 12.5 copies of synthetic SARS-CoV-2 RNA in the presence of guanidinium hydrochloride and a plurality of primer sets. The results shows an increase of detection rate with any combinations of 2 primer sets (3+4, 3+5, 4+5). The reactions including all 3 primer sets (3+4+5) also showed further increase of detection rate over any 2 primer sets, providing detection of 57% of all positives in a 40 minute incubation. The reactions without template remained negative and showed no sign of amplification signal, indicating robust specific amplification.

FIG. 19C shows that real time amplification with guanidine hydrochloride resulted in an expected rate of amplification with a combination of oligonucleotide primer sets 3 and 4 and 50 copies of target CV-19 RNA where the combination of primer sets did not adversely affect the rate of amplification.

Figure 20:
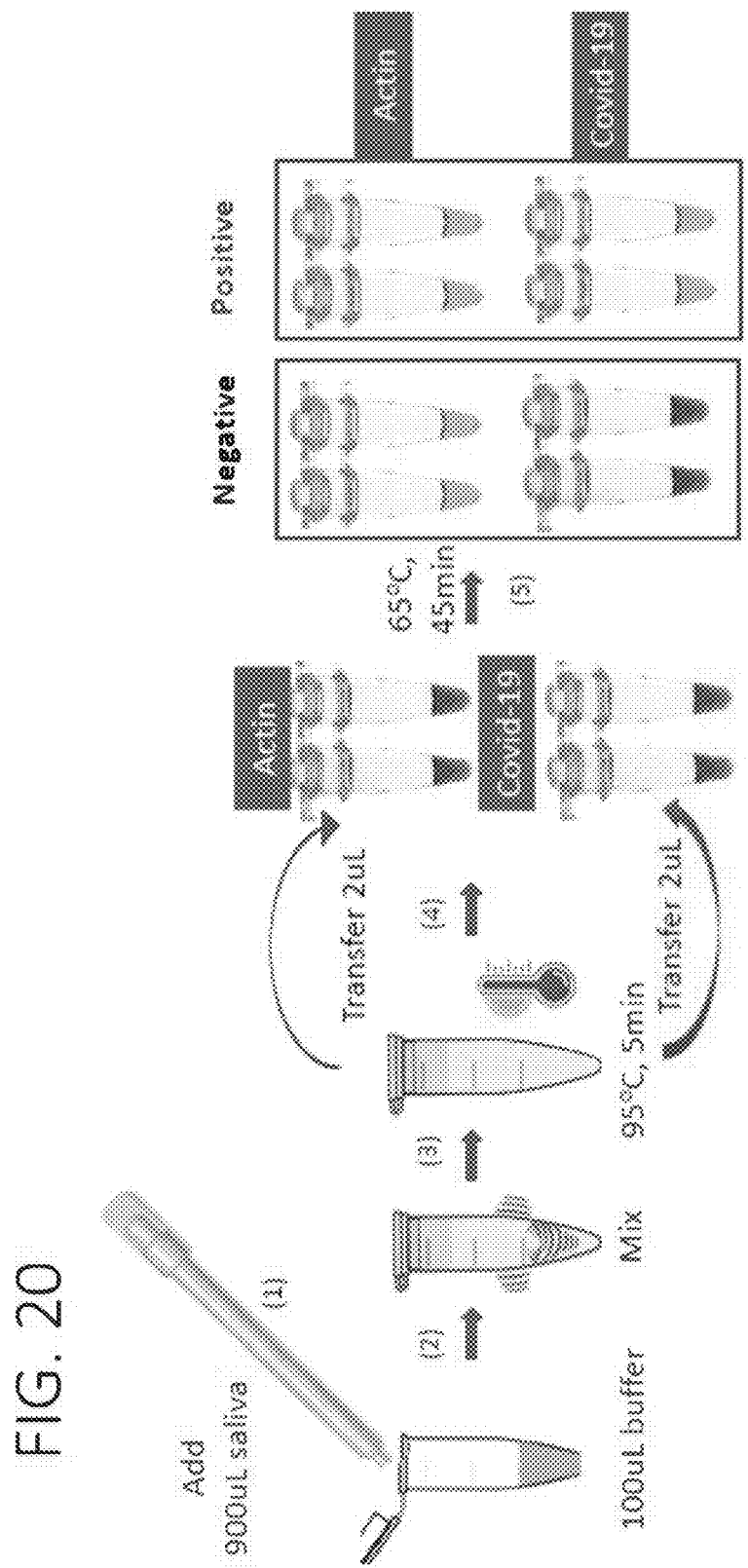

FIG. 20 shows an example of the use of lysis buffer for SARS-CoV-2 detection in saliva where 900 µl of saliva from a patient is added to 100 µl of 10× lysis buffer (1), mixed (2) and then heated to 95° C. for 5 minutes (3). 2 µl of the sample is then added to 18 µl of pH colorimetric LAMP Master mix either containing primers to SARS-CoV-2 (target) or primers for actin (control) (4). After an incubation for 45 minutes at 65° C., the test tubes were examined for a color change from pink to yellow indicative of the presence of SARS-CoV-2 (5).

FIG. 21A-FIG. 21B shows that various ratios of the reagents in the lysis buffer spiked with synthetic SARS-CoV-2 RNA were tested to determine which combination if any interfered with pH colorimetric LAMP and if not which conditions provided the greatest sensitivity for detecting 40 copies of the virus genome. The results did not suggest any interference and the saliva lysis mixture containing 4 mM TCEP (reducing agent) and 75 mM LiCl at pH 8.0 with 400 mM guanidine hydrochloride (GnHCL) gave the best results.

FIG. 21A shows 6 different conditions for the saliva lysis buffer.

FIG. 21B shows the color changes indicative of a positive result under the 6 different test conditions where 4 mM TCEP (reducing agent) and 75 mM LiCl at pH 8.0 with 400 mM guanidine hydrochloride (GnHCL) resulted in 100% detection of 40 copies of viral genome.

Figure 22:
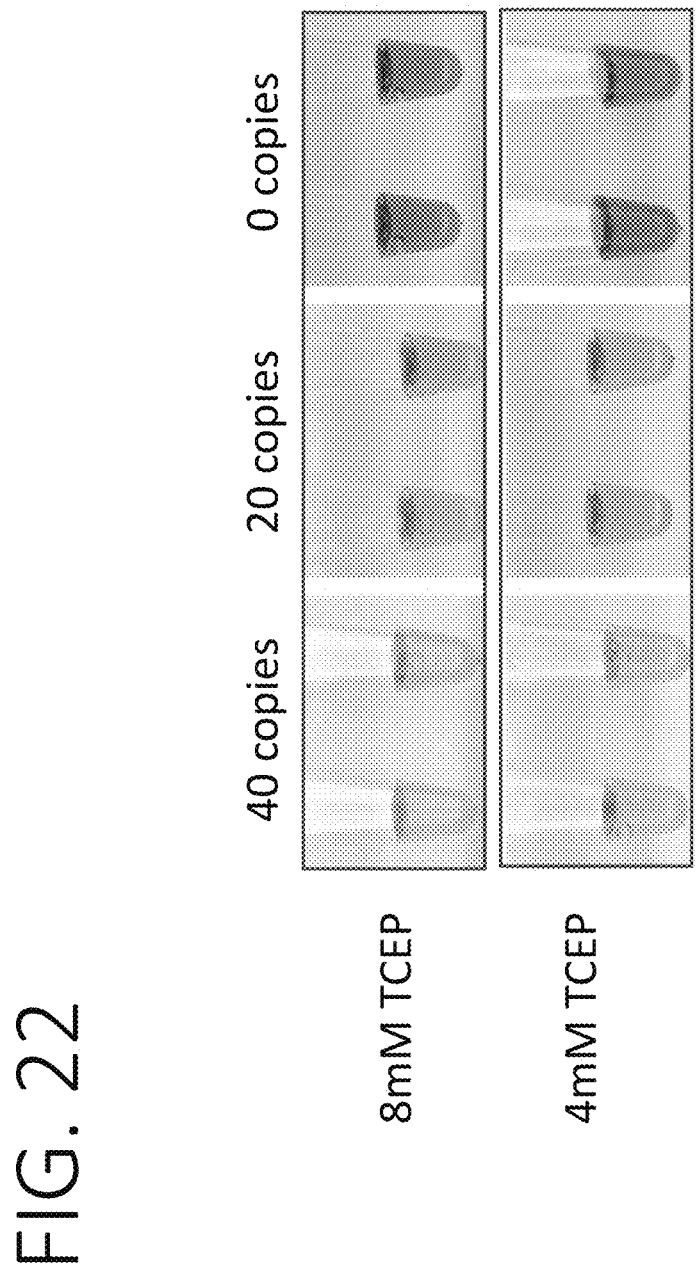

FIG. 22 shows that 8 mM TCEP in addition to 75 mM LiCl and 400 mM GnHCL performed similarly to 4 mM TCEP in the saliva lysis buffer when 5 µl 10× lysis buffer was added to 45 µl saliva sample containing inactive virus particles (SeraCare, Milford, Mass.) and heated for 5 minutes at 95° C. 2 µl of this sample was then added to 18 µl LAMP master mix and incubated for 35 minutes at 65° C.

Figures 23A, 23B, 23C, 23D:
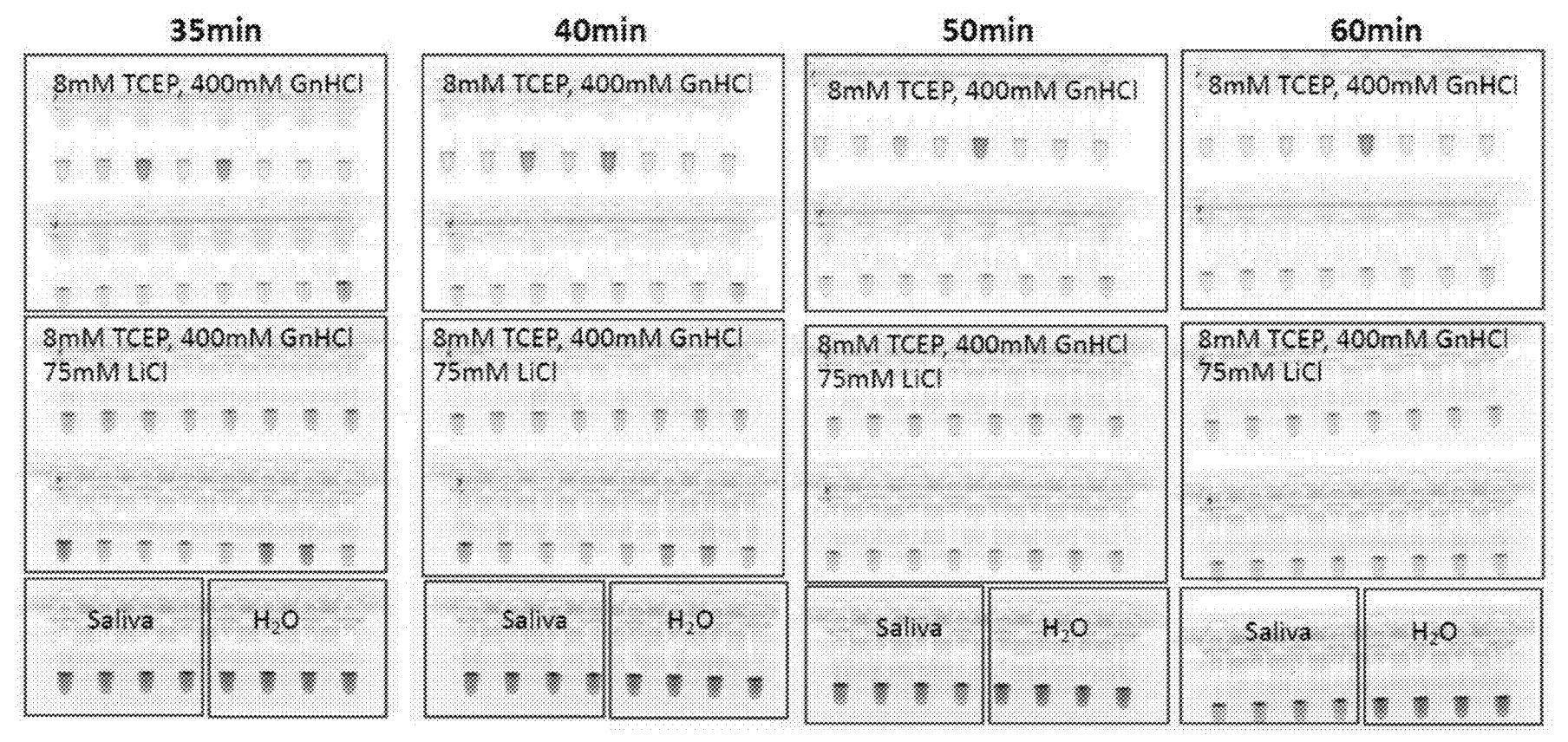

FIG. 23A-FIG. 23D shows the effect of varying the LAMP assay time after the 5 minute saliva lysis reactions on saliva spiked with 10,000 cps/ml synthetic SARS-CoV-2 RNA (20 copies/2 µl) using a saliva lysis buffer containing 8 mM TCEP, 0 mM LiCl/75 mM LiCl and 400 mM GnCL. Increased sensitivity was observed over time with the presence of LiCl consistently contributing to increased sensitivity as the time of incubation increased beyond 35 minutes. Saliva not containing RNA and $H_2O$ were used as negative controls.

Figure 24:
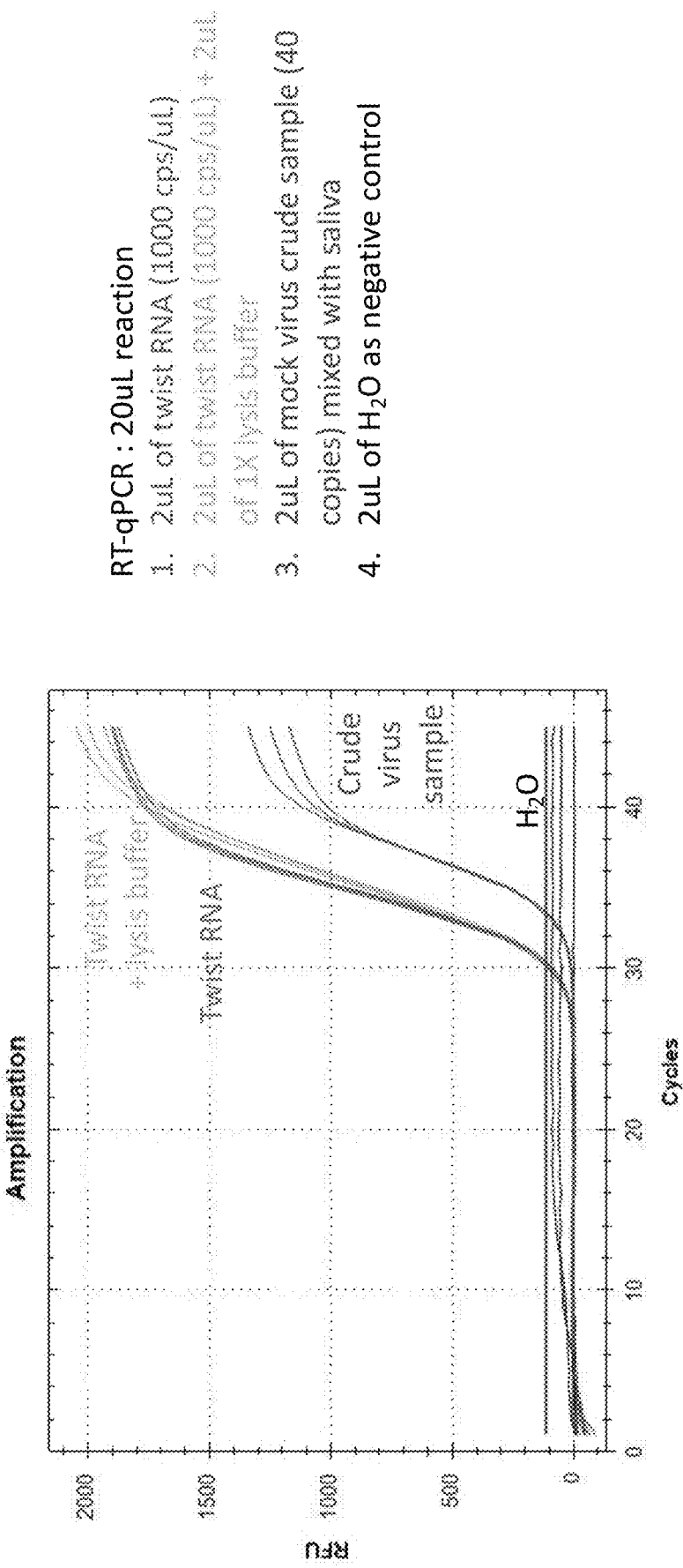

FIG. 24 shows that when a saliva sample spiked with a known copy number of synthetic SARS-CoV-2 input (Twist) is treated with saliva lysis buffer (8 mM TCEP, 75 mM LiCl and 400 mM GnCl), followed by RT-qPCR, the lysis buffer was shown to have minimal or no adverse effect on the RT-qPCR reaction.

Figure 25:
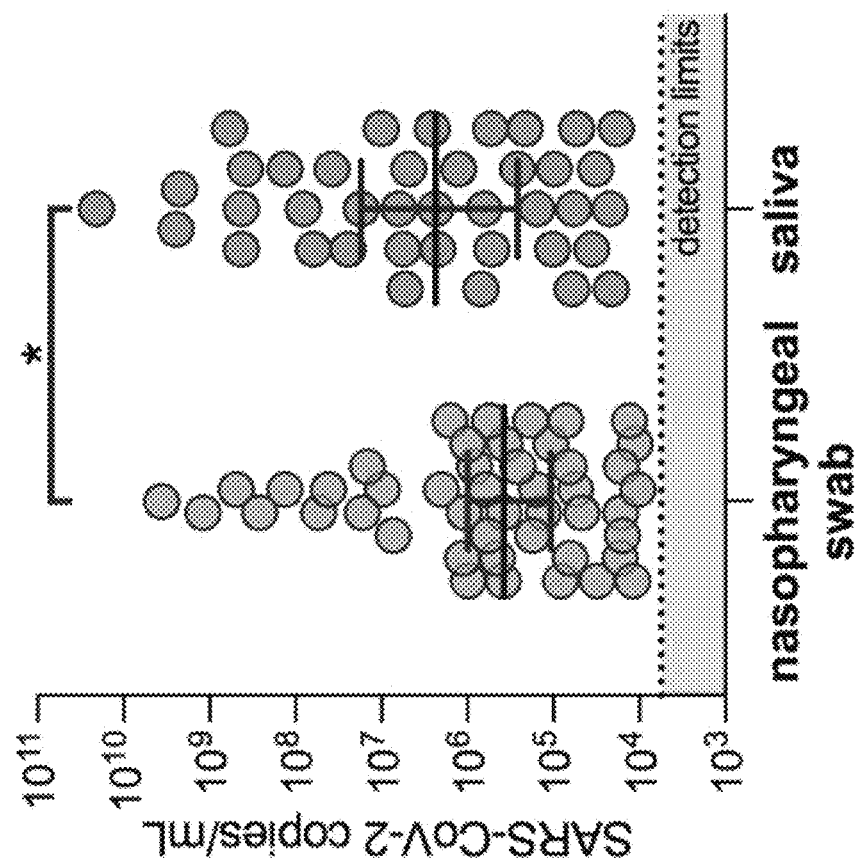

FIG. 25 shows that the lysis buffer described in FIG. 23A-FIG. 23D and FIG. 24 can provide similar sensitivity of virus detection as that reported by others after purification of the viral RNA from nasopharyngeal swabs and saliva (Wyllie et al. MedRxiv Apr. 22, 2020: https://doi.org/10.1101/2020.04.16.20067835).

All positive nasopharyngeal swabs (n=46) and saliva samples (n=39) were compared by a Mann-Whitney test (p<0.05). Bars represent the median and 95% Cl. Our assay detection limits for SARS-CoV-2 using the US CDC "N1" assay is at cycle threshold 38, which corresponds to 5,610 virus copies/mL of sample (shown as dotted line and grey area).

Figure 26:
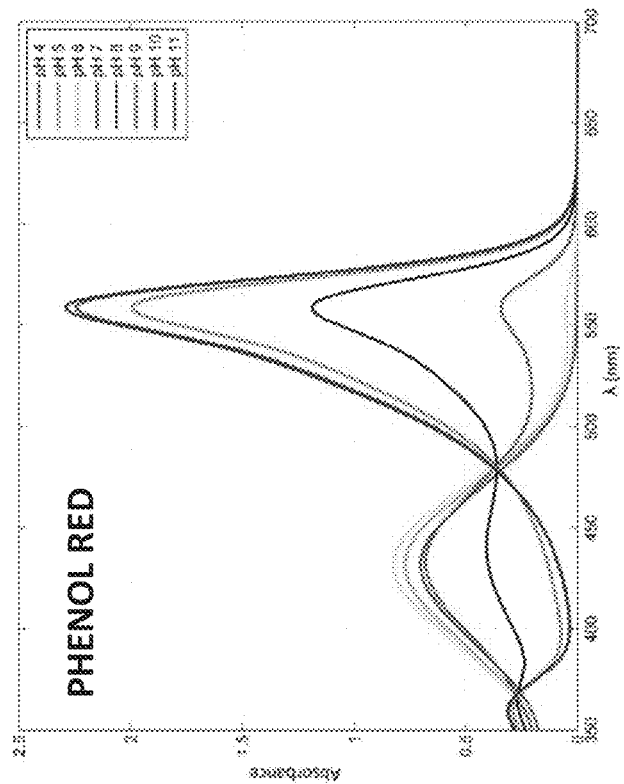

FIG. 26 shows that endpoint absorbance ratio (432 nm/560 nm wavelengths) at a range of pH from pH 4-pH 11 can be measured by a colorimeter. The highest positive signal at 560 nm is between pH 9-pH 11 and the highest negative signals at 432 nm occurs at pH 4-pH 6. The 432/560 nm signal ratio can be used to determine positive and negative samples in pH-dependent colorimetric LAMP.

Figure 27:
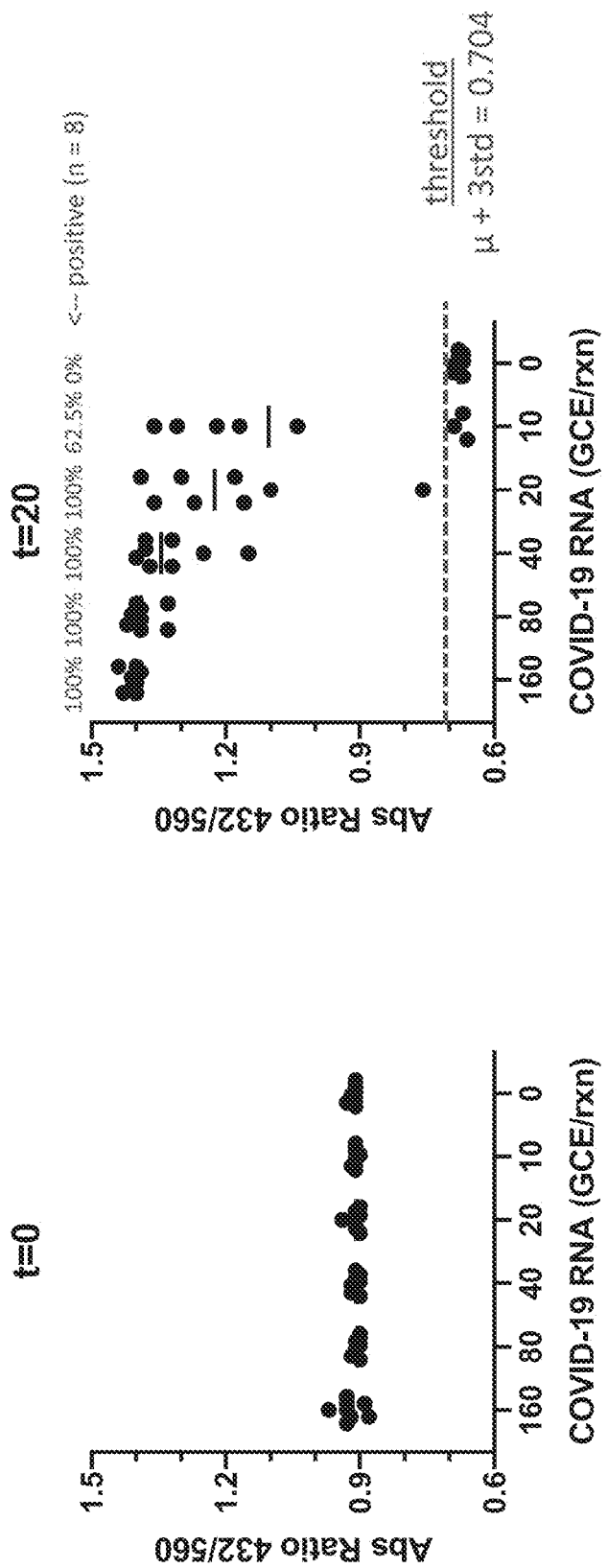

FIG. 27 shows the absorbance results after pH dependent colorimetric LAMP was performed on samples containing synthetic SARS-CoV-2 RNA using dual primer sets of N2 and E1 after no incubation at 65° C. and after 20 minutes incubation at 65° C. The samples were allowed to cool to room temperature before the color was measured in the SpectraMax® (Molecular Devices, San Jose, Calif.). Data is provided from a SpectraMax readout that provided 100% detection of 20 copies of SARS-CoV-2 RNA and 62% detection of 10 copies of SARS-CoV-2 RNA using a sample spiked with 20 copies of SARS-CoV-2 RNA.

FIG. 28A-28F shows an example of an automated workflow that permits 100,000 reactions in about 20 hours. This is calculated from a batch size of 5,760 reactions (15×384 well plates or 60×96 tube racks) with a process time of 40 minutes/sample and 100 minutes/batch.

Figure 28D:
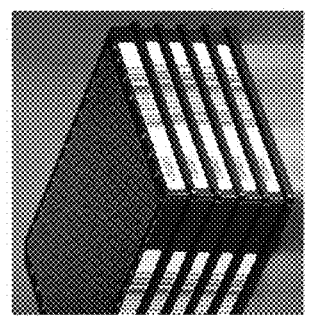
Figure 28C:
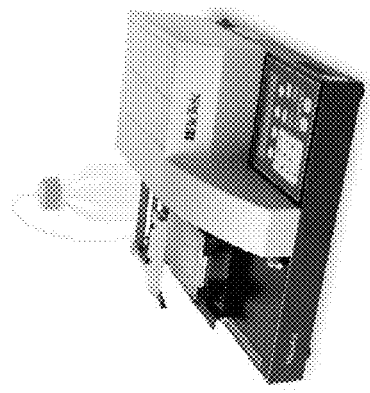
Figure 28F:
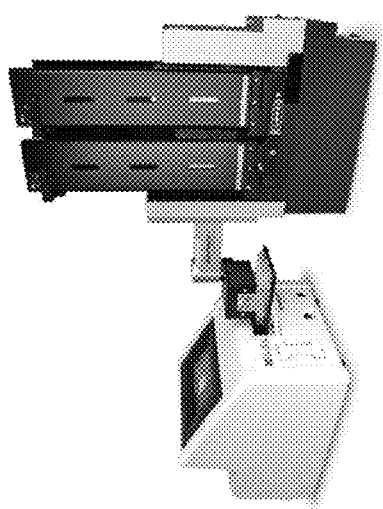
Figure 28B:
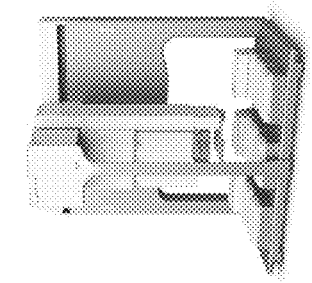
Figure 28A:
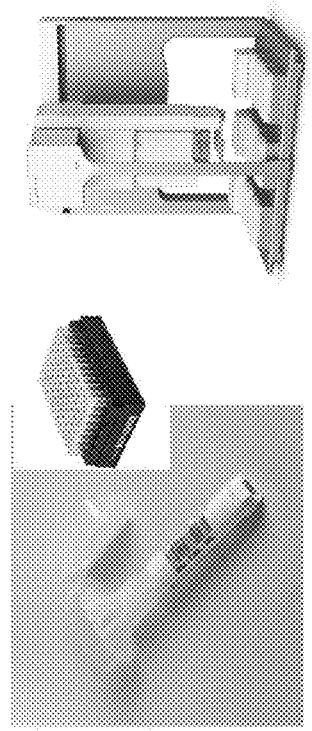

FIG. 28A shows how an individual saliva sample from a collection tube might be placed in a tube containing saliva lysis buffer in a 96 tube rack.

FIG. 28B shows a robot that can transfer samples (for example 3 µl) from individually 2D barcoded sample collection tubes or batches of 4×96 tube racks to 384 well plates with a linear barcode to associate each sample to a discrete well location in 4 minutes.

FIG. 28C shows a robot liquid handler that can add for example 17 µl of reaction mix (e.g. 2 µL 10× primer mix, 10 µL WarmStart Colorimetric Lamp 2× Master Mix (M1800), 5 µL of DNAse, RNAse free H2O) into the 384 well plate within about 1 minute.

FIG. 28D shows a stack of plates each with plastic seal ready for the LAMP reaction.

Figure 28E:
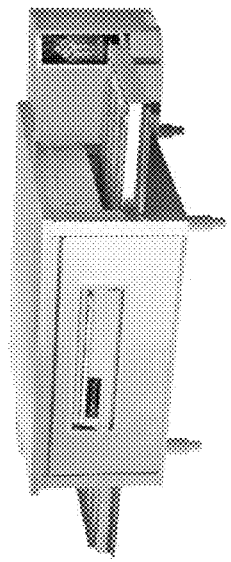

FIG. 28E shows two devices for performing LAMP that requires incubation at 65° C. for a period of time such as 30 minutes. This may be achieved by means of a horizontal conveyor belt that sends each plate through a heated chamber so that the residence time in the chamber is the desired incubation time. Alternatively, this may be achieved by stacking plates in a tower incubator where heating occurs for the programmed time.

FIG. 28F shows a robotic plate handler that takes the 384 plates from the incubator and places them in sequence in a SpectraMax or other spectrophotometer (absorbance reader) that records the 2D barcode on the plate and the color of each well at specific wavelengths.

Figure 29:
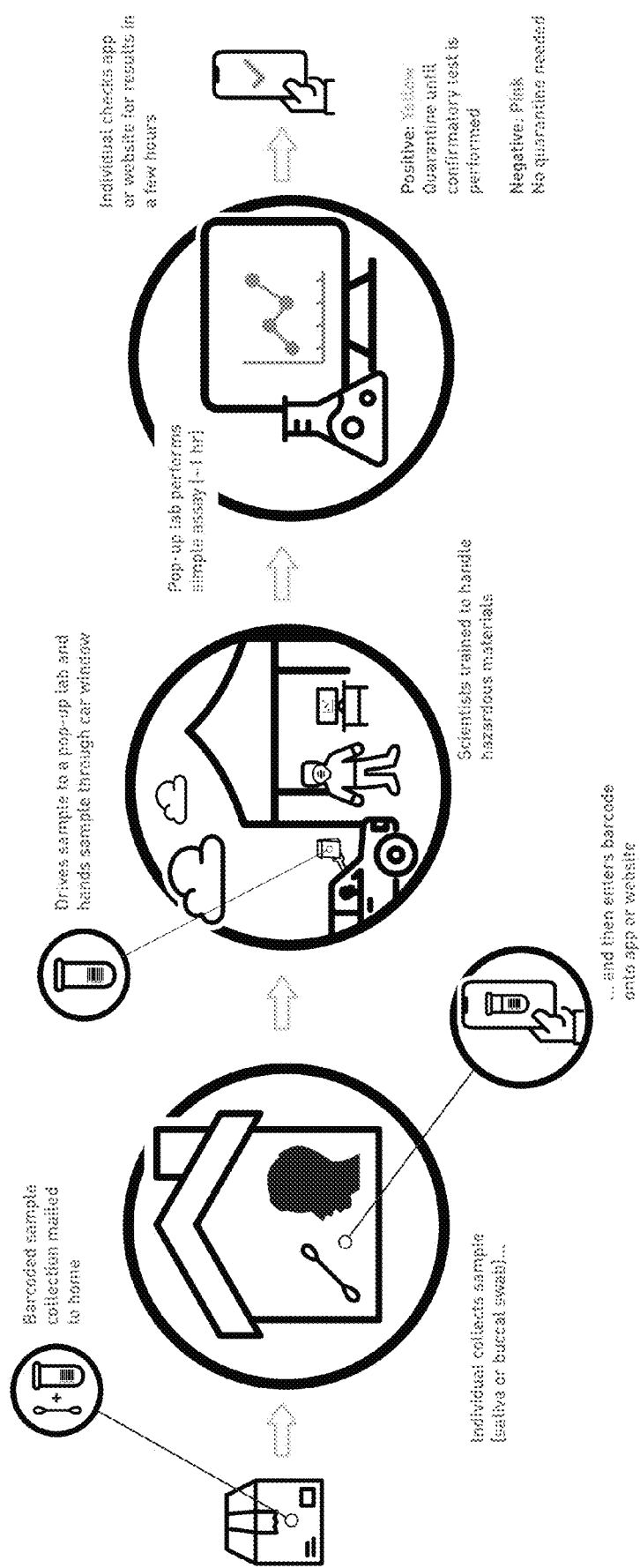

FIG. 29 shows a schematic for handling large numbers of patients at a pop-up laboratory using embodiments of the rapid LAMP method for detecting Sars-CoV-2.

DESCRIPTION OF EMBODIMENTS

Embodiments utilize isothermal amplification, such as LAMP, and simple visual detection of amplification in a liquid or on a reaction matrix for potential use in rapid, field applications. LAMP is an isothermal amplification protocol first developed by the Eiken Chemical Co. in Japan (see for example, Notomi et al. Nucleic Acid Research (2000) 28, E63). LAMP is also described in detail in U.S. Pat. No. 6,410,278 and Mori et al., J. Infect. Chemother. 2009 15: 62-9. In LAMP, four primers recognize six unique sequences in the template region. Two of the primers are designated as "inner primers" (HP and BIP) and two are designated "outer primers" (F3 and B3). In addition to containing a sequence that is complementary to a target sequence at their 3' ends, the inner primers also contain a tail that comprises a sequence that is downstream of the 3' end of primers in the template. Thus, extension of an inner primer results in a product that has a self-complementary sequence at the 5' end. Displacement of this product by an outer primer generates a product that has a loop at the 5' end. Thus, the primer sets used in LAMP typically contain four, five or six template-complementary sequences, where four sequences are found at the 3' ends of the primers and two of the sequences are found at the 5' ends of two of the primers. The initial reaction in LAMP results in a DNA product that has a dumbbell-like structure. In this product, the ends form stem loops and the single stranded region in between the stem loops is copied from the template. This product self-primes its own amplification to amplify the template sequence. LAMP uses a strand-displacing polymerase, and is isothermal, that is it does not require heating and cooling cycles.

Primer sets for LAMP as used herein refer to four to six primers that includes optionally loop forward and/or backward primers (LF and LB) in addition to forward internal primers (HP) and backward internal primers (BIP) and forward primer (F3) and backward primer (B3).

LAMP assays are described herein that enable rapid and sensitive detection of target nucleic acids; such as a nucleic acid of or associated with a pathogen, such as a virus, in a human or animal population. These assays are simple and portable while retaining sensitivity and minimizing false positives and negatives. The LAMP assays described herein rely on detection of a change in some aspect, preferably color of a dye in a reaction mix due to a change in pH or metal ions. Turbidity may also be used as an end point in some LAMP assays. All abbreviated references herein to embodiments that relate to "colorimetric tests" refer to detection of a target nucleic acid (e.g. a target pathogen nucleic acid) by a change in color of a dye in a reaction mix due to a change in pH or metal ion binding or dissociation.

The diagnostic colorimetric LAMP methods described herein may be used for detecting pathogens, including any of: prokaryotes such as bacteria, eukaryotic pathogens such as multicellular parasites, single cell pathogens such as trypanosomes or yeasts, and *mycoplasma*; as well as for use in genetic tests, such as for genetic diseases, and in personalized medicine, which may require SNP detection or gene analysis of the genome of a subject or RNA analysis to determine gene expression profiles in response to an environmental or metabolic event. Many of the examples are directed to the SARS CoV-2 RNA virus because of a sensitive diagnostic test is of paramount importance. However, the improvements in sensitivity described here may be applied to any colorimetric LAMP based assay to detect a target nucleic acid and indeed may find applications in non-LAMP assays also.

Described herein are modifications to isothermal amplification diagnostic assays (e.g. LAMP) to improve their sensitivity. Such modifications may include one or more of:
  (a) sample collection in water or weak buffer;
  (b) avoiding nucleic acid purification for assaying for the target nucleic acid in the sample;
  (c) addition of one or more RNase inhibitors to the sample (e.g. into a sample tube) to prevent loss of sample and thereby to increase overall sensitivity of the assay;
  (d) addition of thermolabile Proteinase K to the sample (e.g. into the sample tube) to facilitate the efficiency of the LAMP reaction by removing unwanted protein, followed by heat inactivation of the Proteinase K prior to subsequent isothermal amplification (e.g. LAMP or RT-LAMP) reactions;
  (e) addition of dUTP and UDG (e.g. thermolabile UDG) into the reaction mix to prevent sample carryover when large numbers of samples are being handled;
  (f) addition of various components to the reaction mix to reduce background and enhance signal, such as a helicase (see for example, U.S. Pat. No. 9,920,358), or a carboxamide (see for example, U.S. Pat. No. 9,546, 358);
  (g) other adjustments to reduce background and enhance signal, such as optimizing the ratio of probes (see for example, U.S. Pat. No. 9,074,249); design of primers or probes (see for example, U.S. Pat. No. 9,074,243), improvements in Bst polymerase for use in LAMP (see for example, U.S. Pat. Nos. 9,157,073 and 9,127,258)

and/or in reverse transcriptases for use in LAMP (see for example, U.S. Pat. Nos. 9,920,305, 9,580,698 and 9,932,567);

(h) storage of concentrated master mix at room temperature in a lyophilized form for uses that include ease of transport and storage at the test site;

(i) substituting a pH sensitive dye and associated amplification buffer with PAR, manganese ions, a detergent such as a non-ionic detergent and a standard isothermal reaction buffer;

(j) storing lyophilized master mix with probes and PAR on a paper, microfluidic device, or polymer surface for use in a target specific strip test where a liquid sample is added to the paper, microfluidic device or polymer surface containing the lyophilized reagents and a readout is obtained;

(k) adding a guanidine salt to increase the rate of the isothermal amplification (e.g. LAMP) reaction and increase sensitivity;

(l) using multiple sets of primers each set targeted to a single template region in a target nucleic acid to enhance sensitivity;

(m) reducing the concentration of NaCl or KCl in the buffer in the presence of guanidine salts to enhance the rate of reaction;

(n) using a sample lysis buffer for direct analysis of nucleic acids from a sample without purification where the lysis buffer contains a guanidine salt and a reducing agent such as TCEP and optionally LiCl and optionally a detergent;

(o) use of a dual wavelength spectrophotometer to distinguish positive from negative samples rapidly in high throughput workflows and/or real time analysis;

(p) use of a high throughput automated workflow from sample collection to recording of results to achieve at least 100,000 samples in 20 hours;

(q) a point of care kit that provides a positive/negative result concerning the presence of a nucleic acid within 45 minutes of receiving a sample and without instrumentation outside a source of time- and/or thermostat-regulated heat.

The combination of a quick sample preparation method with an easy detection process provides portable, field detection in addition to a rapid screening for point-of-need testing applications. The use of this diagnostic methodology for a virus that represents an emerging significant public health concern provides applications outside of traditional laboratories that will enable greater prevention and surveillance approaches. These embodiments provide the basis for a model for inevitable future outbreaks of viral pathogens and indeed any infectious agent to dramatically expand the reach of testing capabilities for better healthcare outcomes.

The term "Bst polymerase" refers to any of Bst large fragment or mutant of the Bst polymerase or Bst large fragment. Examples of mutants of Bst polymerase are described in U.S. Pat. Nos. 9,157,073, 8,993,298, and 9,127,258.

The term "master mix" refers to a combination of reagents which can be added to a sample to execute a reaction in an assay where the combination enhances the efficiency and speed of performing the assay. The master mixes described herein include a mesophilic strand displacing DNA polymerase and may additionally include one or more other enzymes such as a reverse transcriptase, uracil deglycosylase for example a thermolabile deglycosylase, and a thermolabile Proteinase K such as a thermolabile Proteinase K. The master mix may also include a reversible inhibitor of DNA polymerase activity and if a reverse transcriptase is present, a reversible inhibitor of reverse transcriptase activity for inhibiting the activity of these enzymes below 40° C. This permits setting up of a reaction at room temperature while avoiding nonspecific amplification. The master mix may also contain inhibitors of RNases. The master mixed may also include dNTPs such as dTTP, dATP, dGTP and dCTP as well as dUTP for carryover prevention. For example, a 2× master mix may contain the dNTPs in equal quantities except the dUTP at 50% concentration of the other dNTPs. The master mix may include single strand binding proteins and/or helicases to reduce nonspecific amplification. The master mix may include a pH-sensitive dye or a metallochromic dye. The master mix may be lyophilized or freeze dried. It may be preserved for storage in a suitable buffer that may contain at least one reducing agent and at least one detergent and capable of storage at −20° C. for an extended period of time (for example months). The master mix for use in pH colorimetric LAMP may have a low buffer concentration such as 1.5 mM Tris or less. A low buffer concentration is not required if a metallochromic dye or fluorescent dye is used to detect amplification. The master mix may be prepared in a 2×, 3×, 4×, 5×, 10× or any suitable concentration. The master mix once diluted by the sample will result in a 1× concentration. The master mix may contain primers or primers are not contained in the master mix.

Kits refer to a combination of materials that are needed to perform a reaction. A kit may contain multiple tubes or a single tube. The kit may include a mixture of lyophilized reagents and reagents in a storage buffer. In one embodiment, the kits described herein contain multiple tubes wherein a strand displacing polymerase or master mix is contained in one tube, guanidine salt in another tube and oligonucleotide primers in a third tube. In embodiments of the kit, unless the primers are lyophilized together with the master mix, the oligonucleotide primers in the third tube comprise a plurality of sets of primers, for example 12 different primers consisting of two sets of oligonucleotide primers where each set has 6 primers wherein both sets of primers target different sequences in a single target nucleic acid. In one example, a plurality of different target nucleic acids may by analyzed by the methods described herein, for example, a plurality of sets of primers in the third tube may target sequences in the genome of SARS-CoV-2 and a different plurality of sets of primers in the third tube may target sequences in the genome of influenza virus. Different indicators associated with the oligonucleotide primers for influenza and coronavirus can provide different color or fluorescence endpoints corresponding to the presence of either or both viruses. A single test need not be limited to the detection of two different target nucleic acids. A single test can be designed to identify any number of different target nucleic acids associated with a distinguishable color or fluorescence endpoint. The plurality of primers in the third tube may additionally contain a sample identification sequence if multiple samples from different sources are pooled for combining with the kit. In one embodiment, the kit contains a 2× master mix, a 5×-25× guanidinium salts, and 5×-25× of primers.

Sampling to Obtain Target Nucleic Acid

In embodiments, purified nucleic acid such as RNA or DNA, or direct tissue or cell lysate or samples of body fluids can be analyzed in a colorimetric LAMP such as a pH dependent colorimetric LAMP assay, a fluorescent LAMP assay, or a metallochromic based LAMP assay. Other endpoint indicators include molecules having a moiety that intercalates into dsDNA and non-metallochromic indicators that change color in the presence of pyrophosphates. Either purified nucleic acids, body fluids or lysates can be used in a simple, rapid method for SARS-CoV-2 RNA detection.

In one embodiment, a sample is obtained from the nasal passages of a patient (human or mammal) by nasal swab or from the buccal cavity or other suitable body fluid such as saliva, sputum, mucous, blood, urine, sweat, lymph fluid, feces. Samples may also be obtained from an environmental source such as a food, plant, sewage, water, dust, or surface swab of an object. Samples can be placed into a small volume of water saline, TE, or suitable transport medium (for example, a universal transport medium for viruses) or directly into a lysis buffer that inactivates and breaks open the pathogen if that is the diagnostic target. The samples may be further purified from lysis buffer or added without further purification to the amplification master mix where the sample or an aliquot of that sample can be introduced into the amplification master mix for testing for the presence of a pathogen, gene, SNP, mutation or other nucleic acid target.

The pH of the sample may determine the type of assay detection that is preferably used. For example, urine has an acid pH so a metallochromic based assay that is not pH sensitive might be used, instead of a pH endpoint.

Saliva

The nucleic acids in saliva may come from cheek cells and tongue cells as well as any typical oral microbial species. Saliva can be collected from a human subject using a commercial collection device such as provided by for example any of Boca Scientific Inc. (Westwood, Mass.), Salimetrics LLC (Carlsbad, Calif.), Mantacc (Shenzhen, China), Greiner Bio-One BD Sputum Collection (Monroe, N.C.). Saliva has some challenges as a body fluid for nucleic acid analysis. Its pH and composition may vary according to the biology of the individual and also according to the recent intake of food and/or liquid into the mouth. For example, it is well known that a glass of water containing the juice of a squeezed lemon will cause the saliva to become acidic for a short time after intake. Where the saliva based diagnostic test relies on an amplification procedure that is pH dependent such as pH dependent colorimetric LAMP, the pH can be normalized to the extent necessary with respect to subsequent dilution before initiation of the amplification reaction so that the concentration of buffer in the final reaction mixture is less than a corresponding amount of 5 mM Tris while optimizing the pH to be preferably within the range of pH 7.9-pH 8.3. Alternatively, the subject providing the saliva might avoid ingestion of a particular food or drink for a predetermined number of minutes (such as 30 minutes) before providing the saliva sample.

Where saliva is tested for a pathogenic virus, it may be desirable to immediately inactivate the virus in the receiving tube. In these circumstances, a detergent may be added to the collection tube if storage before analysis is intended. For example, Triton X-100 in relatively high concentrations has been shown not to interfere with a subsequent colorimetric LAMP reaction (see for example, FIG. 11B). The lysis buffer as described below will inactivate the virus and release nucleic acid for amplification or for sequencing. The lysis buffer described in Example 9 is suited for amplification generally as illustrated for RT-qPCR and for LAMP. The saliva lysis buffer may also be applied to other body fluids for a similar purpose. The lysis buffer may be used for obtaining nucleic acid samples suitable for direct sequencing such as by Oxford Nanopore. LAMP assays using the kits described herein that utilize indicators that are not pH dependent, guanidine salts and a plurality of primer sets for a single nucleic acid target and further optionally including reducing agents, detergents, carryover prevention etc. may be used as an alternative to pH colorimetric LAMP to analyze saliva for the presence of the nucleic acid target.

As illustrated in FIG. 20, it may be desirable to store a saliva sample in a suitable buffer optionally containing RNase inhibitors and/or guanidine chloride. The sample tube is heated to about 95° C. for about 5 minutes, to lyse the virus and inactivate any residual RNAses prior to adding LAMP kit components for LAMP, performing the LAMP reaction and observing a color change or change in fluorescence.

In one embodiment, the sensitivity of the methods described herein was tested in samples of human SARS-CoV-2 negative saliva spiked with either SARS-CoV-2 viral RNA (Twist Synthetic SARS-CoV-2 RNA Control 2 (MN908947.3) (Twist Biosciences, San Francisco, Calif.) or virus particles provided by SeraCare (Milford, Mass.). An aliquot of the spiked saliva samples was added to the lysis buffer that was then analyzed using a pH colorimetric LAMP assay as shown in FIG. 20. Using the methods described herein it was possible to detect less than a 100 copies of viral RNA (80 copies of virus) derived from a saliva sample, more particularly less than 80 particles, more particularly, 40 particles or less with up to 100% efficacy. This corresponded to less than 50,000/ml virus particles in the original sample where less than 100 copies of virus were detected, less than 40,000/ml copies of virus in the sample (80 copies), 20,000 copies/ml or less in the sample (40 particles) with 10,000 copies/ml corresponding to detection of 20 particles.

Reaction Platform

In one embodiment, a microfuge tube receives the sample, for example a swab, in a suitable buffer. Alternatively, a reaction platform such as a 96 well dish, 384 well dish or other multi-well dish may be used for multiple sample analysis. Alternatively, the sample may be spotted onto a paper, plastic, or glass surface. The sample may also be introduced into a microfluidic device, such as a lab-on-a-chip. In this context, an Echo® Liquid Handler (Labcyte Inc., San Jose, Calif.) may be used to handle fluid samples. Because the one tube reaction is simple, any automated liquid handler of device may be used for analysis of multiple samples. Because the endpoint is a color change, a computerized analysis of a photographic image of the sampling platform, or handheld sample tubes or insertion of the reaction platform into a light reader connected to a computer is enabled for digitizing the reaction platform itself or image thereof. Further details are described in FIG. 26-FIG. 28F and Example 12.

Preparation of a Master Mix for Use in a LAMP Assay on or in a Reaction Platform or Reaction Vessel A master mix can include or be combined with oligonucleotide probes or primers. A master mix can be added directly to the sample, or alternatively, a portion of the sample can be added to the master mix. The primers and/or probes can be added to the master mix prior to adding the mixture to the sample or the primers and/or probes can be added to the sample prior to or after addition of the master mix. Where large-scale analysis of multiple samples is desired, the LAMP primers and/or probes may be incorporated into the LAMP master mix so that all that is required is to add an aliquot of sample (purified nucleic acid or lysed cell or fluid sample) to the master mix and to raise the temperature to 60° C.-65° C. for a 15 minute, 30 minute, 45 minute or 60 minute incubation time for amplification to occur, to detect a change in color or fluorescence that defines the presence of the target nucleic acid.

The master mix will contain a DNA polymerase dNTPs and a suitable buffer or water. The master mix may additionally include one or more of the following: probes or primers, a plurality of sets of primers, reverse transcriptase, dUTP and UDG, a helicase, a single strand binding protein, a carboxamide, an RNase inhibitor (e.g. murine RNase inhibitor or an aptamer), a pH-sensitive dye or a metallochromic dye such as PAR, and/or manganese ions, and/or guanidine salts. The master mix may have been previously stored at −20° C., prepared in a liquid formulation that is stable at room temperature or lyophilized.

Prevention of Carryover of Contaminating Nucleic Acid Between Samples

Even a very small amount of carryover of previously amplified nucleic acid from a positive sample into a tube that might be negative for the target nucleic acid would be very undesirable. For this reason, including dUTP in the dNTPs in a primary amplification reaction results in incorporation of UMP into the amplified nucleic acid. If this previously amplified DNA then strays into a subsequent sample tube, UDG that is present will cleave the incoming contaminant DNA. The established method has been to include dUTP with dATP, dCTP, dTTP and dGTP so that a fraction of dT is replaced by a dU in the amplified DNA of the first sample. The second sample is then exposed to UDG prior to amplification and this enzyme creates an abasic site at the incorporated uracil. Consequently, it is not possible to amplify sample 1 amplified DNA in sample 2 which would result in a false positive. However, before sample 2 is amplified, the UDG is temperature inactivated or it would adversely affect the desired amplification. It is desirable that the diagnostic test described herein is simple to perform, and also rapid and sensitive. Hence a thermostable UDG is incorporated into the master mix along with dUTP so that once the temperature is raised to the temperature required for amplification, namely 55° C.-75° C., the UDG is inactivated.

A preferred feature of embodiments of the diagnostic test described herein is inhibition of carryover contamination. In order to confirm that pH-dependent colorimetric LAMP is not adversely affected by dUTP and thermolabile UDG, a 2×LAMP master mix containing a buffer concentration of less than 8 mM TRIS buffer and the pH sensitive dye was tested with and without dUTP and Antarctic UDG. It was found that master mixes containing dUTP and Antarctic UDG yielded substantially the same speed, sensitivity and specificity observed in the absence of UDG (see Examples 3 and 4 and FIG. 6A-FIG. 6B). Because prevention of carryover is important for high throughput screening, preferably, UDG and dUTP should be included in master mixes for pH colorimetric LAMP detection of pathogens.

Degradation or Inhibition of Unwanted Proteins in Samples Containing Nucleic Acids in the Absence of the Step of Purifying the Nucleic Acid Prior to LAMP Thermolabile Proteinase K (see for example, U.S. patent application Ser. No. 16/719,097) and/or a proteinase inhibitor such as murine Proteinase K inhibitor and/or an RNase inhibitor (see for example U.S. provisional application Ser. No. 62/992,921) can be added to the sample or the reaction tube into which the sample is added. Where thermolabile Proteinase K is used, it may be inactivated before addition of the master mix. Thermolabile Proteinase K is available from New England Biolabs, Inc, Ipswich, Mass.

Storage of the Master Mix: Dried or Liquid

LAMP master mix containing enzymes, dNTPs, buffer, and pH sensitive dyes (e.g. colorimetric or fluorometric dyes), and/or other dyes that bind metals (e.g. PAR), may be freeze dried or lyophilized and stored at room temperature as a master mix, for example a 2× master mix or 5× master mix or a 10× master mix until needed. The master mix may then be added to a solution containing primers and/or sample to be tested for target nucleic acid in a reaction container, a microfluidic device, a lab on a chip device or a matrix such as paper, plastic, or glass.

If the reagents in the master mix are stored in a dried or lyophilized form, then the pH and buffer concentration of the master mix is not relevant until the dried master mix is added to the sample or the master mix is rehydrated. It was here shown that the pH of the buffer of rehydrated master mix is slightly changed when the master mix is rehydrated so this is taken into account during formulation.

Use of Color or Fluorescence Changes in a Diagnostic Test pH dependent colorimetric LAMP is shown here to be quick, easy, reliable, and suitable for scale-up in molecular diagnosis of viruses and multicellular parasites and their pathogens. In certain point of care formats, it may be desirable to utilize a colorimetric LAMP diagnostic test in which a color change occurs as a side product of amplification that does not rely on staining amplified DNA. A desirable format for measuring a color change is a strip test such as routinely used for pregnancy tests that rely on antibodies (CVS) or the Quickvue® in-line StrepA test (Quidel Corporation, San Diego, Calif.) or equivalent. Alternatively, a liquid test may be convenient in which the sample is added to a first solution (e.g., a lysis buffer) from which an aliquot is removed to a second solution containing the master mix that is then heated on a small pad provided with the test kit (this could be an equivalent of an activated handwarmer or directions for heating a small amount of water in a kettle or a heat block). In these circumstances a pH change will result in a color change denoting a positive result. Alternatively, in place of a pH dependent colorimetric LAMP assay, a metallochromic dye such as PAR has been found to be useful in a colorimetric LAMP assay and provides an alternative should body fluid to be tested be acidic such as urine. The PAR based assay is described in the figures and examples. Manganese used in the PAR colorimetric endpoint LAMP assay is a suitable ion as it does not negatively affect the activity of the polymerase or the reverse transcriptase in a LAMP reaction. Because PAR it is not pH sensitive, it has advantages in a variety of situations in which pH colorimetric LAMP is not best suited as enumerated herein. Either pH colorimetric LAMP or PAR may be used in conjunction with Calcein which also binds to manganese to give a fluorescent signal and/or with the fluorescent dye, SYTO 9. Guanidine salts may also be used in conjunction with colorimetric LAMP to enhance the sensitivity of the assay.

Master Mix

In embodiments, a master mix may contain a pH sensitive dye, fluorescent dye or PAR, a polymerase, plus optionally a reverse transcriptase for RNA detection (such as for an RNA virus), primers and dNTPs are combined in a buffer to form a reaction mix. The master mix is preferably in a concentrated form, for example a 2×, 3×, 5×, 7× or 10× master mix where the final amount of master mix after combination with a sample is 1×.

Some of the considerations in forming the master mix beyond those established in commercial master mixes (see M1800 from New England Biolabs, Ipswich, Mass.) may include one or more of the following parameters: (1) the concentration of dye; and (2) the amount of buffer; (3) the pH; (4) dilution of the master mix in the sample; and (5) the proposed incubation time of the reaction mix to which the master mix is added.

(1) In an example of pH dependent colorimetric LAMP, the concentration of dye in the master mix should be sufficient such that when diluted with sample, it enables unambiguous visual detection of a positive sample. However, the concentration of dye must not be so high as to adversely affect the activity of the polymerase and/or reverse transcriptase. In a preferred embodiment, the visually detectable dye in the reaction mix (1× master mix plus sample) is in the range of 50 μM-200 μM.

(2) The amount of buffer in a liquid concentrated master mix should be sufficient to maintain the enzymes and other reagents in a stable condition but suitable for dilution to detect a color change if amplification of a target nucleic acid has occurred. It is desirable therefore not to exceed 5 mM buffer in the reaction mix-sample combination for pH dependent colorimetric LAMP where buffer concentrations of greater than 5 mM (e.g. 5 mM Tris) in the reaction mix designed to detect amplification via a pH-based color change were found to substantially reduce any visually detectable signal for identifying a positive sample. The buffer concentration was formulated to meet the 1× amount of master mix to have an equivalence to 0.5 mM Tris-5 mM Tris. However, PAR or fluorescence based LAMP do not require this limit on buffer concentration.

(3) A pH 8.1-pH 8.5 in the master mix was tested and found to be suitable for phenol red, a pH sensitive dye used in the examples. This pH could be increased up to a preferred maximum of pH 9 while retaining a visually detectable signal change of pH for a positive sample. The pH could also be reduced to below pH 8.1 in the master mix to provide a change in color by the dye according to the established pH range of pink/red phenol red. Lower pH for a detectable color change is undesirable in the event of exposure to atmospheric $CO_2$ that may acidify the solution since the master mix is weakly buffered. As the pH is increased between pH 8.1 and pH 9.0, the color of the negative control becomes more pink. Different pH sensitive dyes have different ranges of pH optima. The pH range is well known in the art (see for example, Tanner et al. (2015) Biotechniques, 58, 59-68).

(4) As described above, LAMP master mixes may be prepared as 2×, 3×, 5×, 7× or 10× although 2×, 5× or 10× are the usually preferred concentrations for easy dilution into a sample. For biological material containing enzyme inhibitors such as blood, sputum, and urine but not necessarily nasal or buccal swabs, it may be desirable to dilute the sample at least two fold before adding to the appropriately concentrated master mix. In addition to this strategy, adjustment of the acidic pH of urine or the alkali pH of sodium hydroxide treated sputum may be desirable to ensure that the pH of the sample does not inhibit the detection of the amplified target nucleic acid in the sample. Buccal and nasal swabs can be placed in water or transport media and added in a 1:1 ratio to a volume of master mix resulting in a pH and buffer concentration as described above. In some circumstances, it may be desirable to extract the nucleic acid, for example, using Monarch® (New England Biolabs, Ipswich, Mass.), Qiagen or Roche purification kit prior to testing. In these circumstances, the samples can be used in higher volumes especially if eluted from extraction matrices in diluted buffer or water. Lysis buffers are discussed below.

Figure 1:
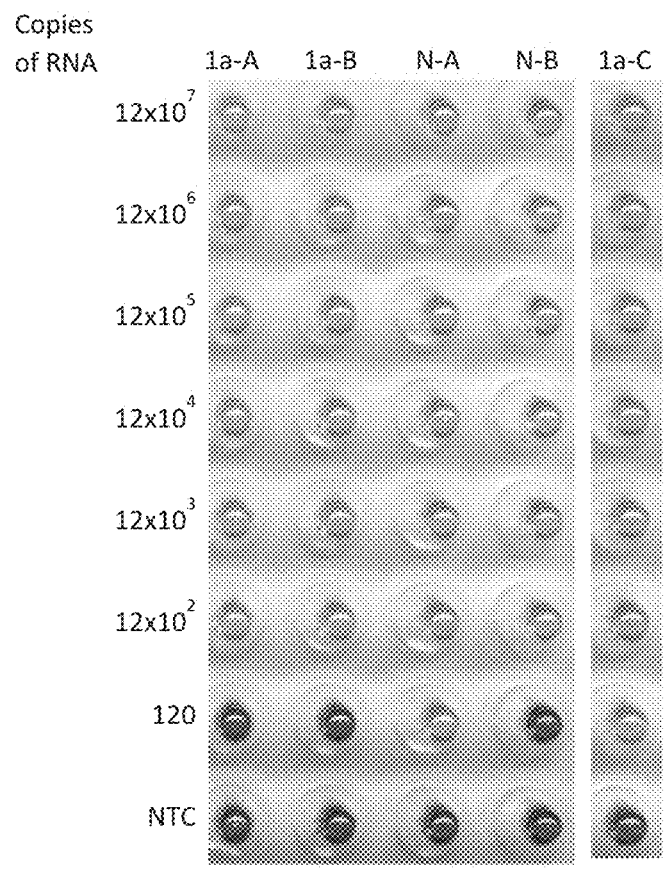
FIG. 1 shows detection sensitivity of synthetic SARS-CoV-2 RNA amplicons by a pH dependent colorimetric LAMP assay using phenol red as the indicator that changed color from red to yellow when amplification of a target nucleic acid occurred, causing the pH of the reaction mixture to decrease. 5 sets of LAMP primers (1a-A, 1a-B, N-A, N-B, and 1a-C) were tested with target nucleic acid concentrations ranging from $120 \times 10^6$ to 120 copies of viral RNA (Twist Biosciences), or a no-template control (NTC). Yellow, positive amplification; pink, no amplification.
Figure 2A:
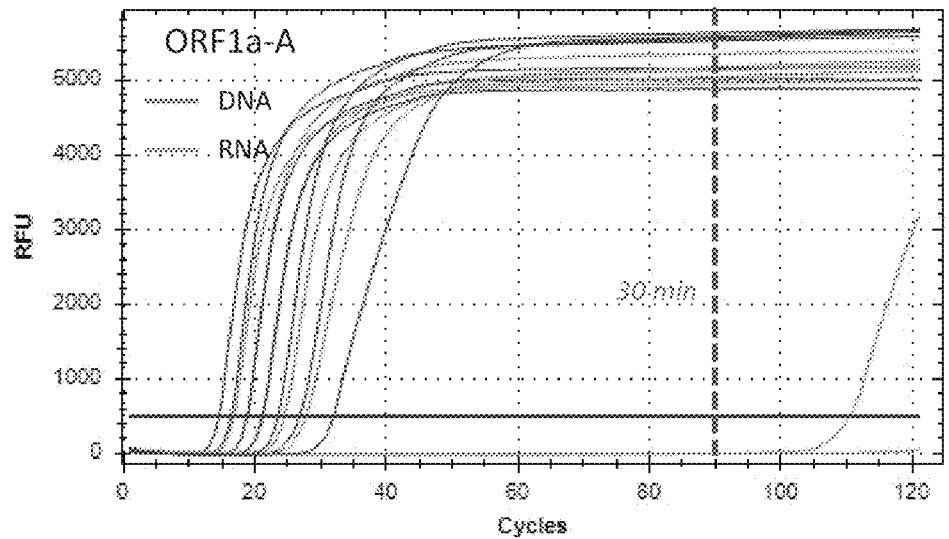
FIG. 2A-FIG. 2B shows that RNA can be detected as efficiently as DNA using pH dependent colorimetric LAMP (NEB-M1800) using the sets of primers described in Example 1 that targeted two different SARS-CoV-2 template regions. A comparison of targeted RNA and gBlock double-stranded DNA (dsDNA) in LAMP amplification is shown using real time amplification curves. Two primer sets (ORF1a-A in FIG. 2A and Gene N-A in FIG. 2B) were used to amplify either RNA (green curves, dilutions from $120 \times 10^6$ to 120 copies) or gDNA (blue curves, $60 \times 10^6$ to 60 copies). Using the ORF1a-A primer set, the amplification of gBlock was faster than amplification of the RNA target. Using the Gene N-A primer set, amplification of the RNA was slightly faster. Each "cycle" represents 20 seconds, with 30 minute timepoint noted by dashed line.
Figure 2B:
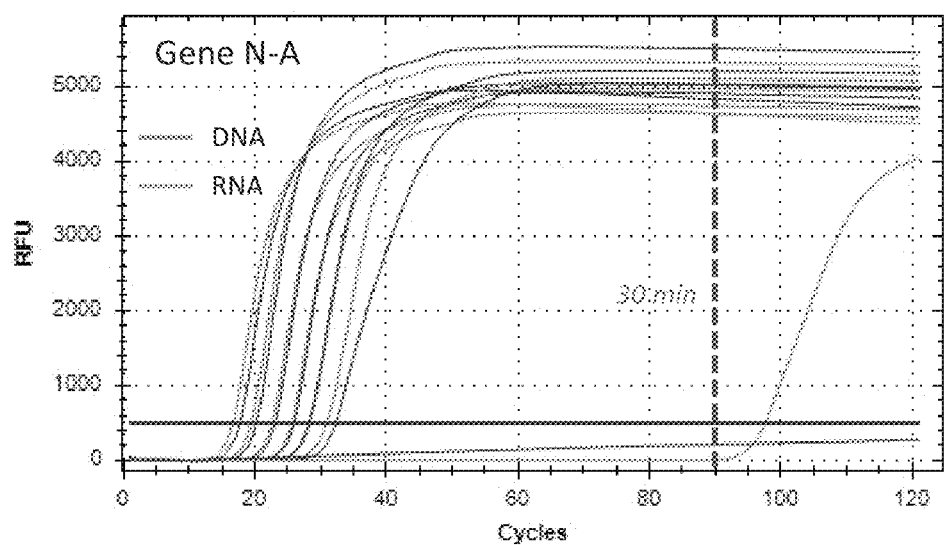
Figure 3A:
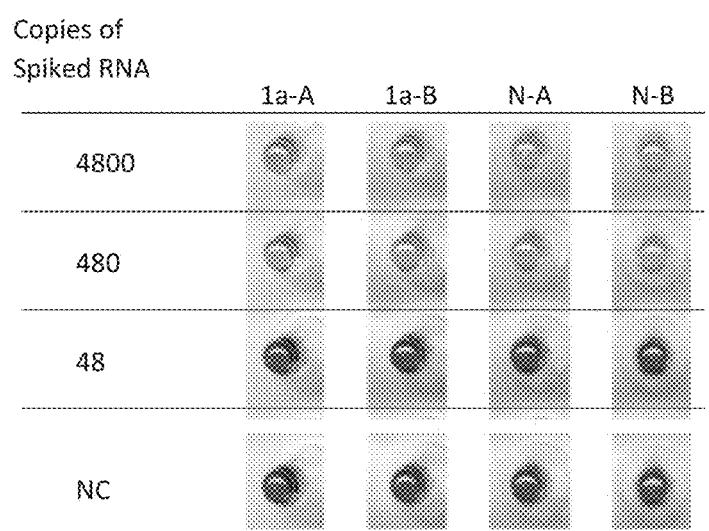
FIG. 3A and FIG. 3B shows that pH dependent colorimetric LAMP can detect viral genomes in total cell lysates and whole blood without requiring a purification step to remove total RNA. The primer sets described in Example 1 were used here. Lysis was performed using a cell lysis reagent (Luna® Cell Ready Lysis Module (New England Biolabs, Ipswich, Mass.)).
Figure 3B:
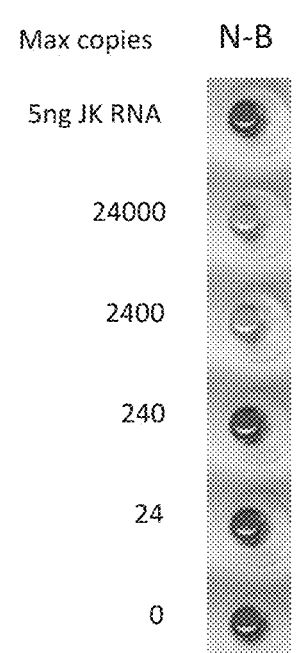

(5) For a rapid test for an infectious agent, it is desirable to analyze a sample directly from a swab or sample matrix containing test nucleic acid without requiring a purification step. Previously, it was shown that LAMP can detect 2-3 copies of a purified target DNA in a genome in under 30 minutes and 10 copies under 15 minutes (Tanner, et al. (2015) Biotechniques, 58, 59-68). FIG. 2A-FIG. 2B shows the sensitivity of assays described herein for nematode parasites as little as 0.01-0.1 picograms nematode DNA can be detected. FIG. 3A-FIG. 3B shows detection of 1.28 femtograms of DNA of a tick-borne pathogen from whole ticks. Embodiments of the test described herein for a target RNA of a virus in a nasal or oral swab can be performed within 15 minutes. Example 1 provides an example of pH dependent colorimetric LAMP as used for detection of viral pathogens such as RNA or DNA viruses for example, SARS-CoV-2 RNA. The results for SARS-CoV-2 RNA in FIG. 21-FIG. 27 show that the virus can be reliably detected at between 10-40 copies in under 60 minutes.

Preparation of Samples for Analysis

Biological material that may contain one or more pathogens can be sampled for one or more target nucleic acids in parallel to obtain distinctive results for each or together for purposes of efficiency initially but that might result in secondary tests. For example, where a sample is taken from a subject to test for SARS-CoV-2 and influenza, it might be desirable to perform tests in parallel using one or more primer sets that are specific for each target nucleic acid. Samples may be obtained from any biological source. For example, samples may be derived from blood (e.g. from a venous draw), serum, plasma, urine, feces, sputum, hair follicles, lavage, nasal, oral or buccal swabs, and/or saliva may be used for detecting the pathogen using pH dependent color LAMP or PAR dependent color LAMP that is not pH dependent. The samples may be dried, placed in an aqueous solution that may be selected from water or stored in a transport medium, for example saline, TE or a transport medium available from Copan (Murrieta, Calif.). Such products include Sputum Dipper™, SnotBuster™, UriSponge™ and UTM® Universal Transport System™.

One embodiment of the method utilizes a lysis buffer suitable for treating saliva among other biological materials. This was developed so as to replace swab based sampling from patients and moreover to remove the need for an intermediate polynucleotide purification step prior to an primer dependent amplification reaction.

Embodiments are provided for lysis buffers suitable for LAMP. The lysis buffer was prepared as a 2× mix but could also be prepared as a 4×, 5× or 10× mix or indeed any concentrated form limited only by possible undesirable precipitation of individual reagents at high concentrations. In one example, the 2× lysis mix described herein comprises 800 mM guanidine HCl, 4% Triton X-100, 80 mM TCEP and 150 mM LiCl at pH 8.0. This 2× lysis mix can be combined with an equal volume of saliva resulting in a final concentration of 400 mM guanidine HCl, 2% Triton X-100, 40 mM TCEP and 75 mM LiCl at pH 8.0. In one embodiment, it was shown that allowing the saliva-lysis mixture to stand at room temperature for 30 minutes increased the sensitivity and reliability of the subsequent LAMP reaction. Subsequent to incubation for 30 minutes at room temperature, the temperature of the mix was raised to 95° C. for 5 minutes or 75° C. for 20 minutes or 65° C. for 60 minutes. 2 μl of the saliva-lysis mix was then added to the standard master mix for LAMP along with primers. This protocol permitted.

Individual samples were tested herein in strip well tubes or 96 well plates with positive and negative outcomes observed by eye, and also with a spectrophotometer (SpectraMax) using dual wavelengths that captured signal from 560 nm (red) to 432 nm (yellow) from each 384 well plate. The data was then presented on a computer readout. The results particularly with a cooling step between the LAMP reaction and the reading of plates resulted in increased sensitivity in detecting as few as 20 copies of viral RNA/well in 100% of samples tested.

An example of an automated workflow from sample to collection to output was envisaged in FIG. 28A-FIG. 28F. Although there are many possibilities in the uses of robotic devices for individual steps, the exemplified workflow is predicted to have a capability to perform 100,000 reactions in 20 hours.

There is some flexibility based on the parameters described herein that will be apparent to a person of ordinary skill in the art as to one or more modifications selected from: the source of a sample from a patient; sample storage; sample lysis containing for example, guanidine salts, reducing agent and optionally detergent to provide RNA or DNA that may then be directly amplified or sequenced; the type of sequencing platform selected as to whether it is a single molecule sequencer such as Oxford Nanopore or a sequencer of libraries with adapters such as required by an Illumina sequencing platform; the type of amplification reaction selected according to a high through put time and cost efficient LAMP based reaction using appropriately selected single or multiple primer sets or an RT-qPCR real time slightly more sensitive but less time and cost efficient than LAMP; carry over prevention; the optimization of the amplification reactions with respect to pH, buffer content including guanidine salts, and concentration, of reagents; end point color change be it pH dependent or dependent on a chemical reaction or fluorescence; and a suitable reader for distinguishing positives from negative samples in a binary determination and a rapid read out.

LAMP sensitivity has been improved by reducing background and enhancing signal and these improvements can be followed through to the present assay. See for example: U.S. Pat. Nos. 9,121,046, 9,546,358, 9,074,249, 9,074,243, 9,157,073, and 9,127,258 in addition to U.S. Pat. Nos. 9,580,748, 9,034,606, and 10,597,647 all incorporated in entirety by reference. These modifications can be incorporated into the colorimetric LAMP assay described herein to improve the detection of pathogens even further. U.S. Pat. No. 10,253,357 is also incorporated by reference.

The diagnostic test of whether a pathogen is present in a sample can be scaled up without any difficulty so that any of 1-1000s of reactions can be performed at the same time. If the reactions are performed in 96 well dishes or in 1000 well dishes, a robot liquid handler can add master mix to each well and then the swab sample and a computer system can record the color changes and the location of the well testing positive. For individual or small numbers of samples, the reactions might be performed in microfuge or PCR tubes. The entire diagnostic test can be completed within 4 hours, for example in less than 3 hours, for example less than 2 hours, for example less than 1 hour from the time of taking the sample to obtaining a result. The diagnostic test can be performed in a doctor's office or even at home.

In certain embodiments the master mix including enzymes, dyes, primers and nucleotides may be dried onto a solid matrix such as paper so that addition of a measured droplet of the sample onto the paper and a heating step even on a surface heated by a homemade water bath, or small heating block that can be transported in a backpack for environmental use results in a color change to indicate a result. Alternatively, the master mix may be freeze dried or lyophilized and contained in a tube ready for addition of a sample in the home or clinic.

Embodiments include incorporating amplification reagents in a facemask possibly immobilized on beads such that when droplets of saliva containing virus contact the beads, fluorescence results from an isothermal amplification reaction. Whereas LAMP as described in embodiments herein requires a 65° C. temperature step, this requirement may be circumvented in the future for LAMP or by use of other isothermal amplification methods. Alternatively, the combination of a saliva droplet containing a virus particle interacting with immobilized regent on a bead might trigger an exothermic chemical reaction. The higher the virus load, the stronger the signal that would result from amplification. Alternatively, the signal from the production of hydrogen ions or change in flow of electrons (that result from amplification as pyrophosphates are released when dNTPs are incorporated during amplification reaction) that generates a visual signal might in turn trigger a sound wave that is amplified resulting in an audible sound. Such microelectronic technology already exists in a different formats and could be constructed using synthetic biology constructed circuits. An audible sound could alert the wearer of the mask of $3^{rd}$ party released virus without the need to remove the mask while a visual signal would alert others of the wearer of the mask being infected.

In one embodiment, a discrete portion of a face mask my contain a chamber containing lysis reagent in a dried or liquid form so that incoming saliva droplets will be lysed and the polynucleotides released.

Embodiments describing improvements in the LAMP reaction that include carryover prevention, RNase inhibition, enhancement of sensitivity and rate of the LAMP reaction by the use of guanidine salts and/or reduced NaCl or KCl in the buffer, selecting primer sets and multiplexing primer sets, lyophilization of reagents can be combined in any combination for purposes of automation of large numbers of assays for genomic studies, gene expression studies or epidemiology analysis as well as point of care and miniaturization of tests to act as environmental sensors of pathogens.

Unless otherwise defined, all technical and scientific terms used herein have the same meaning as commonly understood by one of ordinary skill in the art to which this disclosure belongs. Still, certain elements may be defined for the sake of clarity and ease of reference. It is also to be understood that the terminology used herein is for the purpose of describing particular embodiments only, and is not intended to be limiting, since the scope of the present teachings will be limited only by the appended claims.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular Biology, 2nd ed., John Wiley and Sons, New York (1994), and Hale & Markham, the Harper Collins Dictionary of Biology, Harper Perennial, N.Y. (1991) and the like.

As used herein and in the appended claims, the singular forms "a", "an", and "the" include plural referents unless the context clearly dictates otherwise. For example, the term "a protein" refers to one or more protein, i.e., a single protein and multiple proteins. It is further noted that the claims can be drafted to exclude any optional element.

Aspects of the present disclosure can be further understood in light of the embodiments, section headings, figures, descriptions, and examples, none of which should be construed as limiting the scope of the present disclosure in any way. Accordingly, the claims set forth below should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Numeric ranges are inclusive of the numbers defining the range. All numbers should be understood to encompass the midpoint of the integer above and below the integer i.e. the number 2 encompasses 1.5-2.5. The number 2.5 encompasses 2.45-2.55 etc. When sample numerical values are provided, they may represent, unless specified otherwise, an intermediate value in a range of values. If specified, an individual numerical value may represent an extreme point in a range. Where a plurality of numerical values are provided these may represent the extremes of a range unless specified. If specified, these values may represent intermediate values in a range.

The term "non-naturally occurring" as used herein refers to a composition that does not exist in nature. A "non-naturally occurring" protein may have an amino acid sequence that is different from a naturally occurring amino acid sequence for example, one or more amino acid substitutions, deletions or insertions at the N-terminus, the C-terminus and/or between the N- and C-termini of the protein. Hence the non-naturally occurring protein may have less than 100% sequence identity to the amino acid sequence of a naturally occurring protein although it may have at least 80%, at least 85%, at least 90%, at least 95%, at least 97%, at least 98%, at least 98.5% or at least 99% identity to the naturally occurring amino acid sequence. In certain cases, a non-naturally occurring protein may include a protein that has a post-translational modification pattern that is different from the protein in its natural state for example, an N-terminal methionine or may lack one or more post-translational modifications (e.g., glycosylation, 5 phosphorylation, etc.) if it is produced by a different (e.g., bacterial) cell.

In the context of a nucleic acid, the term "non-naturally occurring" refers to a nucleic acid that contains: a) a sequence of nucleotides that is different from a nucleic acid in its natural state (i.e., having less than 100% sequence identity to a naturally occurring nucleic acid sequence); b) one or more non-naturally occurring nucleotide monomers (which may result in a non-natural backbone or sugar that is not G, A, T or C); and/or c) may contain one or more other modifications (e.g., an added label or other moiety) to the 5'-end, the 3' end, and/or between the 5'- and 3'-ends of the nucleic acid.

In the context of a composition, the term "non-naturally occurring" refers to: (a) a combination of components that are not combined by nature, e.g., because they are at different locations, in different cells or different cell compartments; (b) a combination of components that have relative concentrations that are not found in nature; (c) a combination that lacks something that is usually associated with one of the components in nature; (d) a combination that is in a form that is not found in nature, e.g., dried, freeze dried, crystalline, aqueous; and/or (e) a combination that contains a component that is not found in nature. For example, a composition may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature. The non-naturally occurring polymerase may be purified so that it does not contain DNases, RNases or other proteins with undesirable enzyme activity or undesirable small molecules that could adversely affect the sample substrate or reaction kinetics.

All publications, patents, and patent applications mentioned in this specification are herein incorporated by reference to the same extent as if each individual publication, patent, or patent application was specifically and individually indicated to be incorporated by reference including: US Provisional Ser. Nos. 62/988,696, 63/001,909, 63/013,422, 63/022,303, 63/027,216, 63/048,556 and U.S. application Ser. No. 16/938,575.

Embodiments of the invention are summarized below.

1. A master mix comprising: a strand displacing polymerase suitable for Loop-Mediated Isothermal Amplification (LAMP) of DNA; dATP, dGTP, dCTP, and dTTP; at least one reagent that changes color or provides fluorescence if amplification occurs; wherein the master mix is either dried or in a weakly buffered solution at a starting pH which is measurably altered during amplification.
2. The master mix according to 1, immediately above, further comprising a reverse transcriptase.
3. The master mix according to 2, immediately above, wherein the reverse transcriptase in selected from an HIV derived reverse transcriptase, an intron expressed reverse transcriptase and a reverse transcriptase variant of mouse murine virus.
4. The master mix according to any of 1 through 3 above, wherein the starting pH is in the range of pH 7.5-pH 9.0.
5. The master mix according to 4, wherein the starting pH is preferably in the range of pH 7.8-pH 8.5.
6. The master mix according to any of 1 through 5, wherein the master mix is in a weakly buffered solution of 5 mM Tris or less.
7. The master mix according to any of 1 through 6, wherein the master mix further comprises an aptamer for regulating the activity of the strand displacing polymerase.
8. The master mix according to any of 1 through 7, wherein the master mix further comprises one or more RNase inhibitors.
9. The master mix according to 8, wherein the RNase inhibitors comprise an aptamer for inhibiting RNase A, an aptamer for inhibiting RNase I and/or a protein inhibitor of RNAse.
10. The master mix according to 1 through 9, further comprising at least one set of primers having specificity for a target nucleic acid.
11. The master mix according to 1 through 10, further comprising a plurality of sets of primers having specificity for a target nucleic acid.
12. The master mix according to 1 through 11, wherein the at least one reagent includes a dye that is pH sensitive and changes color after an amplification reaction in which the pH is altered.
13. The master mix according to 1 through 12 further comprising dUTP.

14. The master mix according to 1 through 13, wherein the at least one reagent includes a dye that is a metallochromic indicator.
15. The master mix according to 1 through 14, wherein the at least one reagent comprises a metallochromic dye and a fluorescent dye.
16. The master mix according to 1 through 15, wherein the metallochromic indicator is 4-(2-pyridylazo) resorcinol (PAR).
17. The master mix according to 1 through 16, wherein the master mix is freeze dried, air dried, or lyophilized.
18. The master mix according to 1 through 17, wherein the master mix is immobilized; such as wherein the master mix is immobilized on paper, or on a natural or synthetic polymer.
19. The master mix according to any of 1 through 16, wherein the master mix is in liquid form in a reaction container.
20. The master mix according to any of 1 through 19, further comprising dUTP.
21. A method for determining whether a target nucleic acid is present in a sample, comprising:
    (a) placing the sample into an aqueous solution in a container;
    (b) bringing an aliquot of the sample into contact with a master mix according to any of 1 through 20 to form a reaction mixture; and
    (c) determining whether the target nucleic acid is present in the sample by a change in the color or fluorescence of the mixture.
22. The method according to 21, wherein the sample is a clinical sample, such as a sample of a body fluid or a sample taken from a swab, an environmental sample, or a sample of purified nucleic acid.
23. The method of 21 or 22, wherein the target nucleic acid is:
    associated with a pathogen or is a diagnostic target for pathogenesis;
    associated with gene expression; or
    an indicator of a metabolic response to a pharmaceutical preparation or allergen.
24. The method of 23, wherein the target nucleic acid is an RNA.
25. The method according to 23 or 24, wherein the target nucleic acid is associated with a pathogen.
26. The method according to 25, wherein the pathogen is a virus.
27. The method according to 26, wherein the virus is an RNA virus.
28. The method of 21 or 22, wherein the target nucleic acid is DNA, and the method is for determining genetic loci correlated to a phenotype.
29. The method of 28, wherein the genetic loci are selected from the group consisting of a single nucleotide polymorphism (SNP) in a genome, an exon, or gene in the genome.
30. The method according to any of 21 through 29, wherein the container contains multiple compartments each for analyzing a separate sample.
31. The method according to any of 21 through 30, wherein the change in color or fluorescence of the mixture can be digitized and recorded by a computer.
32. A composition, comprising: one or more primer sets suitable for amplification, the primer sets having specificity for a single nucleic acid of interest; and a buffer containing a molecule comprising $C-(NH_2)_2NH^+$.
33. The composition according to 32, wherein the molecule comprising $C-(NH_2)_2NH^+$ is selected from guanidine hydrochloride, guanidine thiocyanate, arginine, and guanidine sulfate.
34. The composition according to 32 or 33, wherein the one or more primer sets are primer sets for Loop-Mediated Isothermal Amplification (LAMP).
35. The composition according to any of 32 through 34, wherein the one or more primer sets are two or three or four primer sets having specificity for a single nucleic acid.
36. The composition according to any of 32 through 36, further comprising one or more reagents selected from an RNAse inhibitor, a reverse transcriptase, a thermolabile Proteinase K, and a polymerase.
37. The composition according to any of 32 through 37, further comprising dNTPs; and optionally further comprising a reporter molecule for detecting amplification in the presence of a target nucleic acid.
38. The composition according to 37, wherein the reporter molecule comprises a metallochromic dye.
39. The composition according to 38, wherein the metallochromic indicator is 4-(2-pyridylazo) resorcinol (PAR).
40. A method of isothermal amplification (e.g. LAMP), comprising: (a) adding the composition according to any of 1 through 20, and 32 through 38, to a sample comprising a target nucleic acid; and (b) detecting whether the target nucleic acid is present in the sample.
41. A method for detecting a target nucleic acid in a biological sample, comprising:
    (a) treating the biological sample with a lysis mixture comprising a $C-(NH_2)_2NH^+$ salt, and a reducing agent; at an elevated temperature for an effective period of time;
    (b) adding an aliquot of the sample from (a) into a master mix according to any of 1 through 20;
    (c) incubating the mixture under conditions for Loop-mediated isothermal amplification (LAMP) to permit a color change in the presence of a detectable amount of a target nucleic acid; and
    (d) determining whether the sample contains the target nucleic acid.
42. The method according to 41, wherein the detectable amount is less than 100 copies of the target nucleic acid.
43. The method according to 41 or 42, wherein the $C-(NH_2)_2NH^+$ salt in the lysis mixture is a guanidine salt.
44. The method according to any of 41 through 43, wherein the guanidine salt is present in a 10× lysis buffer.
45. The method according to any of 41 through 44, further comprising increasing the sensitivity of detection by determining whether the sample contains the target nucleic acid using a dual wavelength spectrophotometer.
46. The method according to any of 41 through 45, wherein the elevated temperature in (a) is 95° C. and the effective time is 5 minutes.
47. The method according to any of 41 through 46, wherein (a) further comprises allowing the sample in the lysis mixture to incubate at room temperature before treating with an elevated temperature.
48. The method according to 47, wherein if the incubation time at room temperature is at least 30 minutes then the elevated temperature may be 75° C. or less, for a period of time that is 60 minutes or less.

49. The method according to any of 41 through 48, wherein the lysis mixture further comprises a detergent.

50. The method according to 49, wherein the detergent is Triton X.

51. A composition comprising: a guanidine salt, a reducing agent and detergent.

52. The composition according to 51, further comprising LiCl.

53. The composition according to 51 or 52, wherein the guanidine salt is guanidine hydrochloride (Guanidine HCl).

54. The composition according to any of 51 through 53, wherein the reducing agent is Triton X.

55. The composition according to any of 51 through 54, wherein the reducing agent is Tris(2-carboxyethyl) phosphine hydrochloride (TCEP).

56. The composition according to any of 51 through 55, further comprising a biological sample.

57. The composition according to any of 51 through 56, wherein the biological sample is saliva.

58. The composition according to any of 51 through 57, wherein the composition further comprises a master mix according to any of 1 through 20.

59. The composition according to any of 51 through 58, comprising at least one LAMP primer set.

60. The composition according to any of 51 through 59, wherein the at least one LAMP primer set is at least two different LAMP primer sets for detecting a single target.

61. The composition according to any of 51 through 60, wherein the composition further comprises a target polynucleotide.

62. The composition according to any of 51 through 61, wherein the target polynucleotide is a coronavirus RNA.

63. A method for preparing a biological sample for an amplification reaction; comprising:
   (a) obtaining a lysis mixture comprising guanidine salt, a reducing agent, and a detergent;
   (b) combining the lysis mixture in (a) with a biological sample containing a target polynucleotide to form a diagnostic sample; and
   (c) analyzing an aliquot of the diagnostic sample for identifying if the target polynucleotide is present and optionally determining the sequence of the target polynucleotide, wherein the step of analyzing is selected from one or more of (i) amplifying the target polynucleotide to detect the presence of a target polynucleotide by a change in color or fluorescence; (ii) amplifying the target polynucleotide and sequencing the amplified polynucleotides; and (iii) direct sequencing of an aliquot of the diagnostic sample.

64. A method according to 63, wherein a 2× lysis mixture comprises guanidine salt in the range of 300 mM-1.5 M guanidine hydrochloride, TritonX in the range of 1%-6%, and TCEP in the range of 40 mM-120 mM.

65. The method of 64, wherein the 2× lysis mixture further comprises LiCl. 66. The method of 65, wherein the LiCl is in the range of 50 mM-100 mM.

67. The method of any of 64 through 66, wherein the 2× lysis mixture comprises 800 mM guanidine hydrochloride, 4% Triton X and 80 mM TCEP.

68. The method of 67, wherein the 2× lysis mixture further comprises 150 mM LiCl.

69. The method of any of 63 through 68, wherein (b) further comprises increasing the temperature of the diagnostic sample to release the polynucleotides from biological material in the sample.

70. The method of 69, wherein the step of increasing the temperature further comprises raising the temperature in the range of 65° C.-95° C. wherein the time of incubation at the raised temperature is inversely proportional to the temperature.

71. The method of 69, wherein increasing the temperature further comprises raising the temperature to 75° C. for 20 minutes.

72. The method of 70, further comprises incubating the sample at room temperature for 30 minutes prior to increasing the temperature.

73. The method according to any of 63 through 72, wherein the step of amplifying further comprises amplifying the target polynucleotide by LAMP.

74. The method according to 73, wherein the LAMP is pH-dependent colorimetric LAMP.

75. The method according to 74, wherein the pH of the lysis mixture is at least pH 7.9 if the biological sample is saliva.

76. The method according to 63, wherein sequencing further comprises adding sample barcodes for large scale multiplexing of samples, wherein the bar code is added in the primer where amplification precedes sequencing or by ligation when the target polynucleotides are sequenced directly.

77. The method according to any of 40 through 48, and 63 through 75, further comprising a high throughput automated workflow for performing the steps of the method.

78. A kit comprising the master mix of any of 1 through 20, and/or the compositions of 32 through 39, and 51 through 62, wherein the kit optionally further comprises a heating block suitable for heating a reaction tube, plate, or paper, or a plurality of the same.

EXAMPLES

All reagents are commercially available and provided by New England Biolabs, Ipswich, Mass. unless otherwise specified. Although the examples are provided for the coronavirus they are also applicable to other pathogens and to the analysis of DNA and RNA.

Example 1: Identification of SARS, CoV-2 Virus RNA

SARS-CoV-2 virus RNA is analyzed directly from nasal swabs using a visual, colorimetric detection. This simple and sensitive method provides an opportunity to facilitate virus detection in the field without a requirement for complex diagnostic infrastructure. The general features of the method were reported in Tanner, et al. BioTechniques 58:59-68 (2015) and reagents for conducting the method are provided by New England Biolabs (M1800). Here the sensitivity of the method was tested for the Coronavirus described as SARS-CoV-2.

LAMP Primer Design and Testing 5 sets of LAMP oligonucleotide primers targeting two fragments (Table 1) of SARS-CoV-2 sequence (GenBank accession number MN908947) were designed using the online software Primer Explorer V5 (available for free use at: https://primerexplorer.jp/e/). The two fragments corresponded to the 5' region of the ORF1a gene and Gene N. Three sets of primers were designed to target ORF1 and two for GeneN. Each set of primers was tested with synthetic DNA substrates (gBlocks®, Integrated DNA Technologies, Coralville, Iowa) and RNA (in vitro transcribed RNA from that DNA) prior to clinical use.

TABLE 1

Sequences of amplicons and LAMP primers

| LAMP primer or Amplicon | Sequence |
|---|---|
| ORF1a | CCCTATGTGTTCATCAAACGTTCGGATGCTCGAACTGCACCTCATGGTCATGTTATGGTTGA (SEQ ID NO: 1) |
| Fragment | GCTGGTAGCAGAACTCGAAGGCATTCAGTACGGTCGTAGTGGTGAGACACTTGGTGTCCTT (SEQ ID NO: 2) |
|  | GTCCCTCATGTGGGCGAAATACCAGTGGCTTACCGCAAGGTTCTTCTTCGTAAGAACGGTA (SEQ ID NO: 3) |
|  | ATAAAGGAGCTGGTGGCCATAGTTACGGCGCCGATCTAAAGTCATTTGACTTAGGCGACGA (SEQ ID NO: 4) |
|  | GCTTGGCACTGATCCTTATGAAGA (SEQ ID NO: 5) |
| ORF1a-A |  |
| ORF1a-A-F3 | CTGCACCTCATGGTCATGTT (SEQ ID NO: 6) |
| ORF1a-A-B3 | AGCTCGTCGCCTAAGTCAA (SEQ ID NO: 7) |
| ORF1a-A-FIP | GAGGGACAAGGACACCAAGTGTATGGTTGAGCTGGTAGCAGA (SEQ ID NO: 8) |
| ORF1a-A-BIP | CCAGTGGCTTACCGCAAGGTTTTAGATCGGCGCCGTAAC (SEQ ID NO: 9) |
| ORF1a-A-LF | CCGTACTGAATGCCTTCGAGT (SEQ ID NO: 10) |
| ORF1a-A-LB | TTCGTAAGAACGGTAATAAAGGAGC (SEQ ID NO: 11) |
| ORF1a-B |  |
| ORF1a-B-F3 | TCATCAAACGTTCGGATGCT (SEQ ID NO: 12) |
| ORF1a-B-B3 | TATGGCCACCAGCTCCTT (SEQ ID NO: 13) |
| ORF1a-B-FIP | CGACCGTACTGAATGCCTTCGAGAACTGCACCTCATGGTCAT (SEQ ID NO: 14) |
| ORF1a-B-BIP | AGACACTTGGTGTCCTTGTCCCAGAAGAACCTTGCGGTAAGC (SEQ ID NO: 15) |
| ORF1a-B-LF | CTGCTACCAGCTCAACCATAAC (SEQ ID NO: 16) |
| ORF1a-B-LB | TCATGTGGGCGAAATACCAGT (SEQ ID NO: 17) |
| ORF1a-C |  |
| ORF1a-C-F3 | CTGCACCTCATGGTCATGTT (SEQ ID NO: 18) |
| ORF1a-C-B3 | GATCAGTGCCAAGCTCGTC (SEQ ID NO: 19) |
| ORF1a-C-FIP | GAGGGACAAGGACACCAAGTGTGGTAGCAGAACTCGAAGGC (SEQ ID NO: 20) |
| ORF1a-C-BIP | CCAGTGGCTTACCGCAAGGTTTTAGATCGGCGCCGTAAC (SEQ ID NO: 21) |
| ORF1a-C-LF | ACCACTACGACCGTACTGAAT (SEQ ID NO: 22) |
| ORF1a-C-LB | TTCGTAAGAACGGTAATAAAGGAGC (SEQ ID NO: 23) |
| Gene N | ATGACCAAATTGGCTACTACCGAAGAGCTACCAGACGAATTCGTGGTGGTGACGGTAAAAT (SEQ ID NO: 24) |
| fragment | GAAAGATCTCAGTCCAAGATGGTATTTCTACTACCTAGGAACTGGGCCAGAAGCTGGACTT (SEQ ID NO: 25) |
|  | CCCTATGGTGCTAACAAAGACGGCATCATATGGGTTGCAACTGAGGGAGCCTTGAATACAC (SEQ ID NO: 26) |
|  | CAAAAGATCACATTGGCACCCGCAATCCTGCTAACAATGCTGCAATCGTGCTAC (SEQ ID NO: 27) |

TABLE 1-continued

Sequences of amplicons and LAMP primers

| LAMP primer or Amplicon | Sequence |
|---|---|
| Gene N-A | |
| GeneN-A-F3 | TGGCTACTACCGAAGAGCT (SEQ ID NO: 28) |
| GeneN-A-B3 | TGCAGCATTGTTAGCAGGAT (SEQ ID NO: 29) |
| GeneN-A-FIP | TCTGGCCCAGTTCCTAGGTAGTCCAGACGAATTCGTGGTGG (SEQ ID NO: 30) |
| GeneN-A-BIP | AGACGGCATCATATGGGTTGCACGGGTGCCAATGTGATCT (SEQ ID NO: 31) |
| GeneN-A-LF | GGACTGAGATCTTTCATTTTACCGT (SEQ ID NO: 32) |
| GeneN-A-LB | ACTGAGGGAGCCTTGAATACA (SEQ ID NO: 33) |
| Gene N-B | |
| GeneN-B-F3 | ACCGAAGAGCTACCAGACG (SEQ ID NO: 34) |
| GeneN-B-B3 | TGCAGCATTGTTAGCAGGAT (SEQ ID NO: 35) |
| GeneN-B-FIP | TCTGGCCCAGTTCCTAGGTAGTTCGTGGTGGTGACGGTAA (SEQ ID NO: 36) |
| GeneN-B-BIP | AGACGGCATCATATGGGTTGCACGGGTGCCAATGTGATCT (SEQ ID NO: 37) |
| GeneN-B-LF | CCATCTTGGACTGAGATCTTTCATT (SEQ ID NO: 38) |
| GeneN-B-LB | ACTGAGGGAGCCTTGAATACA (SEQ ID NO: 39) |

These primers in a colorimetric LAMP assay were first tested on synthetic sequences corresponding to regions of the SARS-CoV-2 either as DNA or as RNA.

DNA fragments containing two SARS-CoV-2 sequences were synthesized as gBlocks. T7 RNA polymerase promoter sequences were added by PCR (M0493) (numbers indicate New England Biolabs, Inc. catalog ID numbers unless otherwise noted). The PCR reaction utilized primer pairs where one primer of the pair containing the T7 RNA promoter sequence. The PCR amplicon was then transcribed by in vitro transcription (E2050) to produce RNA with sequences that mimicked the selected portions of the SARS-CoV-2 virus. This RNA was purified using RNA clean up columns (T2040). The resulting RNAs as well as the corresponding gBlocks DNA were serially diluted in 10-fold increments using 0.1× TE buffer containing 0.01% Tween 20.

RT-LAMP reactions (for RNA) and LAMP (for DNA) using fluorescent dyes were performed using WarmStart Colorimetric LAMP 2× master mix (for DNA & RNA) (NEB product M1800) supplemented with 1 µM SYTO 9 fluorescent double-stranded DNA binding dye (Thermo Fisher Scientific, Waltham, Mass. (S34854)) and incubated on a real-time qPCR machine (CFX96) Bio-Rad, Hercules, Calif.)) for 120 cycles with 15 seconds each cycle (total ~40 minutes). This was performed to measure amplification in real time continuously over a 40 minute time period. This was done to confirm that amplification corresponded to color change and provide correlations between input and color change.

The colorimetric LAMP assay was first described in U.S. Pat. Nos. 9,034,606, 9,580,748 and US 2019/0169683 herein incorporated by reference. A weak buffer was described for use in the assay as described.

All LAMP assays were performed in a 20 µl reaction mixture containing 2 µL of 10× primer mix of 16 µM (each) of Forward Inner Primer (FIP) and Backward Inner Primer (BIP), 2 µM (each) of F3 and B3 primers, 4 µM (each) of Forward Loop (LF) and Backward Loop (LB) primers, 10 µl of WarmStart Colorimetric Lamp 2× master mix (M1800) 5 µl of DNAse, RNase free water and 3 µl of target RNA. Individual primer pair sets that were optimal (where one set includes 6 primers) were selected for ORF1 and Gene N.

TABLE 2

| Primer | 10X concentration | 1X concentration |
|---|---|---|
| FIP | 16 µM | 1.6 µM |
| BIP | 16 µM | 1.6 µM |
| F3 | 2 µM | 0.2 µM |
| B3 | 2 µM | 0.2 µM |
| Loop F | 4 µM | 0.4 µM |
| Loop B | 4 µM | 0.4 µM |

TABLE 3

| | DNA target | RNA target detection | No Template control (NTC) |
|---|---|---|---|
| WarmStart Colorimetric LAMP 2X master mix | 12.5 µl | 12.5 µl | 12.5 µl |
| LAMP Primer Mix (10X) | 2.5 µl | 2.5 µl | 2.5 µl |
| Target DNA | 1 µl | — | — |
| Target RNA | — | 1 µl | — |
| dH₂O | 9 µl | 9 µl | 10 µl |
| Total volume | 25 µl | 25 µl | 25 µl |

Note: Make primer stock in molecular biology grade H₂O rather than TE or other buffer in order to avoid carryover of additional buffer to the LAMP reaction. Prepare primer stocks in nuclease free water and store at −20° C. for up to 2 years.

Instructions from the New England Biolabs website (www.neb.com) were generally followed unless stated otherwise: 24 µl of the 2× master mix, plus primers and dH₂O were added into each desired reaction vessels and 1 µl of sample was added. After mixing, the reaction solutions were confirmed to have a bright pink color, indicating an initial high pH required for successful pH-LAMP reaction. The reaction mixture was incubated at 65° C. for 30 minutes. The tubes or vessels were then examined by eye to determine positive reactions that turned yellow or negative reactions that remained pink. Reactions can be examined earlier if desired. High copy or input reactions can exhibit full color change in as little as 10-15 minutes after incubation at 65° C. The color was visible directly on removal from the incubation temperature and could be intensified by allowing reaction to cool to room temperature. The result were photographed or scanned to record the colorimetric results, or simply kept at room temperature in the reaction vessel.

For Identification of SARS-CoV-2 virus RNA in test samples and determining the sensitivity of the assay, positive control test samples were prepared as follows: synthetic viral RNAs were spiked into Hela cells, which were then diluted and lysed using Luna Cell Ready Lysis Module. Each lysate was then diluted 10× with 0.1×TE+0.01% Tween 20 and 1 µL was added to standard colorimetric LAMP reactions.

For compatibility with blood recovery, the synthetic RNA described above was spiked into 200 µl whole human blood (Quadrant Health Strategies, Beverly, Mass.) and then purified the total blood RNA using Monarch Total RNA Miniprep Kit (T2010).

The results of pH dependent detection sensitivity assays showed that all five primer sets provided similar detection sensitivity and could consistently detect as low as 120 copies of the viral RNA (or 4.8 copies/µL) as determined by serial dilution of ~120 million copies down to ~120 copies (per 25 µL reaction) at 10-fold intervals in the colorimetric LAMP reactions. The relative efficiency of pH dependent colorimetric LAMP using RNA or DNA targets was determined from the real time LAMP signal using synthetic RNA with similarly diluted gBlock dsDNA. For the 2 primer sets we compared, one showed slightly slower amplification and detection of RNA template while the other appeared slightly faster, confirming the RNA is efficiently converted to cDNA by the reverse transcriptase (WarmStart RTx) and subsequently amplified via LAMP by the DNA-dependent DNA polymerase (Bst 2.0 WarmStart). This result was not adversely affected by the presence of UDP in the master mix to prevent carryover.

Example 2: Analysis of Total RNA from Crude Lysates for Identification of SARS-CoV-2 (COVID-19) Virus RNA Crude cell lysate was used in order to avoid an RNA purification step. The results indicated that about 480 copies were detected with four of the five primer sets tested in Example 1, showing a similar sensitivity as the detection sensitivity with synthetic RNA alone (FIG. 3A) with no interference by the lysate to either the amplification efficiency or visual color change. A mock experiment was set up during purification of total RNA to determine whether the synthetic RNA spiked into biological sample could be recovered. Various amounts of synthetic RNA were spiked into whole human blood and total blood RNA was purified. We were able to recover and detect the spiked RNA (FIG. 3B), indicating the total RNA did not cause detectable interference during the purification or the detection process. While the column-based approach is less compatible with the simple, field detection enabled by colorimetric LAMP, this is a typical laboratory workflow and can be used with simple isothermal amplification in a similar fashion to more expensive and involved qPCR detection workflows.

Example 3: Nucleic Acid Carryover Prevention

Figure 6A:
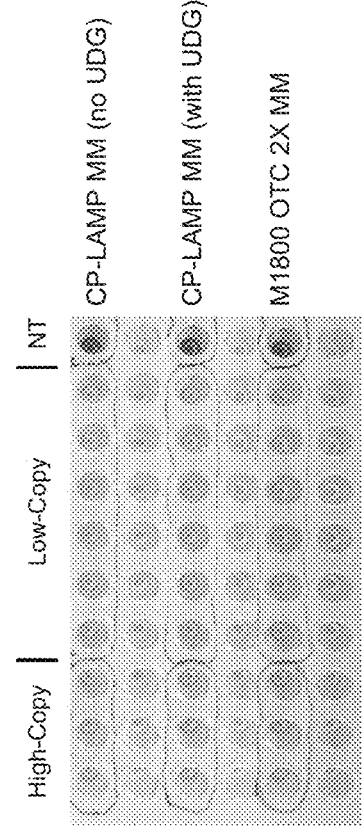
FIG. 6A shows that pH-dependent colorimetric LAMP sensitivity for the target nucleic acid is unaffected by the presence of dUTP and UDG. The endpoint color change with target nucleic acid in two Carryover Prevention Warm-Start® Colorimetric LAMP 2× master mixes (abbreviated CP-LAMP MM) (New England Biolabs, Ipswich, Mass.) is shown. Two CP-LAMP MM contained a 50/50 mixture of dUTP/dTTP replacing dTTP. One CP-LAMP MM did not contain UDG (no UDG). One CP-LAMP MM (with UDG) includes 0.02 U/µL thermolabile uracil DNA glycosylase (UDG) (New England Biolabs, Ipswich, Mass.). A third LAMP MM contained neither UDG nor dUTP. In all other respects the same protocols were followed as described in Example 1 and in the figures above.

Using the colorimetric LAMP assay described in Example 1, the benefit of using a thermolabile UDG and a 50:50 dTTP: dUTP in addition to dCTP, dGTP and dATP was demonstrated. FIG. 6A shows that this change in reagents did not affect the sensitivity or the specificity of the assay. Moreover, these additions to the master mix were effective in removing carryover nucleic acids from one sample to the next.

More specifically: two Carryover Prevention WarmStart Colorimetric LAMP 2× master mixes (abbreviated CP-LAMP MM) were developed and evaluated in an RT-LAMP functional assay, to determine whether the carryover additives interfered with the detection reaction as follows:

Each RT-LAMP reaction contained 1×CP-LAMP MM (no UDG or with UDG), 1×LAMP primers, genomic RNA, and 1×LAMP fluorescent dye in a reaction volume of 25 µl. High-copy reactions (n=3) contained 10 ng genomic RNA; low-copy reactions (n=6) contain 0.3 ng genomic RNA; and no-template (NT) reactions (n=1) contain no RNA. The plate was incubated at 65° C. for 75 minutes in a qPCR instrument, then imaged in a flatbed fluorescence scanner. The results are shown in FIG. 6A. A control was added as shown which had neither dUTP or UDG. No difference was observed between control and samples with the carryover prevention additives.

Figure 6B:
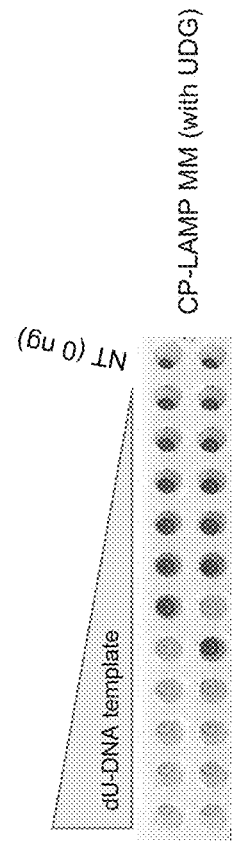
FIG. 6B shows that carryover of polynucleotide substrate is effectively prevented by including dUTP in the LAMP reaction. It was shown that over 10 fold dilutions of the dU template from a first sample to a second master mix that does not contain any target nucleic acid, carryover was prevented. Each sample from left to right is a 10 fold dilution of the previous sample. At 50 fold-60 fold dilution, the carryover material was destroyed by the thermolabile UDG (0.02 U/μl). Carryover prevention (CP) was determined in CP-LAMP MM.

Carryover prevention was effective as demonstrated in FIG. 6B.

Each RT-LAMP reaction contained 1×CP-LAMP MM (with UDG), 1×LAMP primers, genomic RNA, and 1×LAMP fluorescent dye in a reaction volume of 25 µl. Both rows were identical replicates. The first well in each row contained approximately 1 ng (1000 pg) of genomic RNA. From the second well onwards, 10-fold dilutions were completed, with the last well in each row serving as a no-template (NT) reaction with no RNA. The plate was incubated at 65° C. for 75 minutes in a qPCR instrument, then imaged in a flatbed fluorescence scanner. No amplified product was observed in amounts where carryover occurs.

Example 4: Nasal Sampling for Detecting SARS-CoV-2

Nasal samples are collected by swab and placed in sterile water in a microfuge tube. An aliquot of the sample is then combined with a master mix prepared as described above (see Example 3). Thermolabile UDG (New England Biolabs, Ipswich, Mass.) is added according to the manufacturer's instructions. Four primer sets from Table 1 described in Example 2 can be used here although a single set of primers for each of ORF1 and GeneN is sufficient. Modifications of the primers described in Table 1 can also be utilized. Other regions in the virus may be additionally or alternatively utilized. The reaction mixture is then heated to a temperature of about 65° C. using a temperature block for 15-60 minutes at which time the amplification is complete. The color of the reaction is then reviewed to reveal the presence or absence of the target nucleic acid. The entire reaction is amenable to substantial scaling up and can be executed in less than 1 hour from collection of sample to receiving the results.

Example 5: Colorimetric LAMP Using Lyophilized Colorimetric LAMP Mix

2× master mix (2×MM) for colorimetric LAMP was prepared using standard concentrations of LAMP reaction components described above (Bst 2.0 and RTx enzymes, aptamers to both, nucleotides, pH dependent dye, salt, detergent in a weakly buffered solution) together with 150 mM Trehalose, glycerol-free WarmStart RTx and high concentrations of WarmStart Bst 2.0. Extra KOH was added to half of the mix to increase the pH of the 2×MM to pH 8.2 from pH 8.0. To determine whether LAMP activity of the 2×MM were the same at both pHs for lyophilized samples stored at room temperature and aqueous samples stored at −20° C., 12.5 µl of 2×MM at pH 8.0 and 12.5 µl of the 2×MM at pH 8.2 were lyophilized and an equal volume of 2×MM at the different pHs in liquid form were stored at −20° C. Lyophilization (freeze drying) was performed under standard conditions (see for example, Millrock Technologies, NY, Labogene Denmark). The lyophilized 2×MMs were reconstituted with 12.5 µl H$_2$O and the pH was measured. The pH in the reconstituted 2×MM was found to have decreased by about 0.25 units. The reconstituted 2×MM and the 2×MM previously stored at −20° C. were then added to 12.5 µl of primer/template mix and 1 µM dsDNA binding fluorescent dye (SYTO 9). The primer set for HMBS2 was used for RT-LAMP and the template was contained in Jurkat total RNA at 10 ng or 0.3 ng. The reaction was incubated in a Bio-Rad IQ™ 5 Real Time PCR machine (Bio-Rad, Hercules, Calif.) to monitor the speed of the reaction and colorimetric or fluorometric detection of amplicons at the end of a 45 minute incubation at 65° C.

Figure 7:
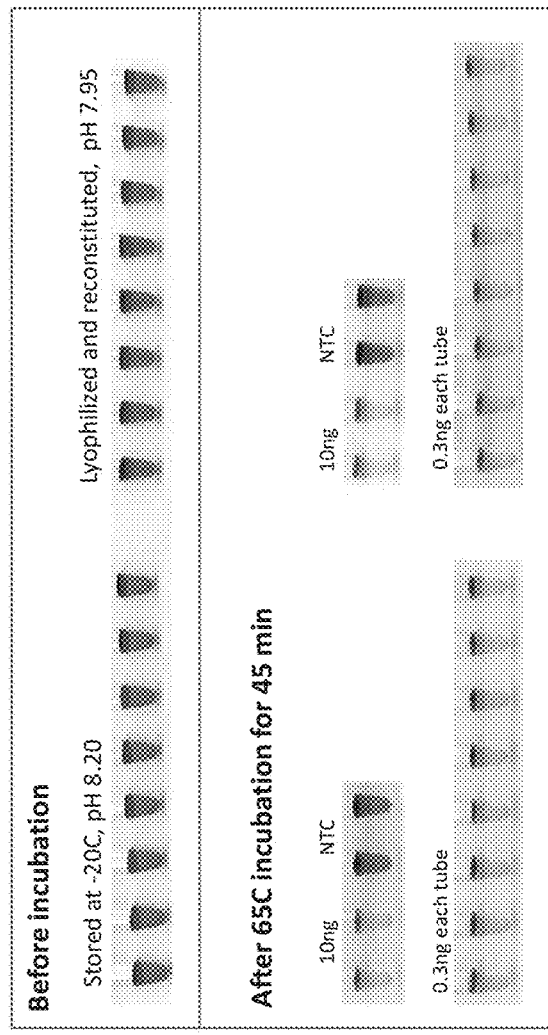
FIG. 7 shows that lyophilized pH-dependent LAMP MM is equally effective when added to a reaction mixture as non-lyophilized LAMP MM stored at −20° C. The starting pH of the lyophilized LAMP when reconstituted was reduced by 0.25 units in this example.
Figure 9A:
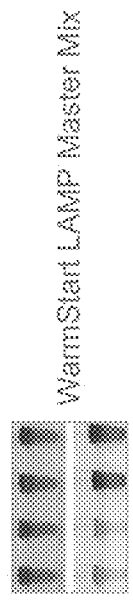
FIG. 9A-FIG. 9C shows that no difference in sensitivity of the LAMP reaction was observed using a LAMP MM versus −20° C. stored LAMP MM for DNA and RNA analyses, where RNA analysis additionally required a reverse transcriptase in the MM.
Figure 9C:
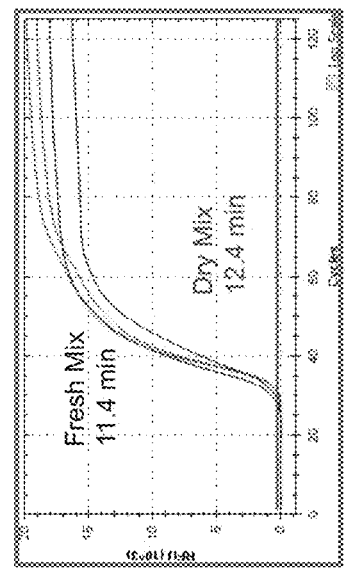
Figure 9B:
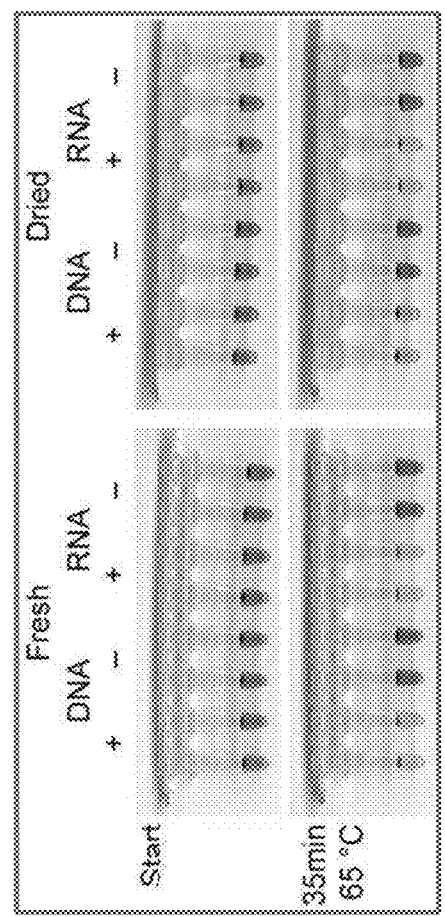
Figure 10:
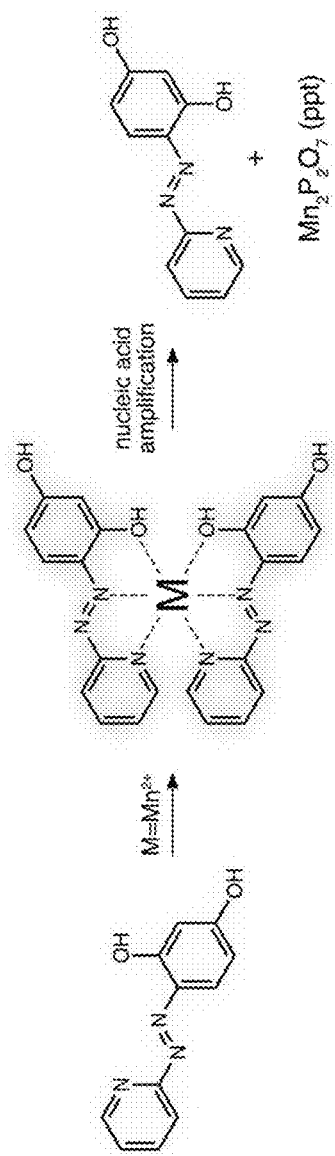
FIG. 10 shows the mechanism of the non-pH dependent colorimetric response for PAR. PAR is a known metallochromic indicator which, in the absence of metals in solution, exhibits a yellow color. When complexed with manganese in solution PAR produces a red color. During the nucleic acid amplification process, pyrophosphate is produced as a by-product of primer nucleic acid polymerization. By including a small amount of manganese ions in an amplification reaction, PAR is initially complexed with the metal and therefore in a red-colored state. The pyrophosphate by-product sequesters manganese with a higher affinity than does PAR, resulting in the dissociation of Mn from PAR and thereby returning PAR to a yellow-colored state.

Results: both batches (initial pH 8.0 or pH 8.2, only the data from the pH 8.2 batch is shown) worked well after lyophilization. There was no difference in colorimetric detection (FIG. 7, and FIG. 9A-FIG. 9B) or real time detection (FIG. 8A-8C and FIG. 9C) with either high or low amount of template in the RT-LAMP.

Example 6: PAR-Based Colorimetric Detection of Nucleic Acid Amplification is an Effective Alternative to pH Dependent Colorimetric LAMP A standard 2×LAMP master mix was prepared (see Example 1) and added to DNA so that the reaction mix contained using the following DNA polymerases in separate reactions: Bst LF, Bst 3.0, Bst 2.0 or WarmStart Bst 2.0 (all products from New England Biolabs, Ipswich, Mass.) in standard amplification buffer containing Tris-HCl, pH 8.8 at 25° C.; (NH$_4$)$_2$SO$_4$; KCl; MgSO$_4$. The buffer was varied from 0-4% Triton X-100. PAR concentration was varied from 250 µM to 50 µM PAR with results shown for 150 µM, 100 µM, 75 µM and 50 µM (FIG. 13). MnCl$_2$ was used throughout at concentrations in the range of 0.4 mM-1.6 mM. In FIG. 13, the reactions shown contained 0.5 µM MnCl$_2$. The LAMP primer set was BRCA2b including FIP/BIP/F3/B3/LF/LB (see below). 1 µl Hela genomic DNA (100 ng/µl) was used in the positive samples and no DNA in the controls. The reaction was performed at 65° C. for 1 hour. A positive endpoint was yellow corresponding to the reaction of manganese with pyrophosphate. The negative control was orange corresponding to the reaction of manganese with PAR.

TABLE 4

Primers for PAR-based colorimetric test

| | |
|---|---|
| BRCAb_F3 | TCCTTGAACTTTGGTCTCC (SEQ ID NO: 40) |
| BRCAb_B3 | CAGTTCATAAAGGAATTGATAGC (SEQ ID NO: 41) |

TABLE 4-continued

Primers for PAR-based colorimetric test

| | |
|---|---|
| BRCAb_FIP | ATCCCCAGTCTGTGAAATTGGGCAAAATGCTGGGA TTATAGATGT (SEQ ID NO: 42) |
| BRCAb_BIP | GCAGCAGAAAGATTATTAACTTGGGCAGTTGGTAA GTAAATGGAAGA (SEQ ID NO: 43) |
| BRCAb_LF | AGAACCAGAGGCCAGGCGAG (SEQ ID NO: 44) |
| BRCAb_LB | AGGCAGATAGGCTTAGACTCAA (SEQ ID NO: 45) |

Example 7: Non-Ionic Detergent Increases the Positive Signal in a LAMP Reaction Using PAR to Detect Sample An example of a non-ionic detergent (Triton X-100) was added to the LAMP 2× master mix containing PAR. In this example, the reaction mix contained Bst 2.0, PAR (200 µM), Manganese (0.8 mM), Isothermal amplification buffer with 2% Triton X-100, the BRCA 2b primer set as used in Example 5 and 1 µl Hela gDNA. Although the beneficial effect of adding Triton X-100 to the colorimetric PAR LAMP reaction is shown here, any non-ionic detergent from the Triton series or from the Brij series is expected to show similar benefits. The results are shown in FIG. 11A-11B. 2% Triton X-100 was used in FIG. 14 to provide enhanced signal without adversely affecting polymerase activity although 1%-3% Triton X-100 also showed enhanced signal in visible wave lengths in FIG. 13.

Example 8: Guanidine Hydrochloride Significantly Increases the Rate of Isothermal Amplification Reactions (a) LAMP Guanidine hydrochloride (10 mM-60 mM) not only increased the rate of the LAMP reaction performed according to Example 1, but also improved the limit of detection sensitivity (see FIG. 16, FIG. 17A-17C and FIG. 18A-18D).
  (i) BRCA and CFTR detection: Standard LAMP amplification was performed in 1× ThermoPol buffer and Bst 2.0 DNA polymerase at 65° C. using 10 ng of genomic DNA isolated from Hela cells as the target nucleic acid. Two amplification targets were tested: BRCA gene fragment and CFTR gene fragment. Guanidine hydrochloride at a final concentration of 0 mM-60 mM were added to the reactions. The amplification reactions contained 1 µM dsDNA binding dye-SYTO 9 and the reaction was performed and the reaction speed was monitored on a Bio-Rad IQ5 Real Time PCR machine.
  (ii) SARS-CoV-2 detection: single primer set in a single LAMP assay: As shown in FIG. 16, guanidine significantly increased the LAMP reaction speed for both primer sets with optimal concentration range between 20 mM-40 mM for primer sets 3 and 4 for Corona virus detection. The primer sets were tested against an AccuPlex™ SARS-CoV-2 Verification Panel (SeraCare Milford, Mass.) where the viral RNA is contained in a noninfectious viral protein coat.
  (iii) SARS-CoV-2 detection: multiple primer sets in a single LAMP assay Multiple primers used in a single LAMP reaction improved the sensitivity of colorimetric LAMP reactions.

For example, when primer set 3 and 4 were used together, sensitivity of the LAMP assay increased (see FIG. 19A-19C).

| Primer set 1 or 5: Asle/Orf1a (5'-3') SEQ ID. NO: 46-51: | |
|---|---|
| Asle_F3 | CGGTGGACAAATTGTCAC (SEQ ID NO: 46) |
| Asle_B3 | CTTCTCTGGATTTAACACACTT (SEQ ID NO: 47) |
| Asle_LF | TTACAAGCTTAAAGAATGTCTGAACACT (SEQ ID NO: 48) |
| Asle_LB | TTGAATTTAGGTGAAACATTTGTCACG (SEQ ID NO: 49) |
| Asle_FIP | TCAGCACACAAAGCCAAAAATTTATTTTTCTGTGCAAA GGAAATTAAGGAG (SEQ ID NO: 50) |
| Asle_BIP | TATTGGTGGAGCTAAACTTAAAGCCTTTTCTGTACAAT CCCTTTGAGTG (SEQ ID NO: 51) |

| Primer Set 2: Gene N-A (5'-3') SEQ ID NO: 28-33: | |
|---|---|
| GeneN-F3 | TGGCTACTACCGAAGAGCT (SEQ ID NO: 28) |
| GeneN-B3 | TGCAGCATTGTTAGCAGGAT (SEQ ID NO: 29) |
| GeneN-FIP | TCTGGCCCAGTTCCTAGGTAGTCCAGACGAATTCG TGGTGG (SEQ ID NO: 30) |
| GeneN-BIP | AGACGGCATCATATGGGTTGCACGGGTGCCAATGT GATCT (SEQ ID NO: 31) |
| GeneN-LoopF | GGACTGAGATCTTTCATTTTACCGT (SEQ ID NO: 32) |
| GeneN-LoopB | ACTGAGGGAGCCTTGAATACA (SEQ ID NO: 33) |

| Primer set 3 Gene N-2 | |
|---|---|
| N2-F3 | ACCAGGAACTAATCAGACAAG (SEQ ID NO: 52) |
| N2-B3 | GACTTGATCTTTGAAATTTGGATCT (SEQ ID NO: 53) |
| N2-FIP | TTCCGAAGAACGCTGAAGCG-GAACTGATTACAAACATTGG CC (SEQ ID NO: 54) |
| N2-BIP | CGCATTGGCATGGAAGTCAC-AATTTGATGGCACCTGTGTA (SEQ ID NO: 55) |
| N2-LF | GGGGGCAAATTGTGCAATTTG (SEQ ID NO: 56) |
| N2-LB | CTTCGGGAACGTGGTTGACC (SEQ ID NO: 57) |

| Primer set 4 Gene E | |
|---|---|
| E1-F3 | TGAGTACGAACTTATGTACTCAT (SEQ ID NO: 58) |
| E1-B3 | TTCAGATTTTTAACACGAGAGT (SEQ ID NO: 59) |
| E1-FIP | ACCACGAAAGCAAGAAAAAGAAGTTCGTTTCGGAAGAGA CAG (SEQ ID NO: 60) |
| E1-BIP | TTGCTAGTTACACTAGCCATCCTTAGGTTTTACAAGACT CACGT (SEQ ID NO: 61) |

-continued

| Primer set 4 Gene E | |
|---|---|
| E1-LB | GCGCTTCGATTGTGTGCGT (SEQ ID NO: 62) |
| E1-LF | CGCTATTAACTATTAACG (SEQ ID NO: 63) |

| Primer set 1 or 5: Asle/Orf1a (5'-3') SEQ ID. NO: 46-51: | |
|---|---|
| Asle_F3 | CGGTGGACAAATTGTCAC (SEQ ID NO: 46) |
| Asle_B3 | CTTCTCTGGATTTAACACACTT (SEQ ID NO: 47) |
| Asle_LF | TTACAAGCTTAAAGAATGTCTGAACACT (SEQ ID NO: 48) |
| Asle_LB | TTGAATTTAGGTGAAACATTTGTCACG (SEQ ID NO: 49) |
| Asle_FIP | TCAGCACACAAAGCCAAAAATTTATTTTTCTGTGCAAA GGAAATTAAGGAG (SEQ ID NO: 50) |
| Asle_BIP | TATTGGTGGAGCTAAACTTAAAGCCTTTTCTGTACAAT CCCTTTGAGTG (SEQ ID NO: 51) |

In addition, similar effect was observed with Bst DNA polymerase, large fragment, Bst 3.0, and in a RT-LAMP with RTx or AMV reverse transcriptase.

We also tested several related compounds containing the guanidine moiety (guanidinium compounds) and found that they also increased the rate of LAMP. The compounds tested included Guanidine thiocyanate, Guanidine chloride and Guanidine sulfate (see FIG. 15).

The observed increase in rate of a LAMP reaction could be further enhanced in the presence of varying amounts of salt concentrations. LAMP reactions were set up in ThermoPol buffer (10 mM KCl) for Bst2.0 (see FIG. 17B or in isothermal amplification buffer (50 mM KCl) for Bst 3.0 (see FIG. 17C) using a lambdal primer set with 0.5 ng lambda DNA with or without 30 mM guanidine hydrochloride. Addition of guanidine stimulated the LAMP amplification rate significantly at the lower end of the KCl concentration both with Bst 2.0 and Bst 3.0.

(b) Helicase-Dependent Amplification (HDA)

Standard HDA in IsoAmp II kit (H0110) was performed using 0.1 ng plasmid provided in the kit but added guanidine hydrochloride at a final concentration of 0 mM –60 mM. The reactions were performed at 65° C. and EvaGreen dye was included to monitor the progression of amplification. The Tt (time to threshold) was used to estimate the rate of amplification. It was shown to be 5 minutes shorter than standard HDA reactions. It was concluded that guanidine HCl increase melt temp for 0.5° C. per 10 mM up to 60 mM guanidine hydrochloride. Isothermal reactions were monitored in the presence of reduced NaCl in the buffer. Increased rates were observed when NaCl was reduced from the standard amount of 40 mM to 10 mM NaCl. Less NaCl gave a higher RFU signal (see FIG. 17A).

Example 9: Detection of Polynucleotides in Saliva Samples Using pH-Dependent Colorimetric LAMP Below is an example of the use of a lysis buffer suitable for directly assaying saliva samples in a pH dependent colorimetric LAMP. The workflow from saliva collection to LAMP analysis is shown in FIG. 20.

The lysis buffer was tested to determine an optimal formula for enhanced sensitivity of a LAMP assay for SARS-CoV-2.

(a) A lysis buffer containing guanidine hydrochloride (GnHCL) (Millipore Sigma, Burlington, Mass.) was tested at various concentrations in the range of 10 mM-400 mM (1×) in combination with 1 mM, 4 mM and 8 mM Tris(2-carboxyethyl)phosphine hydrochloride (TCEP)(Millipore Sigma, Burlington, Mass.) (1×) with or without 75 mM LiCl (New England Biolabs, Ipswich, Mass. 620151) (1×) against a SARS-CoV-2 virus titer that was varied for different samples containing 5,000 cps/ml, 10,000 cps/ml, 20,000 cps/ml or 40,000 cps/ml (from a stock solution of 100,000 cps/ml from SeraCare, Milford, Mass.). The virus was spiked into saliva of 20 µl, 30 µl, 35 µl and 37.5 µl volumes with TCEP and GnHCL. Copies of actin RNA at 100 copies/µl saliva was used as a control. Lysis of the virus in saliva added to the saliva lysis mix occurred at 95° C. for 5 minutes (the 10× lysis buffer contained 100 mM-4 M GnHCL, 10 mM-80 mM TCEP and 750 mM LiCl)

N2+E1 primer sets were added to a LAMP master mix (New England Biolabs, Ipswich, Mass.) containing reverse transcriptase to amplify CV-19 virus derived RNA.

Some of the results are shown in FIG. 21A and FIG. 21B (400 mM GnHCL and varying TCEP concentration, pH and LiCl concentration for 20,000 cps/ml where final concentrations are given), FIG. 22 showing the effect of increasing the concentration of TCEP, and FIG. 23A-FIG. 23D where the LAMP reaction time was varied from 35 minutes to 60 minutes with and without LiCl.

The following conditions provided 100% detection from 16 samples (16/16) containing 40 virus particles/sample under the following conditions for 10× lysis buffer: 4M GnHCL, 40 mM TCEP and 750 mM LiCl pH 8.5 µl of buffer was combined with 45 µl of sample (35 µl saliva spiked with 10 µl of SeraCare). After a heating step at 95° C. for 5 minutes, 2 µl of the treated saliva sample was then added to 18 µl of a LAMP master mix (10 µl of 2× stock from New England Biolabs, Ipswich, Mass. product M1800, 0.8 µl 25× primer set N2 and 0.8 µl 25× primer set E1, 0.4 µl 50× dye and 6 µl water to a total of 18 µl) and incubated at 65° C. for 35 minutes. The lysis buffer was found to be compatible with colorimetric LAMP (FIG. 21A-21D to FIG. 23A-23D), fluorescent LAMP and RT-qPCR (FIG. 24). It should be noted that where a lysis buffer is used that contained guanidine salt, it was not necessary to add the guanidine salt to the master mix because of the carryover of this salt from the lysis buffer.

| Control Primer Sequences: hActin (5'-3') | |
|---|---|
| ACTB-F3 | AGTACCCCATCGAGCACG (SEQ ID NO: 64) |
| ACTB-B3 | AGCCTGGATAGCAACGTACA (SEQ ID NO: 65) |
| ACTB-FIP | GAGCCACACGCAGCTCATTGTATCACCAACTGGGACGACA (SEQ ID NO: 66) |
| ACTB-BIP | CTGAACCCCAAGGCCAACCGGCTGGGGTGTTGAAGGTC (SEQ ID NO: 67) |

| Control Primer Sequences: hActin (5'-3') | |
|---|---|
| ACTB-LoopF | TGTGGTGCCAGATTTTCTCCA (SEQ ID NO: 68) |
| ACTB-LoopB | CGAGAAGATGACCCAGATCATGT (SEQ ID NO: 69) |

(b) Lysis buffer containing detergent.

Example 10: Detection of Polynucleotides in Saliva Samples Using RT-qPCR

The RT-qPCR reaction was set up as follows:

| COMPONENT | 20 µl REACTION | FINAL CONCENTRATION |
|---|---|---|
| Luna Universal Probe One-Step Reaction Mix (2X) | 10 µl | 1X |
| Luna WarmStart RT Enzyme Mix (20X) | 1 µl | 1X |
| Forward primer (10 µM) | 0.8 µl | 0.4 µM |
| Reverse primer (10 µM) | 0.8 µl | 0.4 µM |
| Probe (10 µM) | 0.4 µl | 0.2 µM |
| Template RNA | 2 µl | |
| Nuclease-free Water | 5 µl | |

The thermal cycler was set up as follows:

| CYCLE STEP | TEMPERATURE | TIME | CYCLES |
|---|---|---|---|
| Reverse Transcription | 55° C.* | 10 minutes | 1 |
| Initial Denaturation | 95° C. | 1 minute | 1 |
| Denaturation | 95° C. | 10 seconds | |
| Extension | 60° C. | CV seconds** (+plate read) | 45 |

SARS-CoV-2 RNA (Twist Biosciences, San Francisco, Calif.) and virus (SeraCare, Milford, Mass.) were spiked separately into different tubes of 2× saliva lysis buffer. The virus was previously spiked into saliva. A positive control contained purified RNA and a negative control contained water only. The results are consisted with those reported for RT-qPCR from saliva or nasopharyngeal swabs where detection limits were ascertained from 10 copies/sample (5000 cps/ml) up to 100,000 cps/ml.

Example 11: Lysis Buffer has Minimal or No Adverse Effects on RT-qPCR or on LAMP The lysis buffer as a whole had no adverse effects on the sensitivity of RT-qPCR or pH-dependent colorimetric LAMP. The results are shown in FIG. 24.

Example 12: Automation of a Workflow to Achieve a Throughput of 100,000 Reactions in about 20 Hours A workflow that is capable of delivering high volume throughput is illustrated in FIG. 28A-FIG. 28F and may include the following instruments: RNA collection tubes from Ora (Ottawa, Canada) (ORE-100), 96-384 tube to plate sample transfer (Bravo with 96 or 384 ST Head from Agilent, Santa Clara, Calif.), 384 well plate consumables (Corning, N.Y.), 384 well filling LAMP master mix into detection plates (BioTek, Winooski, Vt.), heat sealing of plates (Thermo Fisher, Waltham, Mass.), Automated 65° C. timed incubation (StoreX-Liconic Instruments) or Intek conveyer (Intek WA), Endpoint fluorescence (BioTek, Winooski, Vt.) or SpectraMax. Although any of these instruments can be switched out for other comparable devices, the workflow illustrates the suitability of colorimetric LAMP for high throughput workflows that are relatively simple, cost effective, efficient, and sensitive.

What is claimed is:

1. A kit for performing multiplex Loop-Mediated Isothermal Amplification (LAMP) on a clinical sample, comprising:
   (a) a primer mix comprising:
      (i) a first set of primers, wherein the primers of the first set independently hybridize to the genome of a strain of coronavirus or cDNA thereof, and are suitable for amplifying a first segment of the genome by reverse-transcription LAMP (RT-LAMP);
      (ii) a second set of primers, wherein the primers of the second set independently hybridize to the genome of the strain of coronavirus of (a)(i), or cDNA thereof and are suitable for amplifying a second segment of the genome by reverse-transcription LAMP (RT-LAMP);
   (b) a strand-displacing DNA polymerase; and
   (c) a reverse transcriptase.

2. The kit of claim 1, wherein the first and second sets of primers hybridize to the SARS-CoV-2 genome, or a cDNA thereof.

3. The kit of claim 2, wherein the first set of primers hybridizes to Gene E and the second set of primers hybridizes to Gene N.

4. The kit of claim 1, wherein the primer mix comprises:
   (iii) a third set of primers, wherein the primers of the third set independently hybridize to the genome of the strain of coronavirus virus of (a)(i), or cDNA thereof and are suitable for amplifying a third segment of the genome by reverse-transcription LAMP (RT-LAMP).

5. The kit of claim 4, wherein the first, second and third sets of primers independently hybridize to Gene Orf1, Gene E and Gene N in the SARS-CoV-2 genome.

6. The kit of claim 1, wherein the strand-displacing DNA polymerase is Bst polymerase or a variant thereof.

7. The kit of claim 1, wherein the strand-displacing DNA polymerase of (b) and the reverse transcriptase of (c) are in a master mix.

8. The kit of claim 7, wherein the master mix further comprises deoxynucleoside triphosphates and at least one indicator for detecting an amplification product by a change in color or fluorescence.

9. The kit of claim 8, wherein the indicator is selected from a metallochromic dye, a pH sensitive color dye, an intercalating dye and a fluorescent reporter indicator.

10. The kit of claim 7, wherein the master mix is lyophilized.

11. The kit of claim 7, wherein the master mix comprises the primer mix of (a).

12. The kit of claim 1, wherein the wherein (a), (b) and (c) are in separate containers.

13. The kit of claim 1, wherein the wherein (a), (b) and (c) are in the same container.

14. The kit according to claim 1, further comprising a viral inactivation mix.

15. The kit according to claim 14, wherein the viral inactivation mix is in a separate container.

16. The kit according to claim 14, wherein the viral inactivation mix comprises a reducing agent.

17. The kit according to claim 15, wherein the reducing agent is TCEP.

18. The kit according to claim 14, further comprising a guanidinium salt.

19. A method comprising:
  combining the primer mix and polymerase of the kit of claim 1, with a clinical sample to produce a reaction mix, the reaction mix comprising:
    the primer mix of (a);
    the strand-displacing DNA polymerase of (b);
    a reverse transcriptase of (c); and
    dNTPs; and
  incubating the reaction mix under conditions suitable for production of an RT-LAMP product if the clinical sample comprises the genome of a coronavirus.

20. The method of claim 19, wherein the first and second sets of primers hybridize to the SARS-CoV-2 genome, or a cDNA thereof.

21. The method of claim 19, wherein the clinical sample is from a patient that has COVID-19, shows symptoms of COVID-19, has been exposed to a person having COVID-19 or has previously had COVID-19.

22. The method of claim 19, wherein the clinical sample is or is made from a body fluid obtained from a patient.

23. The method of claim 22, wherein the bodily fluid is saliva.

24. The method of claim 19, wherein the clinical sample is or is made from a nasal or throat swab taken a patient.

25. The method according to claim 19, further comprising inactivating virus in the clinical sample with a reducing agent.

26. The method according to claim 25, wherein the reducing agent is TCEP.

27. The method according to claim 19, further comprising increasing sensitivity of the RT-LAMP with a guanidinium salt.

28. The method of claim 19, further comprising: detecting the RT-LAMP product.

29. The method of claim 19, wherein the reaction mix further comprises an indicator for detecting an RT-LAMP product by a change in color or fluorescence, and the method further comprises visualizing a color change by eye, measuring a change of color by means of a spectrophotometer or measuring fluorescence with a fluorescence spectrometer.

* * * * *

```
                       SEQUENCE LISTING

<160> NUMBER OF SEQ ID NOS: 69

<210> SEQ ID NO 1
<211> LENGTH: 62
<212> TYPE: DNA
<213> ORGANISM: Artificial Sequence
<220> FEATURE:
<223> OTHER INFORMATION: Synthetic construct

<400> SEQUENCE: 1
ccctatgtgt tcatcaaacg ttcggatgct cgaactgcac ctcatggtca tgttatggtt    60
ga                                                                  62

<210> SEQ ID NO 2
<211> LENGTH: 61
<212> TYPE: DNA
<213> ORGANISM: Artificial Sequence
<220> FEATURE:
<223> OTHER INFORMATION: Synthetic construct

<400> SEQUENCE: 2
gctggtagca gaactcgaag gcattcagta cggtcgtagt ggtgagacac ttggtgtcct    60
t                                                                   61

<210> SEQ ID NO 3
<211> LENGTH: 61
<212> TYPE: DNA
<213> ORGANISM: Artificial Sequence
<220> FEATURE:
<223> OTHER INFORMATION: Synthetic construct

<400> SEQUENCE: 3
gtccctcatg tgggcgaaat accagtggct taccgcaagg ttcttcttcg taagaacggt    60
a                                                                   61

<210> SEQ ID NO 4
<211> LENGTH: 61
<212> TYPE: DNA
<213> ORGANISM: Artificial Sequence
<220> FEATURE:
<223> OTHER INFORMATION: Synthetic construct

<400> SEQUENCE: 4
ataaaggagc tggtggccat agttacggcg ccgatctaaa gtcatttgac ttaggcgacg    60
a                                                                   61

<210> SEQ ID NO 5
<211> LENGTH: 24
<212> TYPE: DNA
<213> ORGANISM: Artificial Sequence
<220> FEATURE:
<223> OTHER INFORMATION: Synthetic construct

<400> SEQUENCE: 5
gcttggcact gatccttatg aaga                                          24

<210> SEQ ID NO 6
<211> LENGTH: 20
```

-continued

<212> TYPE: DNA
<213> ORGANISM: Artificial Sequence
<220> FEATURE:
<223> OTHER INFORMATION: Synthetic construct

<400> SEQUENCE: 6
ctgcacctca tggtcatgtt                                        20

<210> SEQ ID NO 7
<211> LENGTH: 19
<212> TYPE: DNA
<213> ORGANISM: Artificial Sequence
<220> FEATURE:
<223> OTHER INFORMATION: Synthetic construct

<400> SEQUENCE: 7
agctcgtcgc ctaagtcaa                                         19

<210> SEQ ID NO 8
<211> LENGTH: 42
<212> TYPE: DNA
<213> ORGANISM: Artificial Sequence
<220> FEATURE:
<223> OTHER INFORMATION: Synthetic construct

<400> SEQUENCE: 8
gagggacaag gacaccaagt gtatggttga gctggtagca ga               42

<210> SEQ ID NO 9
<211> LENGTH: 39
<212> TYPE: DNA
<213> ORGANISM: Artificial Sequence
<220> FEATURE:
<223> OTHER INFORMATION: Synthetic construct

<400> SEQUENCE: 9
ccagtggctt accgcaaggt tttagatcgg cgccgtaac                   39

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
ccgtactgaa tgccttcgag t                                      21

<210> SEQ ID NO 11
<211> LENGTH: 25
<212> TYPE: DNA
<213> ORGANISM: Artificial Sequence
<220> FEATURE:
<223> OTHER INFORMATION: Synthetic construct

<400> SEQUENCE: 11
ttcgtaagaa cggtaataaa ggagc                                  25

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
tcatcaaacg ttcggatgct                                          20

<210> SEQ ID NO 13
<211> LENGTH: 18
<212> TYPE: DNA
<213> ORGANISM: Artificial Sequence
<220> FEATURE:
<223> OTHER INFORMATION: Synthetic construct

<400> SEQUENCE: 13
tatggccacc agctcctt                                            18

<210> SEQ ID NO 14
<211> LENGTH: 42
<212> TYPE: DNA
<213> ORGANISM: Artificial Sequence
<220> FEATURE:
<223> OTHER INFORMATION: Synthetic construct

<400> SEQUENCE: 14
cgaccgtact gaatgccttc gagaactgca cctcatggtc at                 42

<210> SEQ ID NO 15
<211> LENGTH: 42
<212> TYPE: DNA
<213> ORGANISM: Artificial Sequence
<220> FEATURE:
<223> OTHER INFORMATION: Synthetic construct

<400> SEQUENCE: 15
agacacttgg tgtccttgtc ccagaagaac cttgcggtaa gc                 42

<210> SEQ ID NO 16
<211> LENGTH: 22
<212> TYPE: DNA
<213> ORGANISM: Artificial Sequence
<220> FEATURE:
<223> OTHER INFORMATION: Synthetic construct

<400> SEQUENCE: 16
ctgctaccag ctcaaccata ac                                       22

<210> SEQ ID NO 17
<211> LENGTH: 21
<212> TYPE: DNA
<213> ORGANISM: Artificial Sequence
<220> FEATURE:
<223> OTHER INFORMATION: Synthetic construct

<400> SEQUENCE: 17
tcatgtgggc gaaataccag t                                        21

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
ctgcacctca tggtcatgtt                                          20

<210> SEQ ID NO 19
<211> LENGTH: 19
<212> TYPE: DNA
<213> ORGANISM: Artificial Sequence
<220> FEATURE:
<223> OTHER INFORMATION: Synthetic construct

<400> SEQUENCE: 19
gatcagtgcc aagctcgtc                    19

<210> SEQ ID NO 20
<211> LENGTH: 41
<212> TYPE: DNA
<213> ORGANISM: Artificial Sequence
<220> FEATURE:
<223> OTHER INFORMATION: Synthetic construct

<400> SEQUENCE: 20
gagggacaag gacaccaagt gtggtagcag aactcgaagg c                    41

<210> SEQ ID NO 21
<211> LENGTH: 39
<212> TYPE: DNA
<213> ORGANISM: Artificial Sequence
<220> FEATURE:
<223> OTHER INFORMATION: Synthetic construct

<400> SEQUENCE: 21
ccagtggctt accgcaaggt tttagatcgg cgccgtaac                    39

<210> SEQ ID NO 22
<211> LENGTH: 21
<212> TYPE: DNA
<213> ORGANISM: Artificial Sequence
<220> FEATURE:
<223> OTHER INFORMATION: Synthetic construct

<400> SEQUENCE: 22
accactacga ccgtactgaa t                    21

<210> SEQ ID NO 23
<211> LENGTH: 25
<212> TYPE: DNA
<213> ORGANISM: Artificial Sequence
<220> FEATURE:
<223> OTHER INFORMATION: Synthetic construct

<400> SEQUENCE: 23
ttcgtaagaa cggtaataaa ggagc                    25

<210> SEQ ID NO 24
<211> LENGTH: 61
<212> TYPE: DNA
<213> ORGANISM: Artificial Sequence
<220> FEATURE:
<223> OTHER INFORMATION: Synthetic construct

<400> SEQUENCE: 24
atgaccaaat tggctactac cgaagagcta ccagacgaat tcgtggtggt gacggtaaaa     60
t                                                                    61

<210> SEQ ID NO 25
<211> LENGTH: 61
<212> TYPE: DNA
<213> ORGANISM: Artificial Sequence
<220> FEATURE:
<223> OTHER INFORMATION: Synthetic construct

<400> SEQUENCE: 25

```
gaaagatctc agtccaagat ggtatttcta ctacctagga actgggccag aagctggact    60
t                                                                    61

<210> SEQ ID NO 26
<211> LENGTH: 61
<212> TYPE: DNA
<213> ORGANISM: Artificial Sequence
<220> FEATURE:
<223> OTHER INFORMATION: Synthetic construct

<400> SEQUENCE: 26
ccctatggtg ctaacaaaga cggcatcata tgggttgcaa ctgagggagc cttgaataca    60
c                                                                    61

<210> SEQ ID NO 27
<211> LENGTH: 54
<212> TYPE: DNA
<213> ORGANISM: Artificial Sequence
<220> FEATURE:
<223> OTHER INFORMATION: Synthetic construct

<400> SEQUENCE: 27
caaaagatca cattggcacc cgcaatcctg ctaacaatgc tgcaatcgtg ctac          54

<210> SEQ ID NO 28
<211> LENGTH: 19
<212> TYPE: DNA
<213> ORGANISM: Artificial Sequence
<220> FEATURE:
<223> OTHER INFORMATION: Synthetic construct

<400> SEQUENCE: 28
tggctactac cgaagagct                                                 19

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
tgcagcattg ttagcaggat                                                20

<210> SEQ ID NO 30
<211> LENGTH: 41
<212> TYPE: DNA
<213> ORGANISM: Artificial Sequence
<220> FEATURE:
<223> OTHER INFORMATION: Synthetic construct

<400> SEQUENCE: 30
tctggcccag ttcctaggta gtccagacga attcgtggtg g                        41

<210> SEQ ID NO 31
<211> LENGTH: 40
<212> TYPE: DNA
<213> ORGANISM: Artificial Sequence
<220> FEATURE:
<223> OTHER INFORMATION: Synthetic construct

<400> SEQUENCE: 31
agacggcatc atatgggttg cacgggtgcc aatgtgatct                          40
```

```
<210> SEQ ID NO 32
<211> LENGTH: 25
<212> TYPE: DNA
<213> ORGANISM: Artificial Sequence
<220> FEATURE:
<223> OTHER INFORMATION: Synthetic construct

<400> SEQUENCE: 32
ggactgagat ctttcatttt accgt                                    25

<210> SEQ ID NO 33
<211> LENGTH: 21
<212> TYPE: DNA
<213> ORGANISM: Artificial Sequence
<220> FEATURE:
<223> OTHER INFORMATION: Synthetic construct

<400> SEQUENCE: 33
actgagggag ccttgaatac a                                        21

<210> SEQ ID NO 34
<211> LENGTH: 19
<212> TYPE: DNA
<213> ORGANISM: Artificial Sequence
<220> FEATURE:
<223> OTHER INFORMATION: Synthetic construct

<400> SEQUENCE: 34
accgaagagc taccagacg                                           19

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
tgcagcattg ttagcaggat                                          20

<210> SEQ ID NO 36
<211> LENGTH: 40
<212> TYPE: DNA
<213> ORGANISM: Artificial Sequence
<220> FEATURE:
<223> OTHER INFORMATION: Synthetic construct

<400> SEQUENCE: 36
tctggcccag ttcctaggta gttcgtggtg gtgacggtaa                    40

<210> SEQ ID NO 37
<211> LENGTH: 40
<212> TYPE: DNA
<213> ORGANISM: Artificial Sequence
<220> FEATURE:
<223> OTHER INFORMATION: Synthetic construct

<400> SEQUENCE: 37
agacggcatc atatgggttg cacgggtgcc aatgtgatct                    40

<210> SEQ ID NO 38
<211> LENGTH: 25
<212> TYPE: DNA
<213> ORGANISM: Artificial Sequence
<220> FEATURE:
<223> OTHER INFORMATION: Synthetic construct
```

```
<400> SEQUENCE: 38
ccatcttgga ctgagatctt tcatt                                          25

<210> SEQ ID NO 39
<211> LENGTH: 21
<212> TYPE: DNA
<213> ORGANISM: Artificial Sequence
<220> FEATURE:
<223> OTHER INFORMATION: Synthetic construct

<400> SEQUENCE: 39
actgagggag ccttgaatac a                                              21

<210> SEQ ID NO 40
<211> LENGTH: 19
<212> TYPE: DNA
<213> ORGANISM: Artificial Sequence
<220> FEATURE:
<223> OTHER INFORMATION: Synthetic construct

<400> SEQUENCE: 40
tccttgaact ttggtctcc                                                 19

<210> SEQ ID NO 41
<211> LENGTH: 23
<212> TYPE: DNA
<213> ORGANISM: Artificial Sequence
<220> FEATURE:
<223> OTHER INFORMATION: Synthetic construct

<400> SEQUENCE: 41
cagttcataa aggaattgat agc                                            23

<210> SEQ ID NO 42
<211> LENGTH: 45
<212> TYPE: DNA
<213> ORGANISM: Artificial Sequence
<220> FEATURE:
<223> OTHER INFORMATION: Synthetic construct

<400> SEQUENCE: 42
atccccagtc tgtgaaattg ggcaaaatgc tgggattata gatgt                    45

<210> SEQ ID NO 43
<211> LENGTH: 47
<212> TYPE: DNA
<213> ORGANISM: Artificial Sequence
<220> FEATURE:
<223> OTHER INFORMATION: Synthetic construct

<400> SEQUENCE: 43
gcagcagaaa gattattaac ttgggcagtt ggtaagtaaa tggaaga                  47

<210> SEQ ID NO 44
<211> LENGTH: 20
<212> TYPE: DNA
<213> ORGANISM: Artificial Sequence
<220> FEATURE:
<223> OTHER INFORMATION: Synthetic construct

<400> SEQUENCE: 44
agaaccagag gccaggcgag                                                20

<210> SEQ ID NO 45
<211> LENGTH: 22
```

<212> TYPE: DNA
<213> ORGANISM: Artificial Sequence
<220> FEATURE:
<223> OTHER INFORMATION: Synthetic construct

<400> SEQUENCE: 45
aggcagatag gcttagactc aa                                          22

<210> SEQ ID NO 46
<211> LENGTH: 18
<212> TYPE: DNA
<213> ORGANISM: Artificial Sequence
<220> FEATURE:
<223> OTHER INFORMATION: Synthetic construct

<400> SEQUENCE: 46
cggtggacaa attgtcac                                               18

<210> SEQ ID NO 47
<211> LENGTH: 22
<212> TYPE: DNA
<213> ORGANISM: Artificial Sequence
<220> FEATURE:
<223> OTHER INFORMATION: Synthetic construct

<400> SEQUENCE: 47
cttctctgga tttaacacac tt                                          22

<210> SEQ ID NO 48
<211> LENGTH: 28
<212> TYPE: DNA
<213> ORGANISM: Artificial Sequence
<220> FEATURE:
<223> OTHER INFORMATION: Synthetic construct

<400> SEQUENCE: 48
ttacaagctt aaagaatgtc tgaacact                                    28

<210> SEQ ID NO 49
<211> LENGTH: 27
<212> TYPE: DNA
<213> ORGANISM: Artificial Sequence
<220> FEATURE:
<223> OTHER INFORMATION: Synthetic construct

<400> SEQUENCE: 49
ttgaatttag gtgaaacatt tgtcacg                                     27

<210> SEQ ID NO 50
<211> LENGTH: 51
<212> TYPE: DNA
<213> ORGANISM: Artificial Sequence
<220> FEATURE:
<223> OTHER INFORMATION: Synthetic construct

<400> SEQUENCE: 50
tcagcacaca aagccaaaaa tttatttttc tgtgcaaagg aaattaagga g           51

<210> SEQ ID NO 51
<211> LENGTH: 49
<212> TYPE: DNA
<213> ORGANISM: Artificial Sequence
<220> FEATURE:
<223> OTHER INFORMATION: Synthetic construct

<400> SEQUENCE: 51
tattggtgga gctaaactta aagccttttc tgtacaatcc ctttgagtg      49

<210> SEQ ID NO 52
<211> LENGTH: 21
<212> TYPE: DNA
<213> ORGANISM: Artificial Sequence
<220> FEATURE:
<223> OTHER INFORMATION: Synthetic construct

<400> SEQUENCE: 52
accaggaact aatcagacaa g      21

<210> SEQ ID NO 53
<211> LENGTH: 25
<212> TYPE: DNA
<213> ORGANISM: Artificial Sequence
<220> FEATURE:
<223> OTHER INFORMATION: Synthetic construct

<400> SEQUENCE: 53
gacttgatct ttgaaatttg gatct      25

<210> SEQ ID NO 54
<211> LENGTH: 42
<212> TYPE: DNA
<213> ORGANISM: Artificial Sequence
<220> FEATURE:
<223> OTHER INFORMATION: Synthetic construct

<400> SEQUENCE: 54
ttccgaagaa cgctgaagcg gaactgatta caaacattgg cc      42

<210> SEQ ID NO 55
<211> LENGTH: 40
<212> TYPE: DNA
<213> ORGANISM: Artificial Sequence
<220> FEATURE:
<223> OTHER INFORMATION: Synthetic construct

<400> SEQUENCE: 55
cgcattggca tggaagtcac aatttgatgg cacctgtgta      40

<210> SEQ ID NO 56
<211> LENGTH: 21
<212> TYPE: DNA
<213> ORGANISM: Artificial Sequence
<220> FEATURE:
<223> OTHER INFORMATION: Synthetic construct

<400> SEQUENCE: 56
gggggcaaat tgtgcaattt g      21

<210> SEQ ID NO 57
<211> LENGTH: 20
<212> TYPE: DNA
<213> ORGANISM: Artificial Sequence
<220> FEATURE:
<223> OTHER INFORMATION: Synthetic construct

<400> SEQUENCE: 57
cttcgggaac gtggttgacc      20

<210> SEQ ID NO 58
<211> LENGTH: 23
<212> TYPE: DNA
<213> ORGANISM: Artificial Sequence

```
<220> FEATURE:
<223> OTHER INFORMATION: Synthetic construct

<400> SEQUENCE: 58
tgagtacgaa cttatgtact cat                                            23

<210> SEQ ID NO 59
<211> LENGTH: 22
<212> TYPE: DNA
<213> ORGANISM: Artificial Sequence
<220> FEATURE:
<223> OTHER INFORMATION: Synthetic construct

<400> SEQUENCE: 59
ttcagatttt taacacgaga gt                                             22

<210> SEQ ID NO 60
<211> LENGTH: 42
<212> TYPE: DNA
<213> ORGANISM: Artificial Sequence
<220> FEATURE:
<223> OTHER INFORMATION: Synthetic construct

<400> SEQUENCE: 60
accacgaaag caagaaaaag aagttcgttt cggaagagac ag                       42

<210> SEQ ID NO 61
<211> LENGTH: 44
<212> TYPE: DNA
<213> ORGANISM: Artificial Sequence
<220> FEATURE:
<223> OTHER INFORMATION: Synthetic construct

<400> SEQUENCE: 61
ttgctagtta cactagccat ccttaggttt tacaagactc acgt                     44

<210> SEQ ID NO 62
<211> LENGTH: 19
<212> TYPE: DNA
<213> ORGANISM: Artificial Sequence
<220> FEATURE:
<223> OTHER INFORMATION: Synthetic construct

<400> SEQUENCE: 62
gcgcttcgat tgtgtgcgt                                                 19

<210> SEQ ID NO 63
<211> LENGTH: 18
<212> TYPE: DNA
<213> ORGANISM: Artificial Sequence
<220> FEATURE:
<223> OTHER INFORMATION: Synthetic construct

<400> SEQUENCE: 63
cgctattaac tattaacg                                                  18

<210> SEQ ID NO 64
<211> LENGTH: 18
<212> TYPE: DNA
<213> ORGANISM: Artificial Sequence
<220> FEATURE:
<223> OTHER INFORMATION: Synthetic construct

<400> SEQUENCE: 64
agtaccccat cgagcacg                                                  18
```

```
<210> SEQ ID NO 65
<211> LENGTH: 20
<212> TYPE: DNA
<213> ORGANISM: Artificial Sequence
<220> FEATURE:
<223> OTHER INFORMATION: Synthetic construct

<400> SEQUENCE: 65
agcctggata gcaacgtaca                                               20

<210> SEQ ID NO 66
<211> LENGTH: 40
<212> TYPE: DNA
<213> ORGANISM: Artificial Sequence
<220> FEATURE:
<223> OTHER INFORMATION: Synthetic construct

<400> SEQUENCE: 66
gagccacacg cagctcattg tatcaccaac tgggacgaca                         40

<210> SEQ ID NO 67
<211> LENGTH: 38
<212> TYPE: DNA
<213> ORGANISM: Artificial Sequence
<220> FEATURE:
<223> OTHER INFORMATION: Synthetic construct

<400> SEQUENCE: 67
ctgaacccca aggccaaccg gctggggtgt tgaaggtc                           38

<210> SEQ ID NO 68
<211> LENGTH: 21
<212> TYPE: DNA
<213> ORGANISM: Artificial Sequence
<220> FEATURE:
<223> OTHER INFORMATION: Synthetic construct

<400> SEQUENCE: 68
tgtggtgcca gattttctcc a                                             21

<210> SEQ ID NO 69
<211> LENGTH: 23
<212> TYPE: DNA
<213> ORGANISM: Artificial Sequence
<220> FEATURE:
<223> OTHER INFORMATION: Synthetic construct

<400> SEQUENCE: 69
cgagaagatg acccagatca tgt                                           23
```